(12) United States Patent
Yamashita et al.

(10) Patent No.: US 12,071,511 B2
(45) Date of Patent: Aug. 27, 2024

(54) POLYETHER GROUP-CONTAINING COMPOUND

(71) Applicant: DAIKIN INDUSTRIES, LTD., Osaka (JP)

(72) Inventors: Tsuneo Yamashita, Osaka (JP); Takashi Nomura, Osaka (JP); Kaori Ozawa, Osaka (JP); Hisashi Mitsuhashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 519 days.

(21) Appl. No.: 17/331,096

(22) Filed: May 26, 2021

(65) Prior Publication Data
US 2021/0284798 A1  Sep. 16, 2021

Related U.S. Application Data

(63) Continuation of application No. PCT/JP2019/046418, filed on Nov. 27, 2019.

(30) Foreign Application Priority Data

Nov. 30, 2018 (JP) .................................. 2018-225935

(51) Int. Cl.
| | |
|---|---|
| C07D 251/46 | (2006.01) |
| C07D 251/52 | (2006.01) |
| C07F 7/18 | (2006.01) |
| C08G 65/333 | (2006.01) |
| C08G 65/334 | (2006.01) |
| C08G 65/336 | (2006.01) |
| C08G 77/46 | (2006.01) |
| C07F 7/08 | (2006.01) |

(52) U.S. Cl.
CPC ......... *C08G 65/336* (2013.01); *C07D 251/46* (2013.01); *C07D 251/52* (2013.01); *C07F 7/1876* (2013.01); *C08G 65/333* (2013.01); *C08G 65/3348* (2013.01); *C08G 77/46* (2013.01); *C07F 7/0812* (2013.01)

(58) Field of Classification Search
CPC .... C07F 7/0812; C07F 7/1876; C07D 251/46; C07D 251/52
See application file for complete search history.

(56) References Cited

U.S. PATENT DOCUMENTS

| | | | | |
|---|---|---|---|---|
| 5,288,891 A | * | 2/1994 | Sawada ................ | C07F 7/1896 556/454 |
| 6,183,872 B1 | | 2/2001 | Tanaka et al. | |
| 6,391,948 B1 | * | 5/2002 | Clark .................... | C09D 5/1625 428/496 |
| 6,448,428 B1 | * | 9/2002 | Furukawa ............. | C09K 3/18 556/463 |
| 2009/0208728 A1 | | 8/2009 | Itami et al. | |

FOREIGN PATENT DOCUMENTS

| | | |
|---|---|---|
| JP | 2004-146478 A | 5/2004 |
| JP | 2008-534696 A | 8/2008 |
| JP | 2012-207169 A | 10/2012 |
| WO | 97/07155 A1 | 2/1997 |

OTHER PUBLICATIONS

International Search Report for PCT/JP2019/046418 dated, Feb. 18, 2020 (PCT/ISA/210).
Extended European Search Report dated Jul. 21, 2022 in corresponding European Application No. 19890177.9.
International Preliminary Report on Patentability with the translation of Written Opinion dated Jun. 10, 2021 from the International Bureau in International Application No. PCT/JP2019/046418.

\* cited by examiner

*Primary Examiner* — Margaret G Moore
(74) *Attorney, Agent, or Firm* — Sughrue Mion, PLLC

(57) ABSTRACT

A polyether group-containing compound of the formula (I). In each of the compound of the formula (I), one or two R— are represented by $(Rf-X^{f1}-PE-X^{f2})_\alpha—X^1—$, and one or two R— are represented by $R^{Si}—$. The symbols are as defined in the description.

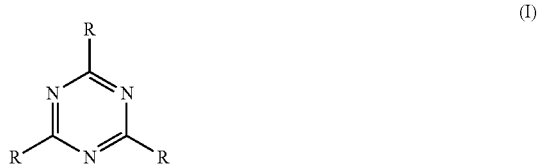

(I)

11 Claims, No Drawings

POLYETHER GROUP-CONTAINING COMPOUND

CROSS-REFERENCE TO RELATED APPLICATIONS

This application is a Rule 53 (b) Continuation of International Application No. PCT/JP2019/046418 filed Nov. 27, 2019, which claims priority based on Japanese Patent Application No. 2018-225935 filed Nov. 30, 2018, the respective disclosures of which are incorporated herein by reference in their entirety.

TECHNICAL FIELD

The present disclosure relates to a polyether group-containing compound.

BACKGROUND ART

Certain types of fluorine-containing silane compounds are known to be capable of providing excellent water-repellency, oil-repellency, antifouling properties, and the like when used in surface treatment of a base material. A layer obtained from a surface-treating agent containing a fluorine-containing silane compound (hereinafter, also referred to as a "surface-treating layer") is applied as a so-called functional thin film to a large variety of base materials such as glass, plastics, fibers, and building materials.

A known such fluorine-containing compound is a perfluoropolyether group-containing silane compound having a perfluoropolyether group in the molecular backbone and a hydrolyzable group bonding to a Si atom at the molecular terminal or in the terminal part (See Patent Literatures 1 and 2).

PRIOR ART LITERATURE

Patent Literature

Patent Literature 1: JP 2008-534696 A
Patent Literature 2: International Publication No. WO 97/07155

SUMMARY

Solution to Problem

The present disclosure provides [1] below.

[1] A polyether group-containing compound of formula (I):

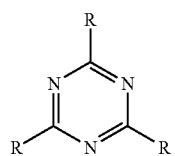
(I)

wherein
one or two R— groups are represented by (Rf-$X^{f1}$-PE-$X^{f2}$)$_\alpha$—$X^1$—, and one or two R— groups are represented by $R^{Si}$—;
the total number of (Rf-$X^{f1}$-PE-$X^{f2}$)$_\alpha$—$X^1$— and $R^{Si}$— is 3;

$\alpha$ is an integer of 1 to 9;
Rf is independently at each occurrence an alkyl group having 1 to 16 carbon atoms, optionally substituted with one or more fluorine atoms;
PE is each independently at each occurrence a group represented by formula:

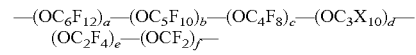

wherein a, b, c, d, e, and f are each independently an integer of 0 or more and 200 or less, the sum of a, b, c, d, e, and f is at least 1, the occurrence order of the respective repeating units enclosed in parentheses provided with a, b, c, d, e, or f is not limited in the formula, and $X^{10}$ is each independently at each occurrence a hydrogen atom, a fluorine atom, or a chlorine atom;
$X^{f1}$ is represented by $(X^{f11})_z$;
$X^{f11}$ is an alkylene group having 1 to 6 carbon atoms wherein a hydrogen atom is optionally replaced with a fluorine atom;
z is each independently at each occurrence 0 or 1;
$X^{f2}$ is represented by $(O)_y$ or $(NH)_y$;
y is each independently at each occurrence 0 or 1;
$X^1$ is each independently at each occurrence a single bond, an oxygen atom, a nitrogen atom, a sulfur atom, —NH—, —SO$_2$NH—, —SO$_2$—, or a di- to decavalent organic group;
$R^{Si}$— is each independently at each occurrence represented by any of the following formulae (A1) to (A4):

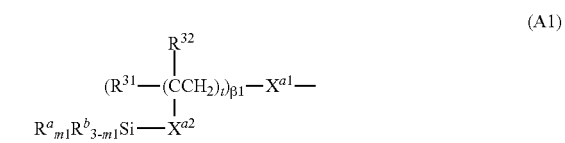
(A1)

(A2)

(A3)

(A4)

$R^a$ is each independently at each occurrence a hydroxyl group or a hydrolyzable group;
$R^b$ is each independently at each occurrence a hydrogen atom or an alkyl group having 1 to 20 carbon atoms;
m1 is each independently at each occurrence an integer of 0 to 3;
$X^{a1}$, $X^{a3}$, $X^{a4}$, and $X^{a5}$ are each independently at each occurrence (—($R^{71}$)$_{n21}$—)$_2$N—($R^{72}$)$_{n22}$—, —($R^{71}$)$_{n21}$—$X^3$—($R^{72}$)$_{n22}$—, —$R^{73}$—, or —Y—O—;
$R^{71}$ is each independently at each occurrence —(CH$_2$)$_{n23}$—, an o-, m-, or p-phenylene group, which may be substituted with one or more fluorine atoms;
n23 is each independently at each occurrence an integer of 1 to 20;
$R^{72}$ is each independently at each occurrence
j—(CH$_2$)$_{n24}$—, an o-, m-, or p-phenylene group, which may be substituted with one or more fluorine atoms;
n24 is each independently at each occurrence an integer of 1 to 20;
n21 is each independently at each occurrence 0 or 1;
n22 is each independently at each occurrence 0 or 1;
the sum of n21 and n22 is 1 or more;
$X^3$ is each independently at each occurrence —O—, —(O$R^{74}$)$_{n25}$—, —S—, —C(=O)—, —C(=O) O—, —O—C(=O)—, —O—C(=O)—O—, —Si($R^{75}$)$_2$—, —(Si($R^{75}$)$_2$O)$_{n26}$—Si($R^{75}$)$_2$—, —$NR^3$C(=O)—, —C(=O)$NR^3$—, —$NR^3$C(=O)$NR^3$—, —$NR^3$C(=O)O—, —O—C(=O)$NR^3$—, —$NR^3$—, —SO$_2NR^3$—, or —SO$_2$—;

$R^{74}$ is each independently at each occurrence a $C_{1-6}$ alkylene group;

n25 is each independently at each occurrence an integer of 1 to 5;

$R^{75}$ is each independently at each occurrence a phenyl group, a $C_{1-6}$ alkyl group, or a $C_{1-6}$ alkoxy group;

n26 is each independently at each occurrence an integer of 1 to 100;

$R^3$ is each independently at each occurrence a hydrogen atom, a phenyl group, or an alkyl group having 1 to 6 carbon atoms;

$R^{73}$ is each independently at each occurrence —(CH$_2$)$_{n27}$—;

n27 is an integer of 1 to 20; and

Y is a di- to hexavalent hydrocarbon group and has a silicon atom and/or a siloxane bond;

$X^{a2}$ is a single bond or a divalent organic group;

β1, β2, β3, and β4 are each independently at each occurrence an integer of 1 to 9;

t is each independently at each occurrence an integer of 2 to 10;

$R^{31}$ is each independently at each occurrence a hydrogen atom or a halogen atom;

$R^{32}$ is each independently at each occurrence a hydrogen atom or a monovalent organic group;

in formula (A1), there is at least one $R^a_{m1}R^b_{3-m1}$Si— wherein m1 is 1 to 3, and in formula (A2), there is at least one $R^a_{m1}R^b_{3-m1}$Si— wherein m1 is 1 to 3;

$R^{f1}$ is each independently at each occurrence $R^{41}_{r1}R^{42}_{r2}R^{43}_{r3}$Si-$Z^1$—;

$Z^1$ is each independently at each occurrence an oxygen atom or a divalent organic group;

$R^{41}$ is each independently at each occurrence $R^{f1'}$;

$R^{f1'}$ has the same definition as that of $R^{f1}$;

in $R^{f1}$, the number of Si atoms linearly connected via the group $Z^1$ is up to 5;

$R^{42}$ is each independently at each occurrence a hydroxyl group or a hydrolyzable group;

$R^{43}$ is each independently at each occurrence a hydrogen atom or a monovalent organic group;

r1 is each independently at each occurrence an integer of 0 to 3;

r2 is each independently at each occurrence an integer of 0 to 3;

r3 is each independently at each occurrence an integer of 0 to 3;

in each $R^{41}_{r1}R^{42}_{r2}R^{43}_{r3}$Si-$Z^1$—, the sum of r1, r2, and r3 is 3;

$R^{f2}$ is each independently at each occurrence a hydroxyl group or a hydrolyzable group;

$R^{f3}$ is each independently at each occurrence a hydrogen atom or a monovalent organic group;

p1 is each independently at each occurrence an integer of 0 to 3;

p2 is each independently at each occurrence an integer of 0 to 3;

p3 is each independently at each occurrence an integer of 0 to 3;

in each $R^{f3}_{p3}R^{f2}_{p2}R^{f1}_{p1}$Si—, the sum of p1, p2, and p3 is 3, and in formula (A3), there are at least two Si atoms to which a hydroxyl group or a hydrolyzable group binds;

$R^{g1}$ is each independently at each occurrence $R^{51}_{s1}R^{52}_{s2}R^{53}_{s3}$C-$Z^2$—;

$Z^2$ is each independently at each occurrence an oxygen atom or a divalent organic group;

$R^{51}$ is each independently at each occurrence $R^{g1'}$;

$R^{g1'}$ has the same definition as that of $R^{g1}$;

in $R^{g1}$, the number of C atoms linearly connected via the group $Z^2$ is up to 5;

$R^{52}$ is each independently at each occurrence $R^a_{m1}R^b_{3-m1}$Si-$Z^3$—;

$Z^3$ is each independently at each occurrence an oxygen atom or a divalent organic group;

$R^{53}$ is each independently at each occurrence a hydrogen atom, a hydroxyl group, or a monovalent organic group;

s1 is each independently at each occurrence an integer of 0 to 3;

s2 is each independently at each occurrence an integer of 0 to 3;

s3 is each independently at each occurrence an integer of 0 to 3;

in each $R^{51}_{s1}R^{52}_{s2}R^{53}_{s3}$C-$Z^2$—, the sum of s1, s2, and s3 is 3;

$R^{g2}$ is each independently at each occurrence $R^a_{m1}R^b_{3-m1}$Si-$Z^4$—;

$Z^4$ is each independently at each occurrence an oxygen atom or a divalent organic group;

$R^{g3}$ is each independently at each occurrence a hydrogen atom, a hydroxyl group, or a monovalent organic group;

q1 is each independently at each occurrence an integer of 0 to 3;

q2 is each independently at each occurrence an integer of 0 to 3; and q3 is each independently at each occurrence an integer of 0 to 3;

in each $R^{g3}_{q3}R^{g2}_{q2}R^{g1}_{q1}$C—, the sum of q1, q2, and q3 is 3, and in formula (A4), there are at least two $R^a_{m1}R^b_{3-m1}$Si— wherein m1 is 1 to 3.

Advantageous Effect of Invention

The present disclosure provides a compound that has a novel structure and can be used in surface treatment of a base material.

DESCRIPTION OF EMBODIMENTS

The term "hydrocarbon group", as used herein, represents a group that contains a carbon and a hydrogen and that is obtained by removing one hydrogen atom from a hydrocarbon. The hydrocarbon group is not limited, and examples include a hydrocarbon group that has 1 to 20 carbon atoms and that is optionally substituted with one or more substituents, such as an aliphatic hydrocarbon group and an aromatic hydrocarbon group. The "aliphatic hydrocarbon group" may be either straight, branched, or cyclic, and may be either saturated or unsaturated. The hydrocarbon group may contain one or more ring structures. The hydrocarbon group may have one or more of N, O, S, Si, amide, sulfonyl, siloxane, carbonyl, carbonyloxy, and the like at the terminal or in the molecular chain thereof.

The substituent of the "hydrocarbon group", as used herein, is not limited, and examples include one or more groups selected from a halogen atom, and a $C_{1-6}$ alkyl group, a $C_{2-6}$ alkenyl group, a $C_{2-6}$ alkynyl group, a $C_{3-10}$ cycloalkyl group, a $C_{3-10}$ unsaturated cycloalkyl group, a 5 to 10-membered heterocyclyl group, a 5 to 10-membered unsaturated heterocyclyl group, a $C_{6-10}$ aryl group, and a 5 to 10-membered heteroaryl group each optionally substituted with one or more halogen atoms.

The term "organic group", as used herein, represents a group containing a carbon. The organic group is not limited, and may be a hydrocarbon group. The term "di- to decavalent organic group" represents a di- to decavalent group containing carbon. The di- to decavalent organic group may be, but is not limited to, a di- to decavalent group obtained by further removing 1 to 9 hydrogen atoms from a hydrocarbon group. For example, the divalent organic group may be, but is not limited to, a divalent group obtained by further removing one hydrogen atom from a hydrocarbon group.

The term "hydrolyzable group", as used herein, represents a group which is able to undergo a hydrolysis reaction, i.e., represents a group that can be removed from the main backbone of a compound by a hydrolysis reaction. Examples of the hydrolyzable group include —$OR^{a1}$, —$OCOR^{a1}$, —O—N=$CR^{a1}{}_2$, —$NR^{a1}{}_2$, —$NHR^{a1}$, and halogen (in these formulae, $R^{a1}$ represents a substituted or unsubstituted alkyl group having 1 to 4 carbon atoms), and —$OR^{a1}$ (i.e., an alkoxy group) is preferable. Examples of $R^{a1}$ include unsubstituted alkyl groups such as a methyl group, an ethyl group, a propyl group, an isopropyl group, a n-butyl group, and an isobutyl group; and substituted alkyl groups such as a chloromethyl group. Among such groups, an alkyl group, in particular an unsubstituted alkyl group, is preferable, and a methyl group or an ethyl group is more preferable.

The polyether group (hereinafter, sometimes referred to as "PE")-containing compound of the present disclosure is represented by formula (I).

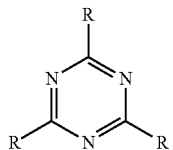

(I)

The polyether group-containing compound of the present disclosure has a triazine ring within the molecular structure as in the above formula (I). The polyether group-containing compound of the present disclosure has a ring structure that has a high electron density and that has the smallest ring structure in organic compounds having 6-membered ring, thus unlikely undergoes a nucleophilic substitution reaction of an anion compound, and can stably exist, for example, under alkaline conditions. Moreover, even if the carbon-hydrogen bond of the triazine ring is substituted with an ether bond or an ester bond, the polyether group-containing compound unlikely undergoes hydrolysis in the presence of an acid or an alkali. Furthermore, since the triazine ring has good heat resistance and ultraviolet (UV) resistance, the polyether group-containing compound of the present disclosure may have good heat resistance and UV resistance.

In formula (I), R— is each independently at each occurrence a group represented by (Rf-$X^{f1}$-PE-$X^{f2}$)$_\alpha$—$X^1$— or a group represented by $R^{Si}$—.

One or two R groups are groups represented by (Rf-$X^{f1}$-PE-$X^{f2}$)$_\alpha$—$X^1$—, and one or two R groups are groups represented by $R^{Si}$—, provided that the total number of groups represented by (Rf-PE)$_\alpha$—$X^1$— and groups represented by $R^{Si}$— is 3. Having such a structure, the polyether group-containing compound of the present disclosure can contribute to forming a surface-treating layer that has water-repellency, oil-repellency, antifouling properties, chemical resistance, UV durability, and the like and that has good adhesion to a base material.

Preferably, one or two R groups are groups represented by (Rf-$X^{f1}$-PE-$X^{f2}$)$_\alpha$—$X^1$—, and one or two R groups are groups represented by $R^{Si}$—, provided that the total of the number of groups represented by (Rf-$X^{f1}$-PE-$X^{f2}$)$_\alpha$—$X^1$— and the number of groups represented by $R^{Si}$— is 3.

In one embodiment, one R group is a group represented by (Rf-$X^{f1}$-PE-$X^{f2}$)$_\alpha$—$X^1$—, and two R groups are groups represented by $R^{Si}$—. Having such a structure, the polyether group-containing compound of the present disclosure can contribute to forming a surface-treating layer that has water-repellency, oil-repellency, antifouling properties, chemical resistance, UV resistance, and the like. Due to the structure as described above, the polyether group-containing compound of the present disclosure can form intermolecular bonding, and, moreover, the formed surface-treating layer can have good adhesion to a base material.

In one embodiment, two R groups are groups represented by (Rf-$X^{f1}$-PE-$X^{f2}$)$_\alpha$—$X^1$—, and one R group is a group represented by $R^{Si}$—. Having such a structure, the polyether group-containing compound of the present disclosure has high content of polyether chain content per one molecule, and thus can contribute to forming a surface-treating layer that has high water-repellency, oil-repellency, antifouling properties, chemical resistance, UV resistance, and the like and that has good adhesion to a base material.

[Group Represented by (Rf-$X^{f1}$-PE-$X^{f2}$)$_\alpha$—$X^1$—]

The polyether group-containing compound of the present disclosure has a group represented by (Rf-$X^{f1}$-PE-$X^{f2}$)$_\alpha$—$X^1$—. Having such a structure, the polyether group-containing compound of the present disclosure can form a layer that has good water-repellency, oil-repellency, chemical resistance (e.g., resistance to salt water, an acidic or basic aqueous solution, acetone, oleic acid, or hexane), UV resistance, and the like.

Rf independently at each occurrence represents an alkyl group that has 1 to 16 carbon atoms and that is optionally substituted with one or more fluorine atoms.

In the alkyl group that has 1 to 16 carbon atoms and that is optionally substituted with one or more fluorine atoms, the "alkyl group that has 1 to 16 carbon atoms" may be straight or branched, and is preferably a straight or branched alkyl group having 1 to 6 carbon atoms, in particular 1 to 3 carbon atoms, and more preferably a straight alkyl group having 1 to 3 carbon atoms.

Rf is preferably an alkyl group that has 1 to 16 carbon atoms and that is substituted with one or more fluorine atoms, more preferably a $CF_2H$—$C_{1-15}$ fluoroalkylene group, and even more preferably a perfluoroalkyl group having 1 to 16 carbon atoms.

The perfluoroalkyl group having 1 to 16 carbon atoms may be straight or branched, and is preferably a straight or branched perfluoroalkyl group having 1 to 6 carbon atoms, in particular 1 to 3 carbon atoms, more preferably a straight perfluoroalkyl group having 1 to 3 carbon atoms, and specifically —$CF_3$, —$CF_2CF_3$, or —$CF_2CF_2CF_3$.

In the above formula, PE is each independently at each occurrence a divalent organic group represented by formula:

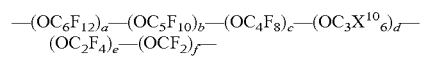

wherein a, b, c, d, e, and f are each independently an integer of 0 or more and 200 or less, and the sum of a, b, c, d, e, and f is at least 1. Preferably, a, b, c, d, e, and f each independently represent an integer of 0 or more and 100 or less. The sum of a, b, c, d, e, and f is preferably 5 or more, and more preferably 10 or more, such as 10 or more and 100 or less. The occurrence order of the respective repeating units enclosed in parentheses provided with a, b, c, d, e, or f is not limited in the formula. $X^{10}$ is each independently at each occurrence a hydrogen atom, a fluorine atom, or a chlorine atom, preferably a hydrogen atom or a fluorine atom, and more preferably a fluorine atom. Herein, the left side of the group of PE binds to $X^{f1}$, and the right side of PE binds to $X^{f2}$.

These repeating units may be straight or branched, and are preferably straight. For example, $—(OC_6F_{12})—$ may be $—(OCF_2CF_2CF_2CF_2CF_2CF_2)—$, $—(OCF(CF_3)CF_2CF_2CF_2CF_2)—$, $—(OCF_2CF(CF_3)CF_2CF_2CF_2)—$, $—(OCF_2CF_2CF(CF_3)CF_2CF_2)—$, $—(OCF_2CF_2CF_2CF(CF_3)CF_2)—$, $—(OCF_2CF_2CF_2CF_2CF(CF_3))—$, or the like, and is preferably $—(OCF_2CF_2CF_2CF_2CF_2CF_2)—$. $—(OC_5F_{10})—$ may be $—(OCF_2CF_2CF_2CF_2CF_2)—$, $—(OCF(CF_3)CF_2CF_2CF_2)—$, $—(OCF_2CF(CF_3)CF_2CF_2)—$, $—(OCF_2CF_2CF(CF_3)CF_2)—$, $—(OCF_2CF_2CF_2CF(CF_3))—$, or the like, and is preferably $—(OCF_2CF_2CF_2CF_2CF_2)—$. $—(OC_4F_8)—$ may be any of $—(OCF_2CF_2CF_2CF_2)—$, $—(OCF(CF_3)CF_2CF_2)—$, $—(OCF_2CF(CF_3)CF_2)—$, $—(OCF_2CF_2CF(CF_3))—$, $—(OC(CF_3)_2CF_2)—$, $—(OCF_2C(CF_3)_2)—$, $—(OCF(CF_3)CF(CF_3))—$, $—(OCF(C_2F_5)CF_2)—$, and $—(OCF_2CF(C_2F_5))—$, and is preferably $—(OCF_2CF_2CF_2CF_2)—$. $—(OC_3F_6)—$ (that is to say, in the above formula, $X^{10}$ is a fluorine atom) may be any of $—(OCF_2CF_2CF_2)—$, $—(OCF(CF_3)CF_2)—$, and $—(OCF_2CF(CF_3))—$, and is preferably $—(OCF_2CF_2CF_2)—$. Also, $—(OC_2F_4)—$ may be any of $—(OCF_2CF_2)—$ and $—(OCF(CF_3))—$, and is preferably $—(OCF_2CF_2)—$.

In one embodiment, PE is $—(OC_3F_6)_d—$ wherein d is an integer of 1 or more and 200 or less, preferably 5 or more and 200 or less, and more preferably 10 or more and 200 or less. Preferably, PE is $—(OCF_2CF_2CF_2)_d—$ wherein d is an integer of 1 or more and 200 or less, preferably 5 or more and 200 or less, and more preferably 10 or more and 200 or less, or $—(OCF(CF_3)CF_2)_d—$ wherein d is an integer of 1 or more and 200 or less, preferably 5 or more and 200 or less, and more preferably 10 or more and 200 or less. More preferably, PE is $—(OCF_2CF_2CF_2)_d—$ wherein d is an integer of 1 or more and 200 or less, preferably 5 or more and 200 or less, and more preferably 10 or more and 200 or less.

In one embodiment, PE is preferably $—(OC_3F_6)_d—$ wherein d is an integer of 10 or more and 100 or less, more preferably d is an integer of 15 or more and 50 or less, and even more preferably d is an integer of 25 or more and 35 or less.

In another embodiment, PE is $—(OC_4F_8)_c—(OC_3F_6)_d—(OC_2F_4)_e—(OCF_2)_f—$ wherein c and d are each independently an integer of 0 or more and 30 or less, e and f are each independently an integer of 1 or more and 200 or less, preferably 5 or more and 200 or less, and more preferably 10 or more and 200 or less, the sum of c, d, e, and f is at least 5 or more, and preferably 10 or more, and the occurrence order of the respective repeating units enclosed in parentheses provided with a subscript c, d, e, or f is not limited in the formula. Preferably, PE is $—(OCF_2CF_2CF_2CF_2)_c—(OCF_2CF_2CF_2)_d—(OCF_2CF_2)_e—(OCF_2)_f—$. In one embodiment, PE may be $—(OC_2F_4)_e—(OCF_2)_f—$ wherein e and f are each independently an integer of 1 or more and 200 or less, preferably 5 or more and 200 or less, and more preferably 10 or more and 200 or less, and the occurrence order of the respective repeating units enclosed in parentheses provided with a subscript e or f is not limited in the formula.

In yet another embodiment, PE is a group represented by $—(R^6—R^7)_g—$ wherein $R^6$ is $OCF_2$ or $OC_2F_4$, and preferably $OC_2F_4$; and $R^7$ is a group selected from $OC_2F_4$, $OC_3F_6$, $OC_4F_8$, $OC_5F_{10}$, and $OC_6F_{12}$, or a combination of two or three groups independently selected from these groups. Preferably, $R^7$ is a group selected from $OC_2F_4$, $OC_3F_6$, and $OC_4F_8$, or a combination of two or three groups independently selected from these groups, and more preferably a group selected from $OC_3F_6$ and $OC_4F_8$. Examples of the combination of 2 or 3 groups independently selected from $OC_2F_4$, $OC_3F_6$, and $OC_4F_8$ include, but are not limited to, $—OC_2F_4OC_3F_6—$, $—OC_2F_4OC_4F_8—$, $—OC_3F_6OC_2F_4—$, $—OC_3F_6OC_3F_6—$, $—OC_3F_6OC_4F_8—$, $—OC_4F_8OC_4F_8—$, $—OC_4F_8OC_3F_6—$, $—OC_4F_8OC_2F_4—$, $—OC_2F_4OC_2F_4OC_3F_6—$, $—OC_2F_4OC_2F_4OC_4F_8—$, $—OC_2F_4OC_3F_6OC_2F_4—$, $—OC_2F_4OC_3F_6OC_3F_6—$, $—OC_2F_4OC_4F_8OC_2F_4—$, $—OC_3F_6OC_2F_4OC_2F_4—$, $—OC_3F_6OC_2F_4OC_3F_6—$, $—OC_3F_6OC_3F_6OC_2F_4—$, and $—OC_4F_8OC_2F_4OC_2F_4—$. g is an integer of 2 or more, preferably 3 or more, and more preferably 5 or more, and is 100 or less and preferably 50 or less. In the formula, $OC_2F_4$, $OC_3F_6$, $OC_4F_8$, $OC_5F_{10}$, and $OC_6F_{12}$ may be either straight or branched, and are preferably straight. In this embodiment, PE is preferably $—(OC_2F_4—OC_3F_6)_g—$ or $—(OC_2F_4—OC_4F_8)_g—$.

In yet another embodiment, PE is a group represented by $—(OC_6F_{12})_a—(OC_5F_{10})_b—(OC_4F_8)_c—(OC_3F_6)_d—(OC_2F_4)_e—(OCF_2)_f—$ wherein e is an integer of 1 or more and 200 or less, a, b, c, d, and f are each independently an integer of 0 or more and 200 or less, the sum of a, b, c, d, e, and f is at least 1, and the occurrence order of the respective repeating units enclosed in parentheses provided with a, b, c, d, e, or f is not limited in the formula. e is preferably an integer of 1 or more and 100 or less, and more preferably 5 or more and 100 or less. The sum of a, b, c, d, e, and f is preferably 5 or more, and more preferably 10 or more, for example, 10 or more and 100 or less.

In yet another embodiment, PE is a group represented by $—(OC_6F_{12})_a—(OC_5F_{10})_b—(OC_4F_8)_c—(OC_3F_6)_d—(OC_2F_4)_e—(OCF_2)_f—$ wherein f is an integer of 1 or more and 200 or less, a, b, c, d, and e are each independently an integer of 0 or more and 200 or less, the sum of a, b, c, d, e, and f is at least 1, and the occurrence order of the respective repeating units enclosed in parentheses provided with a, b, c, d, e, or f is not limited in the formula. f is preferably an integer of 1 or more and 100 or less, and more preferably 5 or more and 100 or less. The sum of a, b, c, d, e, and f is preferably 5 or more, and more preferably 10 or more, such as 10 or more and 100 or less.

The ratio of e to f in PE (hereinafter referred to as an "e/f ratio") is 0.1 or more and 10 or less, preferably 0.2 or more and 5 or less, more preferably 0.2 or more and 2 or less, even more preferably 0.2 or more and 1.5 or less, and further preferably 0.2 or more and 0.85 or less. With an e/f ratio of 10 or less, the lubricity, friction durability, and chemical resistance (such as durability against artificial sweat) of a surface-treating layer obtained from the compound are further increased. The smaller the e/f ratio is, the higher the lubricity and the friction durability of the surface-treating layer are. On the other hand, with an e/f ratio of 0.1 or more, the stability of the compound can be further increased. The larger the e/f ratio is, the higher the stability of the compound is.

In one embodiment, the e/f ratio is 0.2 or more and 0.95 or less, and more preferably 0.2 or more and 0.9 or less.

In one embodiment, the e/f ratio is less than 0.9, preferably 0.8 or less, 0.7 or less, and may be 0.65 or less. The e/f ratio is, for example, 0.2 or more, 0.3 or more, 0.4 or more, 0.5 or more, or 0.55 or more. The e/f ratio may be, for example, 0.2 or more and less than 0.9, specifically 0.4 or more and 0.8 or less, and more specifically 0.5 or more and 0.8 or less. Having such an e/f ratio, the surface-treating agent of the present disclosure can form a surface-treating layer having better lubricity.

In one embodiment, the e/f ratio may be 0.4 or more and 0.7 or less, may be 0.5 or more and 0.7 or less, may be 0.55 or more and 0.7 or less, and may be 0.55 or more and 0.65 or less.

In one embodiment, from the viewpoint of heat resistance, the e/f ratio is preferably 1.0 or more, and more preferably 1.0 or more and 2.0 or less.

In one embodiment, in the above formulae, PE is independently at each occurrence a group represented by $-(OC_6F_{12})_a-(OC_5F_{10})_b-(OC_4F_8)_c-(OC_3F_6)_d-(OC_2F_4)_e-(OCF_2)_f-$ and has at least one branched structure in the polyether group. That is to say, in this embodiment, PE has at least one $CF_3$ terminal (specifically $-CF_3$, $-C_2F_5$, or the like, and more specifically $-CF_3$). In PE, the oxygen atom at the left terminal of the formula binds to the Rf group. Having a polyether group with such a structure, a layer (e.g., a surface-treating layer) formed using the polyether group-containing compound (or a surface-treating agent containing the polyether group-containing compound) may have better UV resistance, water-repellency, oil-repellency, antifouling properties (e.g., preventing from adhering grime such as fingerprints), chemical resistance, hydrolysis resistance, suppressing effect of lubricity, high friction durability, heat resistance, moisture-proof properties, and the like.

In the above formula, a, b, c, d, e, and f are each independently an integer of 0 or more and 200 or less, and the sum of a, b, c, d, e, and f is at least 1. Preferably, a, b, c, d, e, and f are each independently an integer of 0 or more and 100 or less. The sum of a, b, c, d, e, and f is preferably 5 or more, and more preferably 10 or more. The sum of a, b, c, d, e, and f is preferably 200 or less, more preferably 100 or less, such as 10 or more and 200 or less, and more specifically 10 or more and 100 or less. The occurrence order of the respective repeating units enclosed in parentheses provided with a, b, c, d, e, or f is not limited in the formula.

The group represented by PE preferably has at least 5, more preferably 10, and particularly preferably 20 branched structures.

In the structure of the group represented by PE, the number of repeating units having a branched structure is preferably 40 or more, more preferably 60 or more, and particularly preferably 80 or more with respect to the total number of repeating units being 100 (e.g., the sum of a, b, c, d, e, and f). In the structure of the group represented by PE, the number of repeating units having a branched structure, with respect to the total number of repeating units being 100, may be, for example, 100 or less, and may be, for example, 90 or less.

In the structure of the group represented by PE, the number of repeating units having a branched structure is preferably in the range from 40 to 100, more preferably in the range from 60 to 100, and particularly preferably in the range from 80 to 100 with respect to the total number of repeating units being 100.

An example of the branched chain in the branched structure may be $CF_3$.

As for the repeating units having a branched structure, examples of $-(OC_6F_{12})-$ include $-(OCF(CF_3)CF_2CF_2CF_2CF_2)-$, $-(OCF_2CF(CF_3)CF_2CF_2CF_2)-$, $-(OCF_2CF_2CF(CF_3)CF_2CF_2)-$, $-(OCF_2CF_2CF_2CF(CF_3)CF_2)-$, and $-(OCF_2CF_2CF_2CF_2CF(CF_3))-$. Examples of $-(OC_5F_{10})-$ include $-(OCF(CF_3)CF_2CF_2CF_2)-$, $-(OCF_2CF(CF_3)CF_2CF_2)-$, $-(OCF_2CF_2CF(CF_3)CF_2)-$, and $-(OCF_2CF_2CF_2CF(CF_3))-$. Examples of $-(OC_4F_8)-$ include $-(OCF(CF_3)CF_2CF_2)-$, $-(OCF_2CF(CF_3)CF_2)-$, $-(OCF_2CF_2CF(CF_3))-$, $-(OC(CF_3)_2CF_2)-$, $-(OCF_2C(CF_3)_2)-$, $-(OCF(CF_3)CF(CF_3))-$, $-(OCF(C_2F_5)CF_2)-$, and $-(OCF_2CF(C_2F_5))-$. Examples of $-(OC_3F_6)-$ include $-(OCF(CF_3)CF_2)-$ and $-(OCF_2CF(CF_3))-$. Examples of $-(OC_2F_4)-$ include $-(OCF(CF_3))-$.

PE may contain not only a repeating unit having a branched structure, but also a straight repeating unit. Examples of the straight repeating unit include $-(OCF_2CF_2CF_2CF_2CF_2CF_2)-$, $-(OCF_2CF_2CF_2CF_2CF_2)-$, $-(OCF_2CF_2CF_2CF_2)-$, $-(OCF_2CF_2CF_2)-$, and $-(OCF_2CF_2)-$.

Preferably, in the group represented by PE, repeating units $-(OC_6F_{12})-$, $-(OC_5F_{10})-$, $-(OC_4F_8)-$, and $-(OC_3F_6)-$ have a branched structure.

More preferably, PE is composed of repeating units $OC_6F_{12}$, $OC_5F_{10}$, $OC_4F_8$, and $OC_3F_6$ having a branched structure.

In one embodiment, PE is $-(OC_3F_6)_d-$ wherein d is an integer of 1 or more and 200 or less, preferably 5 or more and 200 or less, more preferably 10 or more and 200 or less, and has at least one branched structure.

In this embodiment, the group represented by PE may further contain a straight repeating unit $-(OCF_2CF_2CF_2)-$.

In the above embodiment, PE is preferably composed of a repeating unit $OC_3F_6$ having a branched structure. PE is more preferably represented by formula: $-(OCF_2CF(CF_3))_d-$ wherein d is an integer of 1 or more and 200 or less, preferably 5 or more and 200 or less, and more preferably 10 or more and 200 or less.

In another embodiment, PE is $-(OC_4F_8)_c-(OC_3F_6)_d-(OC_2F_4)_e-(OCF_2)_f-$ wherein c and d are each independently an integer of 0 or more and 30 or less, e and f are each independently an integer of 1 or more and 200 or less, preferably 5 or more and 200 or less, more preferably 10 or more and 200 or less, the sum of c, d, e, and f is at least 5 or more and preferably 10 or more, and the occurrence order of the respective repeating units enclosed in parentheses provided with a subscript c, d, e, or f is not limited in the formula, and the group represented by PE has at least one branched structure.

In yet another embodiment, PE is a group represented by $-(R^6-R^7)_j-$, and the group represented by PE has at least one branched structure, wherein $R^6$ is $OCF_2$ or $OC_2F_4$, and preferably $OC_2F_4$, and $R^7$ is a group selected from $OC_2F_4$, $OC_3F_6$, $OC_4F_8$, $OC_5F_{10}$, and $OC_6F_{12}$, or a combination of two or three groups independently selected from these groups. Preferably, $R^7$ is a group selected from $OC_2F_4$, $OC_3F_6$, and $OC_4F_8$, a group selected from $OC_3F_6$, $OC_4F_8$, $OC_5F_{10}$, and $OC_6F_{12}$, or a combination of two or three groups independently selected from these groups. Examples of the combination of 2 or 3 groups independently selected from $OC_2F_4$, $OC_3F_6$, and $OC_4F_8$ include, but are not limited to, $-OC_2F_4OC_3F_6-$, $-OC_2F_4OC_4F_8-$, $-OC_3F_6OC_2F_4-$, $-OC_3F_6OC_3F_6-$, $-OC_3F_6OC_4F_8-$, —OC$_4$F$_8$OC$_4$F$_8$—, —OC$_4$F$_8$OC$_3$F$_6$—, —OC$_4$F$_8$OC$_2$F$_4$—, —OC$_2$F$_4$OC$_2$F$_4$OC$_3$F$_6$—, —OC$_2$F$_4$OC$_2$F$_4$OC$_4$F$_8$—, —OC$_2$F$_4$OC$_3$F$_6$OC$_2$F$_4$—, —OC$_2$F$_4$OC$_3$F$_6$OC$_3$F$_6$—, —OC$_2$F$_4$OC$_4$F$_8$OC$_2$F$_4$—, —OC$_3$F$_6$OC$_2$F$_4$OC$_2$F$_4$—, —OC$_3$F$_6$OC$_2$F$_4$OC$_3$F$_6$—, —OC$_3$F$_6$OC$_3$F$_6$OC$_2$F$_4$—, and —OC$_4$F$_8$OC$_2$F$_4$OC$_2$F$_4$—. j is an integer of 2 or more, preferably 3 or more and more preferably 5 or more, and 100 or less and preferably 50 or less. In the above formula, OC$_2$F$_4$, OC$_3$F$_6$, OC$_4$F$_8$, OC$_5$F$_{10}$, and OC$_6$F$_{12}$ preferably have a branched structure.

In the above embodiment, PE is more preferably composed of repeating units OC$_6$F$_{12}$, OC$_5$F$_{10}$, OC$_4$F$_8$, and OC$_3$F$_6$ having a branched structure.

In yet another embodiment, PE is a group represented by —(OC$_6$F$_{12}$)$_a$—(OC$_5$F$_{10}$)$_b$—(OC$_4$F$_8$)$_c$—(OC$_3$F$_6$)$_d$—(OC$_2$F$_4$)$_e$—(OCF$_2$)$_f$—, and the group represented by PE has at least one branched structure, wherein e is an integer of 1 or more and 200 or less, a, b, c, d, and f are each independently an integer of 0 or more and 200 or less, the sum of a, b, c, d, e, and f is at least 1, and the occurrence order of the respective repeating units enclosed in parentheses provided with a, b, c, d, e, or f is not limited in the formula. e is preferably an integer of 1 or more and 100 or less, and more preferably 5 or more and 100 or less. The sum of a, b, c, d, e, and f is preferably 5 or more, and more preferably 10 or more such as 10 or more and 100 or less.

In yet another embodiment, PE is a group represented by —(OC$_6$F$_{12}$)$_a$—(OC$_5$F$_{10}$)$_b$—(OC$_4$F$_8$)$_c$—(OC$_3$F$_6$)$_d$—(OC$_2$F$_4$)$_e$—(OCF$_2$)$_f$—, and the group represented by PE has at least one branched structure, wherein f is an integer of 1 or more and 200 or less, a, b, c, d, and e are each independently an integer of 0 or more and 200 or less, the sum of a, b, c, d, e, and f is at least 1, and the occurrence order of the respective repeating units enclosed in parentheses provided with a, b, c, d, e, or f is not limited in the formula. f is preferably an integer of 1 or more and 100 or less, and more preferably 5 or more and 100 or less. The sum of a, b, c, d, e, and f is preferably 5 or more, and more preferably 10 or more, such as 10 or more and 100 or less.

In the polyether-group containing compound, the number average molecular weight of the -PE- moiety is not limited, and is, for example, 500 to 30,000, preferably 1,500 to 30,000, and more preferably 2,000 to 10,000. The number average molecular weight is a value obtained by 19F-NMR measurement.

In another embodiment, the number average molecular weight of the -PE- moiety may be 500 to 30,000, preferably 1,000 to 20,000, more preferably 2,000 to 15,000, and even more preferably 2,000 to 10,000, such as 3,000 to 6,000.

In another embodiment, the number average molecular weight of the -PE- moiety may be 4,000 to 30,000, preferably 5,000 to 10,000, and more preferably 6,000 to 10,000.

α is an integer of 1 to 9. α may vary according to the valence of X$^1$. For example, when X$^1$ is a decavalent organic group, a is 9. When X$^1$ is a single bond, a is 1.

X$^1$ is interpreted as a linker that connects a triazine ring and a fluorine-containing polyether moiety (a polyether group moiety represented by PE) that mainly provides water-repellency, surface lubricity, and the like. Accordingly, X$^1$ may be a single bond or any organic group as long as the compound represented by formula (I) can stably exist.

X$^{f1}$ is a group represented by (X$^{f11}$)$_z$. The left side of the group of X$^{f1}$ binds to Rf, and the right side of X$^{f1}$ binds to PE.

X$^{f11}$ is an alkylene group having 1 to 6 carbon atoms, preferably an alkylene group having 1 to 3 carbon atoms, and more preferably an alkylene group having 1 to 2 carbon atoms, such as a methylene group.

In X$^{f11}$, a hydrogen atom contained in the alkylene group may be replaced with a fluorine atom. X$^{f11}$ is preferably an alkylene group wherein a hydrogen atom contained in the alkylene group is replaced with a fluorine atom, and is more preferably a perfluoroalkylene group. X$^{f11}$ may be straight or may have a branched chain. Preferably, X$^{f11}$ is straight.

Specific examples of X$^{f11}$ include perfluoroalkylene groups such as —CF$_2$—, —C$_2$F$_4$—, —C$_3$F$_6$—, —C$_4$F$_8$—, —C$_5$F$_{10}$—, and —C$_6$F$_{12}$—; and fluoroalkylene groups obtained by some hydrogen atoms are substituted with fluorine atoms, such as —CHF—.

—(C$_6$F$_{12}$)— may be —CF$_2$CF$_2$CF$_2$CF$_2$CF$_2$CF$_2$—, —CF(CF$_3$)CF$_2$CF$_2$CF$_2$CF$_2$—, —CF$_2$CF(CF$_3$)CF$_2$CF$_2$CF$_2$—, —CF$_2$CF$_2$CF(CF$_3$)CF$_2$CF$_2$—, —CF$_2$CF$_2$CF$_2$CF(CF$_3$)CF$_2$—, —CF$_2$CF$_2$CF$_2$CF$_2$CF(CF$_3$)—, or the like, and is preferably —CF$_2$CF$_2$CF$_2$CF$_2$CF$_2$CF$_2$—. —C$_5$F$_{10}$— may be —CF$_2$CF$_2$CF$_2$CF$_2$CF$_2$—, —CF(CF$_3$)CF$_2$CF$_2$CF$_2$—, —CF$_2$CF(CF$_3$)CF$_2$CF$_2$—, —CF$_2$CF$_2$CF(CF$_3$)CF$_2$—, —CF$_2$CF$_2$CF$_2$CF(CF$_3$)—, or the like, and is preferably —CF$_2$CF$_2$CF$_2$CF$_2$CF$_2$—. —C$_4$F$_8$— may be any of —CF$_2$CF$_2$CF$_2$CF$_2$—, —CF(CF$_3$)CF$_2$CF$_2$—, —CF$_2$CF(CF$_3$)CF$_2$—, —CF$_2$CF$_2$CF(CF$_3$)—, —C(CF$_3$)$_2$CF$_2$—, —CF$_2$C(CF$_3$)$_2$—, —CF(CF$_3$)CF(CF$_3$)—, —CF(C$_2$F$_5$)CF$_2$—, and —CF$_2$CF(C$_2$F$_5$)—, and is preferably —CF$_2$CF$_2$CF$_2$CF$_2$—. —C$_3$F$_6$— may be any of —CF$_2$CF$_2$CF$_2$—, —CF(CF$_3$)CF$_2$—, and —CF$_2$CF(CF$_3$)—, and is preferably —CF$_2$CF$_2$CF$_2$—. —C$_2$F$_4$— may be any of —CF$_2$CF$_2$— and —CF(CF$_3$)—.

X$^{f1}$ is more preferably —CF$_2$—, —CF$_2$CF$_2$—, or —CF(CF$_3$)—, even more preferably —CF$_2$— or —CF$_2$CF$_2$—, and particularly preferably —CF$_2$—.

X$^{f2}$ is a group represented by (O)$_y$ or (NH)$_y$, and preferably a group represented by (O)$_y$.

z is each independently at each occurrence 0 or 1, and y is each independently at each occurrence 0 or 1. Specifically, z is 0, and y is 0; z is 0, and y is 1; z is 1, and y is 0; and z is 1, and y is 1.

Preferably, the sum of z and y is 0 or 1.

When y is 0, the group represented by X$^{f2}$ is a single bond; and when z is 0, the group represented by X$^{f1}$ is a single bond.

X$^1$ is each independently at each occurrence a single bond, an oxygen atom, a nitrogen atom, a sulfur atom, —NH—, —SO$_2$NH—, —SO$_2$—, or a di- to decavalent organic group.

In one embodiment, X$^1$ is a nitrogen atom. In this embodiment, the group represented by (Rf-X$^{f1}$-PE-X$^{f2}$)$_\alpha$—X$^1$— is represented by (Rf-X$^{f1}$-PE-X$^{f2}$)$_2$—N—.

In one embodiment, X$^1$ is a di- to decavalent organic group.

X$^1$ is preferably a di- to heptavalent, more preferably a di- to tetravalent, and even more preferably a di to trivalent organic group.

In one embodiment, X$^1$ may be a tri- to decavalent organic group, and α is 2 to 9.

In one embodiment, X$^1$ is a divalent organic group, and α is 1.

In one embodiment, X$^1$ is each independently at each occurrence a divalent organic group, and the divalent organic group is —CONH—, —NHCO—, —NHCONH—, —OCONH—, or —NHCOO—.

In one embodiment, X$^1$ is each independently at each occurrence a trivalent or divalent organic group represented by (—(R$^{11}$)$_{n16}$—)$_2$N—(R$^{12}$)$_{n17}$—, —(R$^{11}$)$_{n16}$—X$^{11}$—(R$^{12}$)$_{n17}$—, or —R$^{13}$—.

For example, when $X^1$ is represented by $(-(R^{11})_{n16}-)_2N-(R^{12})_{n17}-$, the group represented by $(Rf-X^{f1}-PE-X^{f2})_\alpha-X^1-$ is represented by $(Rf-X^{f1}-PE-X^{f2}-(R^{11})_{n16}-)_2N-(R^{12})_{n17}-$; when $X^1$ is represented by $-(R^{11})_{n16}-X^{11}-(R^{12})_{n17}-$, the group represented by $(Rf-X^{f1}-PE-X^{f2})_\alpha-X^1-$ is represented by $Rf-X^{f1}-PE-X^{f2}-(R^{11})_{n16}-X^{11}-(R^{12})_{n17}-$; and when $X^1$ is represented by $-R^{13}-$, the group represented by $(Rf-X^{f1}-PE-X^{f2})_\alpha-X^1-$ is represented by $Rf-X^{f1}-PE-X^{f2}-R^{13}-$.

$X^1$ is preferably a group represented by $(-(R^{11})_{n16}-)_2N-(R^{12})_{n17}-$ or $-(R^{11})_{n16}-X^{11}-(R^{12})_{n17}-$, and more preferably a group represented by $-(R^{11})_{n16}-X^{11}-(R^{12})_{n17}-$.

$R^{11}$ is a group or a bond that binds to the polyether group (the group represented by PE) side. Herein, the left side of the structure denoted as $R^{11}$ binds to the group enclosed in parentheses provided with $\alpha$.

$R^{11}$ each independently at each occurrence represents $-(CH_2)_{n11}-$, an o-, m-, or p-phenylene group, which may be substituted with one or more fluorine atoms, and is preferably $-(CH_2)_{n11}-$ optionally substituted with one or more fluorine atoms, and more preferably $-(CH_2)_{n11}-$ not substituted with fluorine atoms, wherein n11 is an integer of 1 to 20, preferably an integer of 1 to 6, more preferably an integer of 1 to 3, and even more preferably 1 or 2.

$R^{12}$ is a group or a bond that binds to the triazine ring. Herein, the right side of the structure denoted as $R^{12}$ binds to the triazine ring.

$R^{12}$ each independently at each occurrence represents $-(CH_2)_{n12}-$, an o-, m-, or p-phenylene group, which may be substituted with one or more fluorine atoms, and is preferably $-(CH_2)_{n12}-$ optionally substituted with one or more fluorine atoms, and more preferably $-(CH_2)_{n12}-$ not substituted with fluorine atoms, wherein n12 is an integer of 1 to 20, preferably an integer of 1 to 6, more preferably an integer of 1 to 3, and even more preferably 1.

n16 is each independently at each occurrence 0 or 1, and n17 is each independently at each occurrence 0 or 1. The sum of n16 and n17 is preferably 1 or more. Preferably n16 is 0 and n17 is 1, or n16 is 1 and n17 is 0, and more preferably n16 is 1 and n17 is 0.

$X^{11}$ is each independently at each occurrence $-O-$, $-(OR^{61})_{n14}-$, $-S-$, $-C(=O)-$, $-C(=O)$ $O-$, $-O-C(=O)-$, $-O-C(=O)-O-$, $-Si(R^{62})_2-$, $-(Si(R^{62})_2O)_{n15}-Si(R^{62})_2-$, $-NR^3C(=O)-$, $-C(=O)NR^3-$, $-NR^3C(=O)NR^3-$, $-NR^3C(=O)O-$, $-O-C(=O)NR^3-$, $-NR^3-$, $-SO_2NR^3-$, or $-SO_2-$.

$X^{11}$ is preferably a group represented by $-O-$, $-S-$, $-C(=O)NR^3-$, $-NR^3C(=O)O-$, or $-NR^3-$, and more preferably a group represented by $-O-$ or $-NR^3-$ (e.g., $-NH-$).

Herein, the left side of the structure of $X^{11}$ binds to the group represented by $R^{11}$, and the right side of $X^{11}$ binds to the group represented by $R^{12}$.

$R^3$ is each independently at each occurrence a hydrogen atom, a phenyl group, or an alkyl group having 1 to 6 carbon atoms (preferably a methyl group), preferably a hydrogen atom or a methyl group, and more preferably a hydrogen atom.

For example, when $R^3$ is a hydrogen atom, $-NR^3C(=O)-$, $-C(=O)NR^3-$, $-NR^3C(=O)NR^3-$, $-NR^3C(=O)O-$, or $-O-C(=O)NR^3-$ among those listed as $X^{11}$ is $-NHCO-$, $-CONH-$, $-NHCONH-$, $-NHCOO-$, or $-OCONH-$, respectively.

$R^{61}$ is each independently at each occurrence a $C_{1-6}$ alkylene group, and preferably a $C_{1-3}$ alkylene group.

$R^{62}$ each independently at each occurrence represents a phenyl group, a $C_{1-6}$ alkyl group, or a $C_{1-6}$ alkoxy group, preferably a phenyl group or a $C_{1-6}$ alkyl group, and more preferably a methyl group.

n14 is each independently at each occurrence an integer of 1 to 5, preferably an integer of 1 to 3, and more preferably 1.

n15 is each independently at each occurrence an integer of 1 to 100, and preferably an integer of 1 to 20.

Here, $X^{11}$ may be substituted with one or more substituents selected from a fluorine atom, a $C_{1-3}$ alkyl group, and a $C_{1-3}$ fluoroalkyl group.

Preferably, $R^{13}$ is each independently at each occurrence $-(CH_2)_{n13}-$ wherein n13 is an integer of 1 to 20, preferably an integer of 1 to 6, and more preferably an integer of 1 to 3.

In a preferable embodiment, $X^1$ is a group represented by $-(R^{11})_{n16}-X^{11}-(R^{12})_{n17}-$, n16 is 1, and n17 is 0. $X^{11}$ is preferably $-O-$ or $-NH-$, and preferably, $R^{11}$ is $-(CH_2)_{n11}-$ and n11 is an integer of 1 to 3. n11 is more preferably 1 or 2.

Specific examples of $X^1$ include:
a single bond,
$-O-$,
$-(CH_2)-O-$,
$-(CH_2)_2-O-$,
$-(CH_2)_3-O-$,
$-(CH_2)_4-O-$,
$-CF_2CH_2-O-$,
$-CF_2(CH_2)_2-O-$,
$-CF_2(CH_2)_3-O-$,
$-CF_2(CH_2)_4-O-$,
$-C(=O)-$,
$-CH_2-C(=O)-$,
$-C(=O)O-$,
$-CH_2-C(=O)O-$,
$-OC(=O)-$,
$-CH_2-OC(=O)-$,
$-C(=O)NH-$,
$-CH_2-C(=O)NH-$,
$-NHC(=O)-$,
$-NHCH_2-C(=O)-$,
$-NCH_3C(=O)-$,
$-CH_2-NCH_3C(=O)-$,
$-CF_2C(=O)NH-$,
$-CF_2CH_2-C(=O)NH-$,
$-CF_2NHC(=O)-$,
$-CF_2NHCH_2-C(=O)-$,
$-CF_2NCH_3C(=O)-$,
$-CF_2CH_2-NCH_3C(=O)-$,
$-NH-$,
$-CH_2-NH-$,
$-(CH_2)_2-NH-$,
$-(CH_2)_3-NH-$,
$-(CH_2)_4-NH-$,
$-CF_2-NH-$,
$-CF_2CH_2-NH-$,
$-CF_2(CH_2)_2-NH-$,
$-CF_2(CH_2)_3-NH-$,
$-CF_2(CH_2)_4-NH-$,
$-NCH_3-$,
$-CH_2-NCH_3-$,
$-(CH_2)_2-NCH_3-$,
$-(CH_2)_3-NCH_3-$,
$-(CH_2)_4-NH-$, —CH$_2$—,
—(CH$_2$)$_2$—,
—(CH$_2$)$_3$—,
—(CH$_2$)$_4$—,
—(CH$_2$)$_5$—,
—(CH$_2$)$_6$—,
—CF$_2$CH$_2$—,
—CF$_2$(CH$_2$)$_2$—,
—CF$_2$(CH$_2$)$_3$—,
—CF$_2$(CH$_2$)$_4$—,
—CF$_2$(CH$_2$)$_5$—,
—CF$_2$(CH$_2$)$_6$—,
—S—,
—CH$_2$—S—,
—(CH$_2$)$_2$—S—,
—(CH$_2$)$_3$—S—,
—SO$_2$NH—,
—SO$_2$NCH$_3$—,
—SO$_2$—,
—NHC(=O)—O—,
—CH$_2$NHC(=O)O—,
—CH$_2$OC(=O)NH—,
—O—C(=O)NH—,
—NHC(=O)NH—, and
—CH$_2$NHC(=O)NH—, provided that, herein, the left side of the structure of X$^1$ binds to the group enclosed in parentheses provided with α, and the right side of X$^1$ binds to the triazine ring.

[Group represented by R$^{Si}$—]

The polyether group-containing compound of the present disclosure has a group represented by R$^{Si}$—. The group represented by R$^{Si}$— is each independently at each occurrence a group represented by any of formulae (A1) to (A4) having a Si atom at a terminal, wherein the Si atom is binding to a hydroxyl group or a hydrolyzable group. Having such a group, the compound of the present disclosure can contribute to formation of a surface-treating layer having good adhesion to a base material. Formulae (A1) to (A4):

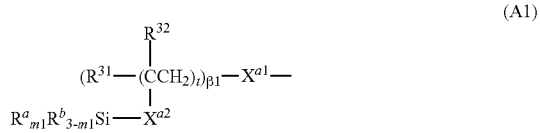

(A1)

$(R^a{}_m R^b{}_{3-m} Si)_{\beta 2}$—X$^{a3}$— (A2)

(A3)

(A4)

Formula (A1) will now be described below.

β1 is an integer of 1 to 9. β1 may vary according to the valence of X$^{a1}$. For example, when X$^{a1}$ is a decavalent organic group, β1 is 9. When X$^{a1}$ is a single bond, β1 is 1.

X$^{a1}$ represents a single bond, an oxygen atom, a nitrogen atom, a sulfur atom, —NH—, —SO$_2$NH—, —SO$_2$—, or a di- to decavalent organic group. X$^{a1}$ is preferably a di- to heptavalent, more preferably a di- to tetravalent, and even more preferably a divalent or trivalent organic group, and may be a divalent organic group. Herein, the right side of the structure denoted as X$^{a1}$ binds to the triazine ring.

In one embodiment, X$^{a1}$ is a divalent organic group, and the divalent organic group is —CONH—, —NHCO—, —NHCONH—, —OCONH—, or —NHCOO—.

Preferably, X$^{a1}$ is a trivalent or divalent organic group represented by $(-(R^{71})_{n21}-)_2 N-(R^{72})_{n22}-$, $-(R^{71})_{n21}-X^3-(R^{72})_{n22}-$, —R$^{73}$—, or —Y—O—.

For example, when X$^{a1}$ is represented by $(-(R^{71})_{n21}-)_2 N-(R^{72})_{n22}-$, R$^{71}$ connects the group enclosed in parentheses provided with β1 in formula (A1) and the nitrogen atom contained in X$^{a1}$, and R$^{72}$ connects the nitrogen atom contained in X$^{a1}$ and the triazine ring in formula (I). When X$^{a1}$ is represented by $-(R^{71})_{n21}-X^3-(R^{72})_{n22}-$, R$^{71}$ connects the group enclosed in parentheses provided with β1 in formula (A1) and the group represented by X$^3$, and R$^{72}$ connects the group represented by X$^3$ and the triazine ring in formula (I). When X$^{a1}$ is represented by —R$^{73}$—, R$^{73}$ connects the group enclosed in parentheses provided with β1 in formula (A1) and the triazine ring in formula (I). When X$^{a1}$ is represented by —Y—O—, O connects Y and the triazine ring.

X$^{a1}$ is preferably a group represented by $(-(R^{71})_{n21}-)_2 N-(R^{72})_{n22}-$ or $-(R^{71})_{n21}-X^3-(R^{72})_{n22}-$, and more preferably a group represented by $-(R^{71})_{n21}-X^3-(R^{72})_{n22}-$.

R$^{71}$ each independently at each occurrence represents —(CH$_2$)$_{n23}$—, an o-, m-, or p-phenylene group, which may be substituted with one or more fluorine atoms, and is preferably —(CH$_2$)$_{n23}$— optionally substituted with one or more fluorine atoms, and more preferably —(CH$_2$)$_{n23}$— not substituted with fluorine atoms, wherein n23 is each independently at each occurrence an integer of 1 to 20, preferably an integer of 1 to 6, more preferably an integer of 1 to 3, and even more preferably 1 or 2. Herein, the left side of the structure of R$^{71}$ binds to the group enclosed in parentheses provided with β1.

R$^{72}$ is a group or a bond that binds to the triazine ring. Herein, the right side of the structure of R$^{72}$ binds to the triazine ring.

R$^{72}$ each independently at each occurrence represents —(CH$_2$)$_{n24}$—, an o-, m-, or p-phenylene group, which may be substituted with one or more fluorine atoms, and is preferably —(CH$_2$)$_{n24}$— optionally substituted with one or more fluorine atoms, and more preferably —(CH$_2$)$_{n24}$— not substituted with fluorine atoms.

n24 is each independently at each occurrence an integer of 1 to 20, preferably an integer of 1 to 6, more preferably an integer of 1 to 3, and even more preferably 1 or 2.

n21 is 0 or 1, and n22 is 0 or 1. The sum of n21 and n22 is preferably 1 or more. Preferably n21 is 0 and n22 is 1, or n21 is 1 and n22 is 0, and more preferably n21 is 1 and n22 is 0.

X$^3$ is —O—, —(OR$^{74}$)$_{n25}$—, —S—, —C(=O)—, —C(=O) O—, —O—C(=O)—, —O—C(=O)O—, —Si(R$^{75}$)$_2$—, —(Si(R$^{75}$)$_2$O)$_{n26}$—Si(R$^{75}$)$_2$—, —NR$^3$C (=O)—, —C(=O)NR$^3$—, —NR$^3$C(=O)NR$^3$—, —NR$^3$C (=O)O—, —O—C(=O)NR$^3$—, —NR$^3$—, —SO$_2$NR$^3$—, or —SO$_2$—.

X$^3$ is preferably a group represented by —O—, —S—, —NHC(=O)O—, —O(C=O)NH—, or —NR$^3$—, and more preferably a group represented by —O— or —NR$^3$— (e.g., —NH—).

Herein, the left side of the structure of X$^3$ binds to the group represented by R$^{71}$, and the right side of X$^3$ binds to the group represented by R$^{72}$.

$R^3$ is a hydrogen atom, a phenyl group, or an alkyl group having 1 to 6 carbon atoms (preferably a methyl group), and preferably a hydrogen atom or a methyl group, and more preferably a hydrogen atom.

$R^{74}$ is each independently at each occurrence a $C_{1-6}$ alkylene group and preferably a $C_{1-3}$ alkylene group.

$R^{75}$ each independently at each occurrence represents a phenyl group, a $C_{1-6}$ alkyl group, or a $C_{1-6}$ alkoxy group, and is preferably a phenyl group or a $C_{1-6}$ alkyl group, and more preferably a methyl group.

n25 is each independently at each occurrence an integer of 1 to 5, preferably an integer of 1 to 3, and more preferably 1.

n26 is each independently at each occurrence an integer of 1 to 100 and preferably an integer of 1 to 20.

A hydrogen atom of $X^3$ may be replaced with one or more substituents selected from a fluorine atom, a $C_{1-3}$ alkyl group, and a $C_{1-3}$ fluoroalkyl group.

Preferably, $R^{73}$ is each independently at each occurrence —$(CH_2)_{n27}$— wherein n27 is an integer of 1 to 20, preferably an integer of 1 to 6, and more preferably an integer of 1 to 3.

Y is a di- to hexavalent, preferably a di- to tetravalent, and more preferably a divalent organic group that binds an oxygen atom and a Si atom, and may have a silicon atom and/or a siloxane bond. Preferably, Y has a silicon atom and/or a siloxane bond.

Specific examples of Y include an alkylene group having 2 to 10 carbon atoms such as an ethylene group, a propylene group (a trimethylene group, a methylethylene group), a butylene group (a tetramethylene group, a methylpropylene group), or a hexamethylene group, an alkylene group having 2 to 8 carbon atoms containing an arylene group having 6 to 8 carbon atoms such as a phenylene group (e.g., an alkylene-arylene group having 8 to 16 carbon atoms), an alkylene group having 2 to 6 carbon atoms containing a diorganosylylene group such as a dimethylsilylene group or a diethylsilylene group, a divalent group in which alkylene groups having 2 to 8 carbon atoms bind to each other via a silalkylene structure having 1 to 4 carbon atoms or a silarylene structure having 6 to 10 carbon atoms, an alkylene group having 2 to 6 carbon atoms containing a linear, branched or cyclic di- to hexavalent organopolysiloxane residue having 2 to 10 and preferably 2 to 5 silicon atoms, and a di- to hexavalent group in which an alkylene group having 2 to 10 carbon atoms binds to a bond of a linear, branched or cyclic di- to hexavalent organopolysiloxane residue having 2 to 10 and preferably 2 to 5 silicon atoms; an alkylene group having 3 to 10 carbon atoms, an alkylene group having 2 to 6 carbon atoms containing a phenylene group, an alkylene group having 2 to 6 carbon atoms containing a dimethylsilylene group, a divalent group in which alkylene groups having 2 to 4 carbon atoms bind to each other via a silalkylene structure having 1 to 4 carbon atoms or a silarylene structure having 6 to 10 carbon atoms, an alkylene group having 2 to 6 carbon atoms containing a linear divalent organopolysiloxane residue having 2 to 10 silicon atoms, and a di- to tetravalent group in which an alkylene group having 2 to 10 carbon atoms binds to a bond of a di- to tetravalent organopolysiloxane residue that is linear and has 2 to 10 silicon atoms or that is branched or cyclic and has 3 to 10 silicon atoms are preferable; and an alkylene group having 3 to 6 carbon atoms is more preferable.

Specific examples of the structure of Y include the following structures. In the following exemplary divalent groups, the left side of the structure denoted as Y binds to the "O" atom contained in the group represented by —Y—O—; and in a group having two or more bonds, at least one bond binds to the group enclosed in parentheses provided with β1, and at least one bond binds to the "O" atom contained in the group represented by —Y—O—.

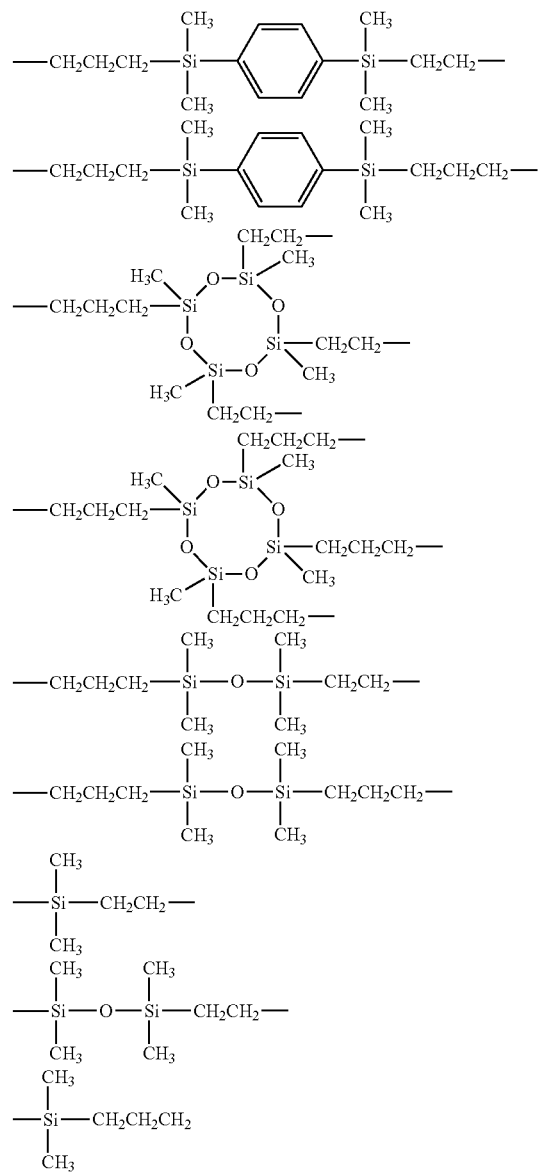

$X^{a1}$ is each independently at each occurrence preferably a group represented by —$(R^{71})_{n21}$—$X^3$—$(R^{72})_{n22}$— or —$R^{73}$—, and more preferably a group represented by —$(R^{71})_{n21}$—$X^3$—$(R^{72})_{n22}$—. Preferably, n21 is 1, n22 is 0, $R^{71}$ is —$(CH_2)_{n23}$— (n23 is an integer of 1 to 6, more preferably an integer of 1 to 3, and even more preferably 1 or 2), $X^3$ is —O— or —$NR^3$— (e.g., —NH—), and $R^{73}$ is —$(CH_2)_{n27}$— (n27 is an integer of 1 to 6, and preferably an integer of 1 to 3).

Specific examples of $X^{a1}$ include:
a single bond,
—O—,
—$(CH_2)$—O—,
—$(CH_2)_2$—O—, —(CH$_2$)$_3$—O—,
—(CH$_2$)$_4$—O—,
—C(=O)—,
—CH$_2$—C(=O)—,
—C(=O)O—,
—CH$_2$—C(=O)O—,
—OC(=O)—,
—CH$_2$—OC(=O)—,
—C(=O)NH—,
—CH$_2$—C(=O)NH—,
—NHC(=O)—,
—NHCH$_2$—C(=O)—,
—NCH$_3$C(=O)—,
—CH$_2$—NCH$_3$C(=O)—,
—NH—,
—CH$_2$— NH—,
—(CH$_2$)$_2$—NH—,
—(CH$_2$)$_3$—NH—,
—(CH$_3$)$_4$—NH—,
—NCH$_3$—,
—CH$_2$—NCH$_3$—,
—(CH$_2$)$_2$—NCH$_3$—,
—(CH$_3$)$_3$—NCH$_3$—,
—(CH$_2$)$_4$—NH—,
—CH$_2$—,
—(CH$_2$)$_2$—,
—(CH$_2$)$_3$—,
(CH$_2$)$_4$—,
(CH$_2$)$_5$—,
—(CH$_2$)$_6$—,
—S—,
—CH$_2$—S—,
—(CH$_2$)$_2$—S—,
—(CH$_3$)$_3$—S—,
—SO$_2$NH—,
—SONCH$_3$—,
—SO$_2$—,
—NHC(=O)—O—,
—CH$_2$NHC(=O)O—,
—CH$_2$OC(=O)NH—,
—O—C(=O)NH—,
—NHC(=O)NH—, and
—CH$_2$NHC(=O)NH—,
provided that, herein, the left side of the structure of X$^{a1}$ binds to the group enclosed in parentheses provided with β1, and the right side of X$^{a1}$ binds to the triazine ring.

X$^{a2}$ represents a single bond or a divalent organic group. X$^{a2}$ is preferably an alkylene group having 1 to 20 carbon atoms, and more preferably —(CH$_2$)$_u$— wherein u is an integer of 0 to 2.

t is each independently an integer of 2 to 10. In a preferable embodiment, t is an integer of 2 to 6.

R$^{31}$ each independently at each occurrence represents a hydrogen atom or a halogen atom. The halogen atom is preferably an iodine atom, a chlorine atom, or a fluorine atom, and more preferably a fluorine atom.

R$^{32}$ each independently at each occurrence represents a hydrogen atom or a monovalent organic group, and is preferably a hydrogen atom or an alkyl group having 1 to 20 carbon atoms, and more preferably a hydrogen atom or an alkyl group having 1 to 6 carbon atoms (e.g., a methyl group, an ethyl group, a propyl group).

In one embodiment, R$^{32}$ is an alkyl group having 1 to 6 carbon atoms (e.g., a methyl group, an ethyl group, a propyl group).

R$^a$ is each independently at each occurrence a hydroxyl group or a hydrolyzable group. The "hydrolyzable group" has the same definition as above.

R$^b$ each independently at each occurrence represents a hydrogen atom or an alkyl group having 1 to 20 carbon atoms, and is preferably an alkyl group having 1 to 6 carbon atoms, and more preferably a methyl group.

In formula (A1), m1 is independently an integer of 0 to 3 for each (R$^a_{m1}$R$^b_{3-m1}$Si—) unit, provided that in formula (A1), there is at least one R$^a_{m1}$R$^b_{3-m1}$Si— wherein m1 is 1 to 3. That is to say, not all integers m1 are simultaneously 0.

In formula (A1), at least two integers m1 are preferably 1 or more. In other words, in formula (A1), there are at least two R$^a_{m1}$R$^b_{3-m1}$Si— wherein m1 is 1 or more.

In formula (A1), there is at least one R$^a_{m1}$R$^b_{3-m1}$Si— wherein m1 is preferably 2 or 3, and m1 is more preferably 3.

Preferably, in formula (A1), m1 is an integer of 1 to 3, and more preferably 2 or 3.

Even more preferably, in formula (A1), m1 is 3. In other words, in formula (A1), the group represented by R$^a_{m1}$R$^b_{3-m1}$Si— is represented by R$^a_3$Si—.

Formula (A2) will now be described below.

β2 is an integer of 1 to 9. β2 may vary according to the valence of X$^{a3}$. For example, when X$^{a3}$ is a decavalent organic group, β2 is 9. When X$^{a3}$ is a single bond, β2 is 1.

X$^{a3}$ represents a single bond or a di- to decavalent organic group, is preferably a di- to heptavalent, more preferably a di- to tetravalent, and even more preferably a divalent or trivalent organic group, and may be a divalent organic group. Herein, the right side of the structure of X$^{a2}$ binds to the triazine ring.

Examples of X$^{a3}$ include, but are not limited to, those described concerning X$^{a1}$. "Formula (A1)" and "β1" in the description concerning X$^{a1}$ correspond to "formula (A2)" and "β2", respectively.

Particularly preferable X$^{a3}$ may be a group represented by —(R$^{71}$)$_{n21}$—X$^3$—(R$^{72}$)$_{n22}$— or —R$^{73}$—, and a group represented by —(R$^{71}$)$_{n21}$—X$^3$—(R$^{72}$)$_{n22}$— is more preferable. Preferably, n21 is 1, n22 is 0, R$^{71}$ is —(CH$_2$)$_{n23}$— (n23 is an integer of 1 to 6, more preferably an integer of 1 to 3, and even more preferably 1 or 2), X$^3$ is —O— or —NR$^3$— (e.g., —NH—), and R$^{73}$ is —(CH$_2$)$_{n27}$— (n27 is an integer of 1 to 6, and preferably an integer of 1 to 3).

Specific examples of X$^{a3}$ include:
a single bond,
—O—,
—(CH$_2$)—O—,
—(CH$_2$)$_2$—O—,
—(CH$_2$)$_3$—O—,
—(CH$_2$)$_4$—O—,
—C(=O)—,
—CH$_2$—C(=O)—,
—C(=O)O—,
—CH$_2$—C(=O)O—,
—OC(=O)—,
—CH$_2$—OC(=O)—,
—C(=O)NH—,
—CH$_2$—C(=O)NH—,
—NHC(=O)—,
—NHCH$_2$—C(=O)—,
—NCH$_3$C(=O)—,
—CH$_2$—NCH$_3$C(=O)—,
—NH—,
—CH$_2$—NH—,
—(CH$_2$)$_2$—NH—,
—(CH$_2$)$_3$—NH—, —(CH$_2$)$_4$—NH—,
—NCH$_3$—,
—CH$_2$—NCH$_3$—
—(CH$_2$)$_2$—NCH$_3$—,
—(CH$_2$)$_3$— NCH$_3$—,
—(CH$_3$)$_4$—NH—,
—CH$_2$—,
—(CH$_2$)$_2$—,
—(CH$_3$)$_3$—,
—(CH$_2$)$_4$—,
(CH$_2$)$_5$—,
—(CH$_2$)$_6$—,
—S—,
—CH$_2$—S—,
—(CH$_2$)$_2$—S—,
—(CH$_3$)$_3$—S—,
—SO$_2$NH—,
—SO$_2$NCH$_3$—,
—SO$_2$—,
—NHC(=O)—O—,
—CH$_2$NHC(=O)O—,
—CH$_2$OC(=O)NH—,
—O—C(=O)NH—,
—NHC(=O)NH—, and
—CH$_2$NHC(=O)NH—, provided that, herein, the left side of the structure of X$^{a3}$ binds to the group enclosed in parentheses provided with β2, and the right side of X$^{a3}$ binds to the triazine ring.

In formula (A2), m1 is independently an integer of 0 to 3 for each (R$^a_{m1}$R$^b_{3-m1}$Si—) unit, provided that in formula (A2), there is at least one R$^a_{m1}$R$^b_{3-m1}$Si— wherein m1 is 1 to 3.

In formula (A2), m1 is preferably an integer of 1 to 3, and more preferably 2 or 3.

More preferably, in formula (A2), m1 is 3. In other words, the group represented by R$^a_{m1}$R$^b_{3-m1}$Si— is represented by R$^a_3$Si—.

Formula (A3) will now be described below.

β3 is an integer of 1 to 9. β3 may vary according to the valence of X$^{a4}$. For example, when X$^{a4}$ is a decavalent organic group, β3 is 9. When X$^{a4}$ is a single bond, β3 is 1.

X$^{a4}$ represents a single bond or a di- to decavalent organic group, is preferably a di- to heptavalent, more preferably a di- to tetravalent, and even more preferably a divalent or trivalent organic group, and may be a divalent organic group. Herein, the right side of the structure of X$^{a4}$ binds to the triazine ring.

Examples of X$^{a4}$ include, but are not limited to, those described concerning X$^{a1}$. "Formula (A1)" and "β1" in the description concerning X$^{a1}$ correspond to "formula (A3)" and "β3", respectively.

Particularly preferable X$^{a4}$ may be a group represented by —(R$^{71}$)$_{n21}$—X$^3$—(R$^{72}$)$_{n22}$— or —R$^{73}$—, and a group represented by —(R$^{71}$)$_{n21}$—X$^3$—(R$^{72}$)$_{n22}$— is more preferable. Preferably, n21 is 1, n22 is 0, R$^{71}$ is —(CH$_2$)$_{n23}$— (n23 is an integer of 1 to 6, more preferably an integer of 1 to 3, and even more preferably 1 or 2), X$^3$ is —O— or —NR$^3$— (e.g., —NH—), and R$^{73}$ is —(CH$_2$)$_{n27}$— (n27 is an integer of 1 to 6, and preferably an integer of 1 to 3).

Specific examples of X$^{a4}$ include:
a single bond,
—O—,
—(CH$_2$)—O—,
—(CH$_3$)$_2$—O—,
—(CH$_2$)$_3$—O—,
—(CH$_2$)$_4$—O—,
—C(=O)—,
—CH$_2$—C(=O)—,
—C(=O)O—,
—CH$_2$—C(=O)O—,
—OC(=O)—,
—CH$_2$—OC(=O)—,
—C(=O)NH—,
—CH$_2$—C(=O)NH—,
—NHC(=O)—,
—NHCH$_2$—C(=O)—,
—NCH$_3$C(=O)—,
—CH$_2$— NCH$_3$C(=O)—,
—NH—,
—CH$_2$— NH—,
—(CH$_3$)$_2$—NH—,
—(CH$_3$)$_3$—NH—,
—(CH$_2$)$_4$—NH—,
—NCH$_3$—,
—CH$_2$—NCH$_3$—,
—(CH$_2$)$_2$—NCH$_3$—,
—(CH$_2$)$_3$—NCH$_3$—,
—(CH$_2$)$_4$—NH—,
—CH$_2$—,
—(CH$_2$)$_2$—,
—(CH$_2$)$_3$—,
—(CH$_2$)$_4$—,
—(CH$_2$)$_5$—,
—(CH$_2$)$_6$—,
—S—,
—CH$_2$—S—,
—(CH$_2$)$_2$—S—,
—(CH$_2$)$_3$—S—,
—SO$_2$NH—,
—SO$_2$NCH$_3$—,
—SO$_2$—,
—NHC(=O)—O—,
—CH$_2$NHC(=O)O—,
—CH$_2$OC(=O)NH—,
—O—C(=O)NH—,
—NHC(=O)NH—, and
—CH$_2$NHC(=O)NH—, provided that, herein, the left side of the structure of X$^{a4}$ binds to the group enclosed in parentheses provided with β3, and the right side of X$^a$ binds to the triazine ring.

R$^{f1}$ each independently at each occurrence represents R$^{41}_{r1}$R$^{42}_{r2}$R$^{43}_{r3}$Si—Z$^1$—.

Z$^1$ each independently at each occurrence represents an oxygen atom or a divalent organic group. The left side of the structure of Z$^1$ binds to the "Si" atom contained in the group represented by R$^{41}_{r1}$R$^{42}_{r2}$R$^{43}_{r3}$Si—Z$^1$—.

Z$^1$ is preferably a divalent organic group, and excludes a group that forms a siloxane bond with the Si atom at the terminal of the molecular backbone (the Si atom to which R$^{f1}$ binds) in formula (A3).

Z$^1$ is preferably a C$_{1-6}$ alkylene group, —(CH$_2$)$_{111}$—O—(CH$_2$)$_{112}$— (wherein 111 is an integer of 0 to 6, for example, an integer of 1 to 6, and 112 is an integer of 0 to 6, for example, an integer of 1 to 6) or -phenylene-(CH$_2$)$_{113}$— (wherein 113 is an integer of 0 to 6), and more preferably a C$_{1-3}$ alkylene group. These groups may be substituted with one or more substituents selected from, for example, a fluorine atom, a C$_{1-6}$ alkyl group, a C$_{2-6}$ alkenyl group, and a C$_{2-6}$ alkynyl group.

In one embodiment, Z$^1$ may be a C$_{1-6}$ alkylene group or -phenylene-(CH$_2$)$_{13}$—. When Z$^1$ is the above group, light resistance, in particular UV resistance, can be more increased. In the formula, 13 is an integer of 0 to 6.

In the above embodiment, $Z^1$ is preferably a $C_{1-6}$ alkylene group, and more preferably a $C_{1-3}$ alkylene group.

$R^{41}$ each independently at each occurrence represents $R^{f1'}$. $R^{f1'}$ has the same definition as $R^{f1}$.

In $R^{f1}$, the number of Si atoms linearly connected via the group $Z^1$ is up to 5. That is to say, in $R^{f1}$, when there is at least one $R^{41}$, there are 2 or more Si atoms linearly connected via the group $Z^1$ in $R^{f1}$, and the number of Si atoms linearly connected via the group $Z^1$ is up to 5. "The number of Si atoms linearly connected via the group $Z^1$ in $R^{f1}$" is equal to the number of repeats of —$Z^1$—Si— linearly connected with each other in $R^{f1}$.

One example where Si atoms are connected via the group $Z^1$ in $R^{f1}$ is shown below:

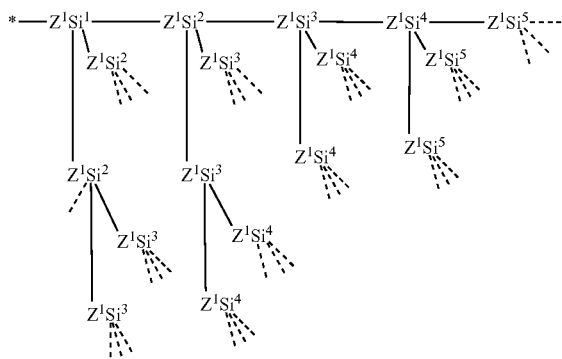

In the above formula, "*" means a portion that binds to the Si atom of the main chain, and " . . . " means that a predetermined group excluding $Z^1$Si binds, or that is to say, when three bonds of a Si atom all have " . . . ", the repetition of $Z^1$Si terminates there. The superscripted number on Si means the number of Si atoms appearing and linearly connected via the group $Z^1$ as counted from "*". That is to say, a chain where the repetition of $Z^1$Si terminates at $Si^2$ is a chain where the "number of Si atoms linearly connected via the group $Z^1$ in $R^{a}$" is 2, and, likewise, chains where the repetition of $Z^1$Si is completed at $Si^3$, $Si^4$, and $Si^5$ mean chains where the "number of Si atoms linearly connected via the group $Z^1$ in $R^{a}$" is 3, 4, and 5, respectively. As seen from the formula, while there are some $Z^1$Si chains in $R^{a}$, it is not necessary that these chains all have the same length, and the chains may each have arbitrary length.

In a preferable embodiment, as shown below, "the number of Si atoms linearly connected via the group $Z^1$ in $R^{f1}$" is 1 (the left formula) or 2 (the right formula) in all chains.

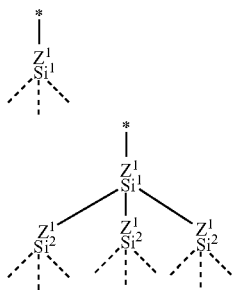

In one embodiment, the number of Si atoms linearly connected via the group $Z^1$ in $R^{f1}$ is 1 or 2 and preferably 1.

$R^{42}$ each independently at each occurrence represents a hydroxyl group or a hydrolyzable group.

$R^{42}$ is preferably a hydrolyzable group and more preferably —$OR^{a1}$ wherein $R^{a1}$ represents a substituted or unsubstituted $C_{1-3}$ alkyl group, and more preferably a methyl group.

$R^{43}$ each independently at each occurrence represents a hydrogen atom or a monovalent organic group, and is preferably a hydrogen atom or an alkyl group having 1 to 20 carbon atoms, and more preferably a hydrogen atom or an alkyl group having 1 to 6 carbon atoms (e.g., a methyl group, an ethyl group, a propyl group).

In one embodiment, $R^{43}$ is an alkyl group having 1 to 6 carbon atoms (e.g., a methyl group, an ethyl group, a propyl group).

r1 is each independently at each occurrence an integer of 0 to 3, r2 is each independently at each occurrence an integer of 0 to 3, and r3 is each independently at each occurrence an integer of 0 to 3, provided that in each $R^{41}_{r1}R^{42}_{r2}R^{43}_{r3}Si$-$Z^1$—, the sum of r1, r2, and r3 is 3.

In the terminal $R^{f1'}$ ($R^{f1}$ when there is no $R^{f1'}$) in $R^{f1}$, r2 is preferably 2 or 3, and more preferably 3.

$R^{f2}$ each independently at each occurrence represents a hydroxyl group or a hydrolyzable group.

$R^{f3}$ each independently at each occurrence represents a hydrogen atom or a monovalent organic group, and is preferably a hydrogen atom or an alkyl group having 1 to 20 carbon atoms, and more preferably a hydrogen atom or an alkyl group having 1 to 6 carbon atoms (e.g., a methyl group, an ethyl group, a propyl group).

In one embodiment, $R^{f3}$ is an alkyl group having 1 to 6 carbon atoms (e.g., a methyl group, an ethyl group, a propyl group).

p1 is each independently at each occurrence an integer of 0 to 3, p2 is each independently at each occurrence an integer of 0 to 3, and p3 is each independently at each occurrence an integer of 0 to 3, provided that in each $R^{41}_{r1}R^{42}_{r2}R^{43}_{r3}Si$-$Z^1$—, the sum of p1, p2, and p3 is 3.

In formula (A3), there are at least two Si atoms to which a hydroxyl group or a hydrolyzable group binds.

In a preferable embodiment, at least one terminal part of the group represented by formula (A3) is $R^{42}_{r2}$, $R^{43}_{r3}$, $(R^{42}_{r2}R^{43}_{r3}Si$-$Z^1$—$)_2Si$— (wherein the sum of r2 and r3 is 3, and the sum of r2' and r3' is 1) or $(R^{42}_{r2}R^{43}_{r3}Si$—$Z^1$—$)_3Si$— (wherein the sum of r2 and r3 is 3), and preferably $(R^{42}_{r2}R^{43}_{r3}Si$-$Z^1$—$)_3Si$— (wherein the sum of r2 and r3 is 3). Here, r2 is an integer of 1 to 3, and preferably 2 or 3. In the formula, the $(R^{42}_{r2}R^{43}_{r3}Si$-$Z^1$—) unit is preferably $(R^{423}Si$-$Z^1$—). In a more preferable embodiment, all terminal parts of the group represented by formula (A3) may be $(R^{42}_{r2}R^{43}_{r3}Si$-$Z^1$)$_3$—Si—, and more preferably $(R^{423}Si$-$Z^1$)$_3$—Si—.

In one embodiment, p1 is preferably an integer of 1 to 3, more preferably 2 or 3, and particularly preferably 3. In this embodiment, r2 is preferably 1 to 3, more preferably 2 or 3, and even more preferably 3.

In one embodiment, preferably p1 is an integer of 1 to 3, and r2 is 2 or 3; more preferably p1 is 2 or 3, and r2 is 2 or 3; and even more preferably p1 is 3, and r2 is 2 or 3.

In one embodiment, preferably p1 is an integer of 1 to 3, and r2 is 3; more preferably p1 is 2 or 3, and r2 is 3; and even more preferably p1 is 3, and r2 is 3.

In one embodiment, p1 is an integer of 1 to 3, and $Z^1$ is a divalent organic group. Preferably, $Z^1$ excludes a group that forms a siloxane bond with the Si atom at the terminal of the molecular backbone (the Si atom to which $R^{f1}$ binds) in formula (A3). More preferably, $Z^1$ is preferably a $C_{1-6}$ alkylene group, $—(CH_2)_{111}—O—(CH_2)_{112}-$(wherein 111 is an integer of 1 to 6, and 112 is an integer of 1 to 6) or -phenylene-$(CH_2)_{113}—$ (wherein 113 is an integer of 0 to 6), and more preferably a $C_{1-3}$ alkylene group.

When the compound represented by formula (A2) and the compound represented by formula (A3) overlap, the compound represented by formula (A2) is given priority.

Formula (A4) will now be described below.

β4 is an integer of 1 to 9. β4 may vary according to the valence of $X^{a5}$. For example, when $X^{a5}$ is a decavalent organic group, β4 is 9. When $X^{a5}$ is a single bond, β4 is 1.

$X^{a5}$ represents a single bond or a di- to decavalent organic group, is preferably a di- to heptavalent, more preferably a di- to tetravalent, and even more preferably a divalent or trivalent organic group, and may be a divalent organic group. Herein, the right side of the structure of $X^{a5}$ binds to the triazine ring.

Examples of $X^{a5}$ include, but are not limited to, those described concerning $X^{a1}$. "Formula (A1)" and "β1" in the description concerning $X^{a5}$ correspond to "formula (A4)" and "β4", respectively.

Particularly preferable $X^{a5}$ may be a group represented by $—(R^{71})_{n21}—X^3—(R^{72})_{n22}—$ or $—R^{73}—$, and a group represented by $—(R^{71})_{n21}—X^3—(R^{72})_{n22}—$ is more preferable. In the formula, n21 is 1, n22 is 0, $R^{71}$ is $—(CH_2)_{n23}—$ (n23 is an integer of 1 to 6, more preferably an integer of 1 to 3, and even more preferably 1 or 2), $X^3$ is $—O—$ or $—NR^3—$ (e.g., $—NH—$), and $R^{73}$ is $—(CH_2)_{n27}—$ (n27 is an integer of 1 to 6, and preferably an integer of 1 to 3).

Specific examples of $X^{a5}$ include:
a single bond,
—O—,
—(CH$_2$)—O—,
—(CH$_2$)$_2$—O—,
—(CH$_2$)$_3$—O—,
—(CH$_2$)$_4$—O—,
—C(=O)—,
—CH$_2$—C(=O)—,
—C(=O)O—,
—CH$_2$—C(=O)O—,
—OC(=O)—,
—CH$_2$—OC(=O)—,
—C(=O)NH—,
—CH$_2$—C(=O)NH—,
—NHC(=O)—,
—NHCH$_2$-C(=O)—,
—NCH$_3$C(=O)—,
—CH$_2$—NCH$_3$C(=O)—,
—NH—,
—CH$_2$—NH—,
—(CH$_2$)$_2$—NH—,
—(CH$_2$)$_3$—NH—,
—(CH$_2$)$_4$—NH—,
—NCH$_3$—,
—CH$_2$—NCH$_3$—,
—(CH$_2$)$_2$—NCH$_3$—,
—(CH$_2$)$_3$—NCH$_3$—,
—(CH$_2$)$_4$—NH—,
—CH$_3$—,
—(CH$_2$)$_2$—,
—(CH$_2$)$_3$—;
—(CH$_2$)$_4$—,
—(CH$_2$)$_5$—,
—(CH$_2$)$_6$—,
—S—,
—CH$_2$—S—,
—(CH$_2$)$_2$—S—,
—(CH$_2$)$_3$—S—,
—SO$_2$NH—,
—SO$_2$NCH$_3$—,
—SO$_2$—,
—NHC(=O)—O—,
—CH$_2$NHC(=O)O—,
—CH$_2$OC(=O)NH—,
—O—C(=O)NH—,
—NHC(=O)NH—, and
—CH$_2$NHC(=O)NH—, provided that, herein, the left side of the structure of $X^{a5}$ binds to the group enclosed in parentheses provided with β4, and the right side of $X^{a5}$ binds to the triazine ring.

$R^{g1}$ each independently at each occurrence represents $R^{51}_{s1}R^{52}_{s2}R^{53}_{s3}C-Z^2—$.

$Z^2$ each independently at each occurrence represents an oxygen atom or a divalent organic group. The left side of the structure of $Z^2$ binds to the "C" atom contained in the group represented by $R^{51}_{s1}R^{52}_{s2}R^{53}_{s3}C-Z^2—$.

$Z^2$ is preferably a divalent organic group, and excludes a group that forms a siloxane bond with the Si atom at the terminal of the molecular backbone (the Si atom to which $R^{g1}$ binds) in formula (A4).

$Z^2$ is preferably a $C_{1-6}$ alkylene group, $—(CH_2)_{121}—O—(CH_2)_{122}—$ (wherein 121 is an integer of 0 to 6, for example, an integer of 1 to 6, and 122 is an integer of 0 to 6, for example, an integer of 1 to 6) or -phenylene-$(CH_2)_{123}—$ (wherein 123 is an integer of 0 to 6), and more preferably a $C_{1-3}$ alkylene group. These groups may be substituted with one or more substituents selected from, for example, a fluorine atom, a $C_{1-6}$ alkyl group, a $C_{2-6}$ alkenyl group, and a $C_{2-6}$ alkynyl group.

$R^{51}$ each independently at each occurrence represents $R^{g1'}$. $R^{g1'}$ has the same definition as $R^{g1}$.

In $R^{g1}$, the number of C atoms linearly connected via the group $Z^2$ is up to 5. That is to say, in $R^{g1}$, when there is at least one $R^{51}$, there are two or more C atoms linearly connected via the group $Z^2$ in $R^{g1}$, and the number of C atoms linearly connected via the group $Z^2$ is up to 5. The "number of C atoms linearly connected via the group $Z^2$ in $R^{g1}$" is equal to the number of repeats of $—Z^2—C—$ linearly connected in $R^{g1}$.

In a preferable embodiment, as shown below, "the number of C atoms linearly connected via the group $Z^2$ in $R^{g1}$" is 1 (the left formula) or 2 (the right formula) in all chains.

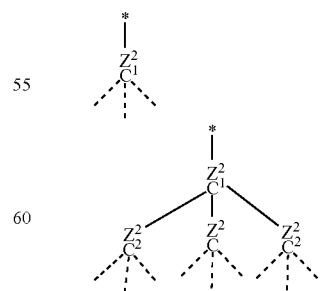

In one embodiment, the number of C atoms linearly connected via the group $Z^2$ in $R^{g1}$ is 1 or 2, and preferably 1.

$R^{52}$ each independently at each occurrence represents $R^a{}_{m1}R^b{}_{3-m1}Si-Z^3-$.

$R^a$ and $R^b$ have the same definition as above.

In formula (A4), m1 is independently an integer of 0 to 3 for each $(R^a{}_{m1}R^b{}_{3-m1}Si-)$ unit, provided that in formula (A4), there are at least two $R^a{}_{m1}R^b{}_{3-m1}Si-$ wherein m1 is 1 to 3.

$Z^3$ each independently at each occurrence represents an oxygen atom or a divalent organic group. The left side of the group represented by $Z^3$ binds to the "Si" atom contained in $R^{52}$.

In one embodiment, $Z^3$ is an oxygen atom.

In one embodiment, $Z^3$ is a divalent organic group.

In a preferable embodiment, $Z^3$ is a $C_{1-6}$ alkylene group, $-(CH_2)_{l31}-O-(CH_2)_{l32}-$ (wherein l31 is an integer of 0 to 6, for example, an integer of 1 to 6, and l32 is an integer of 0 to 6, for example, an integer of 1 to 6), or -phenylene-$(CH_2)_{l33}-$ (wherein l33 is an integer of 0 to 6). These groups may be substituted with one or more substituents selected from, for example, a fluorine atom, a $C_{1-6}$ alkyl group, a $C_{2-6}$ alkenyl group, and a $C_{2-6}$ alkynyl group.

In one embodiment, $Z^3$ may be a $C_{1-6}$ alkylene group or -phenylene-$(CH_2)_{l33}-$. When $Z^3$ is the above group, light resistance, in particular UV resistance, can be more increased. In the formula, l33 is an integer of 0 to 6.

$Z^3$ is preferably a $C_{1-6}$ alkylene group and more preferably a $C_{2-3}$ alkylene group.

$R^{53}$ each independently at each occurrence represents a hydrogen atom, a hydroxyl group, or a monovalent organic group, and is preferably a hydrogen atom or an alkyl group having 1 to 20 carbon atoms, and more preferably a hydrogen atom or an alkyl group having 1 to 6 carbon atoms (e.g., a methyl group, an ethyl group, a propyl group).

In one embodiment, $R^{53}$ is an alkyl group having 1 to 6 carbon atoms (e.g., a methyl group, an ethyl group, a propyl group).

s1 is each independently at each occurrence an integer of 0 to 3, s2 is each independently at each occurrence an integer of 0 to 3, and s3 is each independently at each occurrence an integer of 0 to 3, provided that in each $R^{51}{}_{s1}R^{52}{}_{s2}R^{53}{}_{s3}C-Z^2-$, the sum of s1, s2, and s3 is 3.

$R^{g2}$ each independently at each occurrence represents $R^a{}_{m1}R^b{}_{3-m1}Si-Z^4-$. The left side of the group represented by $Z^4$ binds to the "Si" atom contained in $R^{g2}$.

$R^a$ and $R^b$ have the same definition as above.

In one embodiment, $Z^4$ is an oxygen atom.

In one embodiment, $Z^4$ is a divalent organic group.

In a preferable embodiment, $Z^4$ is a $C_{1-6}$ alkylene group, $-(CH_2)_{l31'}-O-(CH_2)_{l32'}-$ (wherein l31' is an integer of 0 to 6, for example, an integer of 1 to 6, and l32' is an integer of 0 to 6, for example, an integer of 1 to 6), or -phenylene-$(CH_2)_{l33'}-$ (wherein l33' is an integer of 0 to 6). These groups may be substituted with one or more substituents selected from, for example, a fluorine atom, a $C_{1-6}$ alkyl group, a $C_{2-6}$ alkenyl group, and a $C_{2-6}$ alkynyl group.

In one embodiment, $Z^4$ may be a $C_{1-6}$ alkylene group or -phenylene-$(CH_2)_{l33'}-$. When $Z^4$ is the above group, light resistance, in particular UV resistance, can be more increased. In the formula, l33' is an integer of 0 to 6.

$Z^4$ is preferably a $C_{1-6}$ alkylene group, and more preferably a $C_{2-3}$ alkylene group.

$R^{g3}$ each independently at each occurrence represents a hydrogen atom, a hydroxyl group, or a monovalent organic group, and is preferably a hydrogen atom, a hydroxyl group, or a monovalent organic group, more preferably a hydrogen atom, a hydroxyl group, or an alkyl group having 1 to 20 carbon atoms, and even more preferably a hydrogen atom, a hydroxyl group, or an alkyl group having 1 to 6 carbon atoms (e.g., a methyl group).

q1 is each independently at each occurrence an integer of 0 to 3, q2 is each independently at each occurrence an integer of 0 to 3, and q3 is each independently at each occurrence an integer of 0 to 3, provided that the sum of q1, q2, and q3 is 3 in each $R^{g3}{}_{q3}R^{g2}{}_{q2}R^{g1}{}_{q1}C-$.

In one embodiment, at least one q1 is an integer of 1 to 3, preferably 2 or 3, and more preferably 3.

In one embodiment, q1 is an integer of 1 to 3, preferably 2 or 3, and more preferably 3.

In one embodiment, q2 is 2 or 3, and preferably 3.

In formula (A4), preferably there are at least two Si atoms to which a hydroxyl group or a hydrolyzable group binds. That is to say, in formula (A4), preferably there are at least two $R^{52}$ groups (provided that m1 is an integer of 1 to 3 in $R^{52}$) or $R^{g2}$ groups (provided that m1 is an integer of 1 to 3 in $R^{g2}$). In other words, in formula (A4), at least two integers m1 are preferably 1 or more. m1 is more preferably 2 or 3, and even more preferably 3. Having such a structure, the polyether group-containing compound can form a surface-treating layer having better UV resistance, water-repellency, oil-repellency, antifouling properties (e.g., preventing grime such as soil and fingerprints from adhering), heat resistance, high friction durability, hydrolysis resistance, chemical resistance, moisture-proof properties, fogging resistance, and the like, and in particular, good UV resistance, high friction durability, chemical resistance, and the like.

In formula (A4), preferably there is a group represented by $R^{g3}$ $(R^a{}_{m1}R^b{}_{3-m1}Si-)_2-C-$ or $(R^a{}_{m1}R^b{}_{3-m1}Si-)_3-C-$, and more preferably there is a group represented by $(R^a{}_{m1}R^b{}_{3-m1}Si-)_3-C-$. Here, m1 is an integer of 1 to 3, preferably 2 or 3, and more preferably 3.

In formula (A4), m1 is preferably 1 to 3, and more preferably 3.

In one embodiment, in formula (A4), the $(R^a{}_{m1}R^b{}_{3-m1}Si-)$ unit is $R^a{}_2R^bSi-$ or $R^a{}_3Si-$, and preferably $R^a{}_3Si-$.

In formula (A4), preferably, q2 is an integer of 1 to 3, and m1 is an integer of 1 to 3.

In one embodiment, in formula (A4), q2 is an integer of 1 to 3, m1 is 2 or 3, and more preferably q2 is an integer of 1 to 3, and m1 is 3.

In one embodiment, in formula (A4), q2 is 2 or 3, m1 is an integer of 1 to 3, more preferably q2 is 3, and m1 is an integer of 1 to 3, and even more preferably q2 is 3, and m1 is 3.

In a preferable embodiment, in the polyether group-containing compound of the present disclosure, one R group is a group represented by Rf-$X^{f1}$-PE-$X^{f2}$—$X^1$—, and two R groups are groups represented by $R^{Si}$—; and the group represented by $R^{Si}$— is each independently at each occurrence a group represented by $(R^a{}_{m1}R^b{}_{3-m1}Si)_3$—$X^{a3}$—, a group represented by $(R^{42}{}_{r2}R^{43}{}_{r3}Si-Z^1-)_3$-Si—$X^{a4}$—, or a group represented by $(R^a{}_{m1}R^b{}_{3-m1}Si-Z^4-)_3$-C—$X^{a5}$—, wherein Rf represents a perfluoroalkyl group having 1 to 6 carbon atoms;

$X^{f1}$ is a group represented by $(X^{f11})_z$;

$X^{f11}$ is an alkylene group having 1 to 6 carbon atoms wherein a hydrogen atom is optionally replaced with a fluorine atom;

z is 0;

PE is a group represented by formula: —$(OC_6F_{12})_a$—$(OC_5F_{10})_b$—$(OC_4F_8)_c$—$(OC_3X^{10}{}_6)_d$—$(OC_2F_4)_e$—$(OCF_2)_f$— wherein a, b, c, d, e, and f are each independently an integer of 0 or more and 200 or less, the sum of a, b, c, d, e, and f is at least 1, the occurrence order of the respective repeating units enclosed in parentheses provided with a, b, c, d, e, or f is not limited in the formula, and $X^{10}$ is each independently at each occurrence a hydrogen atom, a fluorine atom, or a chlorine atom, preferably a hydrogen atom or a fluorine atom, and more preferably a fluorine atom;

$X^{f2}$ is a group represented by (O) y or (NH) y, and preferably a group represented by (0) y;

y is 0 or 1;

$X^1$ is a group represented by $—(R^{11})_{n16}—X^{11}—(R^{12})_{n17}—$;

$R^{11}$ represents $—(CH_2)_{n11}—$, n11 is an integer of 1 to 3, and preferably 1 or 2;

n16 is 1;

$X^{11}$ is —O— or —NH—;

n17 is 0;

$X^{a3}$, $X^{a4}$, or $X^{a5}$ is each independently at each occurrence $—(R^{71})_{21}—X^3—(R^{72})_{n22}—$;

$R^{71}$ is $—(CH_2)_{n23}—$ (n23 is an integer of 1 to 3, and more preferably 1 or 2);

n21 is 1;

$X^3$ is a group represented by —O— or —NH—;

n22 is 0;

$Z^1$ is a $C_{1-3}$ alkylene group;

$Z^4$ is a $C_{1-3}$ alkylene group;

$R^a$ is each independently at each occurrence a hydroxyl group or a hydrolyzable group;

$R^b$ is a methyl group;

m1 is each independently at each occurrence an integer of 1 to 3, and preferably 3;

$R^{42}$ represents each independently at each occurrence a hydroxyl group or a hydrolyzable group;

$R^{43}$ is each independently at each occurrence a hydrogen atom or an alkyl group having 1 to 6 carbon atoms (e.g., a methyl group, an ethyl group, a propyl group); and r2 is 2 or 3, the sum of r2 and r3 is 3, and preferably r2 is 3.

In the above embodiment, the group represented by $R^{Si}—$ more preferably has the same structure. For example, the group represented by $R^{Si}—$ is a group represented by $(R^a{}_{m1}R^b{}_{3-m1}Si-Z^4—)_3-C—X^{a5}—$.

In another preferable embodiment, in the polyether group-containing compound of the present disclosure, two R groups are represented by Rf-$X^{f1}$-PE-$X^{f2}$—$X^1$—, and one R group is represented by $R^{Si}$—; and the group represented by $R^{Si}$— is each independently at each occurrence a group represented by $(R^a{}_{m1}R^b{}_{3-m1}Si)_3—X^{a3}—$, a group represented by $(R^{42}{}_{r2}R^{43}{}_{r3}Si-Z^1—)_3-Si—X^{a4}—$, or a group represented by $(R^a{}_{m1}R^b{}_{3-m1}Si-Z^4—)_3-C—X^{a5}—$, wherein Rf represents a perfluoroalkyl group having 1 to 6 carbon atoms;

$X^{f1}$ is a group represented by $(X^{f11})_z$;

$X^{f11}$ is an alkylene group having 1 to 6 carbon atoms wherein a hydrogen atom is optionally replaced with a fluorine atom;

z is 0;

PE is a group represented by formula: $—(OC_6F_{12})_a—(OC_5F_{10})_b—(OC_4F_8)_c—(OC_3X^{10}{}_6)_d—(OC_2F_4)_e—(OCF_2)_f—$ wherein a, b, c, d, e, and f are each independently an integer of 0 or more and 200 or less, the sum of a, b, c, d, e, and f is at least 1, the occurrence order of the respective repeating units enclosed in parentheses provided with a, b, c, d, e, or f is not limited in the formula, and $X^{10}$ is each independently at each occurrence a hydrogen atom, a fluorine atom, or a chlorine atom, preferably a hydrogen atom or a fluorine atom, and more preferably a fluorine atom;

$X^{f2}$ is each independently at each occurrence a group represented by $(O)_y$ or $(NH)_y$, and preferably a group represented by $(O)_y$;

y is each independently at each occurrence 0 or 1;

$X^1$ is a group represented by $—(R^{11})_{n16}—X^{11}—(R^{12})_{n17}$;

$R^{11}$ represents $—(CH_2)_{n11}—$, n11 is an integer of 1 to 3, and preferably 1 or 2;

n16 is 1;

$X^{11}$ is —O— or —NH—;

n17 is 0;

$X^{a3}$, $X^{a4}$, or $X^{a5}$ is each independently at each occurrence $—(R^{71})_{n21}—X^3—(R^{72})_{n22}—$;

$R^{71}$ is $—(CH_2)_{n23}—$ (n23 is an integer of 1 to 3, and more preferably 1 or 2);

n21 is 1;

$X^3$ is a group represented by —O— or —NH—;

n22 is 0;

$Z^1$ is a $C_{1-3}$ alkylene group;

$Z^4$ is a $C_{1-3}$ alkylene group;

$R^a$ is each independently at each occurrence a hydroxyl group or a hydrolyzable group;

$R^b$ is a methyl group;

m1 is each independently at each occurrence an integer of 1 to 3, and preferably 3;

$R^{42}$ each independently at each occurrence represents a hydroxyl group or a hydrolyzable group;

$R^{43}$ is each independently at each occurrence a hydrogen atom or an alkyl group having 1 to 6 carbon atoms (e.g., a methyl group, an ethyl group, a propyl group); and r2 is 2 or 3, the sum of r2 and r3 is 3, and preferably r2 is 3.

[Composition]

The composition containing the polyether group-containing compound of the present disclosure may contain a solvent, a fluorine-containing oil, a silicone oil, a catalyst, a surfactant, a polymerization inhibitor, a sensitizer, sol-gel, a hydrocarbon-based polymer, a fluorine-containing polymer, a radical scavenger, an inorganic porous material, a dehydrating agent, a dehalogenating compound, or the like.

Examples of the solvent include aliphatic hydrocarbons such as hexane, cyclohexane, heptane, octane, nonane, decane, undecane, dodecane, and mineral spirits; aromatic hydrocarbons such as benzene, toluene, xylene, naphthalene, and solvent naphtha; esters such as methyl acetate, ethyl acetate, propyl acetate, n-butyl acetate, isopropyl acetate, isobutyl acetate, cellosolve acetate, propylene glycol methyl ether acetate, carbitol acetate, diethyl oxalate, ethyl pyruvate, ethyl 2-hydroxybutyrate, ethyl acetoacetate, amyl acetate, methyl lactate, ethyl lactate, methyl 3-methoxypropionate, ethyl 3-methoxypropionate, methyl 2-hydroxyisobutyrate, and ethyl 2-hydroxyisobutyrate; ketones such as acetone, methyl ethyl ketone, methyl isobutyl ketone, 2-hexanone, cyclohexanone, methyl amino ketone, and 2-heptanone; glycol ethers such as ethyl cellosolve, methyl cellosolve, methyl cellosolve acetate, ethyl cellosolve acetate, propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate, dipropylene glycol dimethyl ether, and ethylene glycol monoalkyl ether; alcohols such as methanol, ethanol, iso-propanol, n-butanol, isobutanol, tert-butanol, sec-butanol, 3-pentanol, octyl alcohol, 3-methyl-3-methoxybutanol, and tert-amyl alcohol; glycols such as ethylene glycol and propylene glycol; cyclic ethers such as tetrahydrofuran, tetrahydropyran, and dioxane; amides such as N, N-dimethylformamide and N, N-dimethylacetamide; ether alcohols such as methyl cellosolve, cellosolve, isopropyl cellosolve, butyl cellosolve, and diethylene glycol monomethyl ether; diethylene glycol monoethyl ether acetate; and fluorine-containing solvents such as 1,1,2-trichloro-1,2,2-trifluoroethane, 1,2-dichloro-1,1,2,2-tetrafluoroethane, dimethyl sulfoxide, 1,1-dichloro-1,2,2,3,3-pentafluoropropane (HCFC 225), Galden HT PFPE, AE-3000, Zeorora H, HFE 7100, HFE 7200, HFE 7300, m-hexafluorometaxylene, hexafluorobenzene, and perfluorohexane. Alternatively, the solvent may be a mixed solvent of two or more of such solvents.

In another embodiment, the composition containing the polyether group-containing compound of the present disclosure may further contain at least one selected from the group consisting of hexafluorobenzene, m-hexafluoroxylene, perfluorobutyl ethyl ether, perfluorohexyl methyl ether, Zeorora H, perfluorohexyl methyl ether, perfluorohexane, acetone, N, N-dimethylformamide, dimethyl sulfoxide, N-methyl-2-pyrrolidone, and water.

Examples of (non-reactive) fluoropolyether compounds, and preferably perfluoro (poly) ether compounds, that can be interpreted as fluorine-containing oil (hereafter referred to as "fluorine-containing oil") include, but are not limited to, compounds (perfluoro (poly) ether compounds) represented by the following general formula (3):

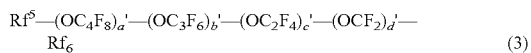

(3)

wherein $Rf^5$ represents a $C_{1-16}$ alkyl group optionally substituted with one or more fluorine atoms (preferably, a $C_{1-16}$ perfluoroalkyl group), $Rf^6$ represents a $C_{1-16}$ alkyl group optionally substituted with one or more fluorine atoms (preferably, a $C_{1-16}$ perfluoroalkyl group), a fluorine atom, or a hydrogen atom, and $Rf^5$ and $Rf^6$ more preferably are each independently a $C_{1-3}$ perfluoroalkyl group;

a', b', c', and d' respectively represent the numbers of 4 repeating units of perfluoro (poly) ether constituting the main backbone of the polymer and are mutually independently an integer of 0 or more and 300 or less, and the sum of a', b', c', and d' is at least 1, preferably 1 to 300, and more preferably 20 to 300; and the occurrence order of the respective repeating units enclosed in parentheses provided with a subscript a', b', c', or d' is not limited in the formula. Among these repeating units, —(OC$_4$F$_8$)— may be any of —(OCF$_2$CF$_2$CF$_2$CF$_2$)—, —(OCF(CF$_3$)CF$_2$CF$_2$)—, —(OCF$_2$CF(CF$_3$)CF$_2$)—, —(OCF$_2$CF$_2$CF(CF$_3$))—, —(OC(CF$_3$)$_2$CF$_2$)—, —(OCF$_2$C(CF$_3$)$_2$)—, —(OCF(CF$_3$)CF(CF$_3$))—, —(OCF(C$_2$F$_5$)CF$_2$)—, and —(OCF$_2$CF(C$_2$F$_5$))—, and preferably —(OCF$_2$CF$_2$CF$_2$CF$_2$)—. —(OC$_3$F$_6$)— may be any of —(OCF$_2$CF$_2$CF$_2$)—, —(OCF(CF$_3$)CF$_2$)—, and —(OCF$_2$CF(CF$_3$))—, and preferably —(OCF$_2$CF$_2$CF$_2$)—. —(OC$_2$F$_4$)— may be any of —(OCF$_2$CF$_2$)— and (OCF(CF$_3$))—, and preferably —(OCF$_2$CF$_2$)—.

Examples of the perfluoro (poly) ether compound represented by general formula (3) include a compound represented by any of the following general formulae (3a) and (3b) (which may be used singly or as a mixture of two or more):

(3a)

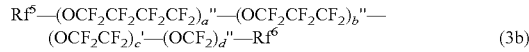

(3b)

In these formulae, $Rf^5$ and $Rf^6$ are as described above; in formula (3a), b" is an integer of 1 or more and 100 or less; and in formula (3b), a" and b" are each independently an integer of 0 or more and 30 or less, and c" and d" are each independently an integer of 1 or more and 300 or less. The occurrence order of the respective repeating units enclosed in parentheses provided with a subscript a", b", c", or d" is not limited in the formulae.

From another viewpoint, the fluorine-containing oil may be a compound represented by general formula $Rf^3$—F wherein $Rf^3$ is a $C_{5-16}$ perfluoroalkyl group. The fluorine-containing oil may be a chlorotrifluoroethylene oligomer.

The fluorine-containing oil may have an average molecular weight of 500 to 10,000. The molecular weight of the fluorine-containing oil may be measured using GPC.

The fluorine-containing oil may be contained in an amount of, for example, 0 to 50 mass %, preferably 0 to 30 mass %, and more preferably 0 to 5 mass % based on the composition of the present disclosure. In one embodiment, the composition of the present disclosure is substantially free of the fluorine-containing oil. Being substantially free of the fluorine-containing oil means that the fluorine-containing oil is not contained at all, or an extremely small amount of the fluorine-containing oil may be contained.

The fluorine-containing oil contributes to increasing the surface lubricity of a layer formed of the composition of the present disclosure.

In one embodiment, the average molecular weight of the fluorine-containing oil may be greater than the average molecular weight of the polyether group-containing compound. With such average molecular weights, better friction durability and surface lubricity can be obtained. This embodiment is particularly advantageous when the surface-treating layer is formed by a vacuum deposition method.

In one embodiment, the average molecular weight of the fluorine-containing oil may be smaller than the average molecular weight of the polyether group-containing compound. With such average molecular weights, the composition of the present disclosure is capable of forming a cured product that is formed using the composition and has high friction durability and high surface lubricity while suppressing deterioration of the transparency of the cured product.

For example, the silicone oil may be linear or cyclic silicone oil having 2,000 or less siloxane bonds. The linear silicone oil may be so-called straight silicone oil or modified silicone oil. Examples of the straight silicone oil include dimethyl silicone oil, methyl phenyl silicone oil, and methyl hydrogen silicone oil. Examples of the modified silicone oil include those obtained by modifying straight silicone oil with alkyl, aralkyl, polyether, higher fatty acid ester, fluoroalkyl, amino, epoxy, carboxyl, alcohol, or the like. Examples of the cyclic silicone oil include cyclic dimethylsiloxane oil.

In the composition of the present disclosure (e.g., a surface-treating agent), such silicone oil may be contained in an amount of, for example, 0 to 300 parts by mass, and preferably 50 to 200 parts by mass, with respect to total 100 parts by mass of the polyether group-containing compound of the present disclosure (in the case of two or more kinds, the total thereof, and the same applies below).

Silicone oil contributes to increasing the surface lubricity of the surface-treating layer.

Examples of the catalyst include acids (such as acetic acid and trifluoroacetic acid), bases (such as ammonia, triethylamine, and diethylamine), and transition metals (such as Ti, Ni, and Sn).

The catalyst promotes hydrolysis and dehydrative condensation of the polyether group-containing compound of the present disclosure, and promotes formation of a layer formed of the composition (e.g., a surface-treating agent) of the present disclosure.

Examples of other components include, in addition to those described above, tetraethoxysilane, methyltrimethoxysilane, 3-aminopropyltrimethoxysilane, 3-glycidoxypropyltrimethoxysilane, and methyltriacetoxysilane.

The composition containing the polyether group-containing compound of the present disclosure may further contain compound (s) represented by the following formulae or compound (s) obtained by at least partially hydrosilylating a group represented by $R^{Si"}$ in the compounds having the group represented by $R^{Si"}$ among the compounds represented by the following formulae. The composition of the present disclosure may contain compound (s) represented by the following formulae or the above-described compound (s) obtained by hydrosilylating the compounds represented by the following formulae in an amount of, for example, 1 mass ppm to 1 mass %, or 10 mass ppm to 0.1 mass %, in the composition of the present disclosure:

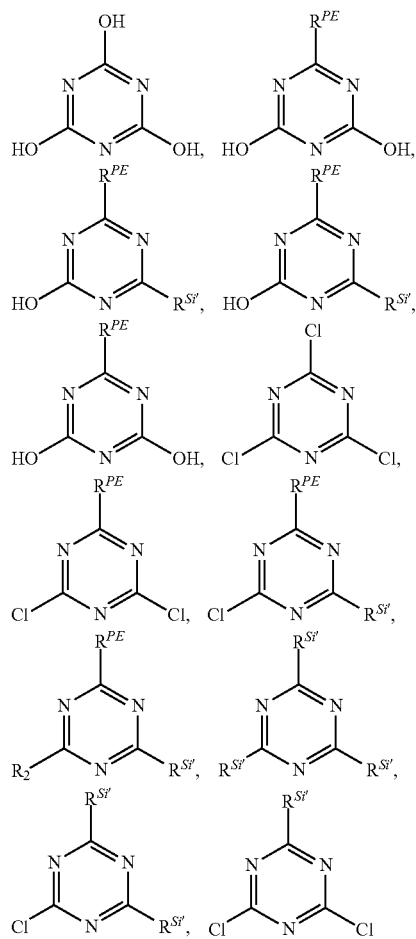

wherein $R^{PE}$ is a group represented by $(Rf-X^{f1}-PE-X^{f2})_\alpha-X^1-$;

each symbol in the group represented by $R^{PE}$ has the same definition as above; and $R^{Si"}$ is each independently at each occurrence a monovalent organic group having $-CH=CH_2$ at the terminal, and preferably a group that becomes a group represented by $R^{Si'}$ by hydrosilylation.

In one embodiment, the composition of the present disclosure may further contain a metal, a metal oxide, or a metal salt containing Pt, Pd, Rh, Na, K, Ca, Mg, Zn, Fe, Cu, Al, or the like; a compound, an oxide, or a salt containing Si. The composition of the present disclosure may contain a metal, a metal oxide, or a salt thereof in an amount of, for example, 10 mass ppb to 1 mass %, or 100 mass ppb to 0.1 mass %, in the compositions of the present disclosure.

In one embodiment, the composition of the present disclosure may further contain an organic amine or a hydrochloride thereof.

The composition of the present disclosure may contain an organic amine or a salt thereof in an amount of, for example, 1 mass ppm to 1 mass %, or 10 mass ppm to 0.1 mass %.

[Production Method]

Next, one example of the method for producing the polyether group-containing compound of the present disclosure will now be described. The method for producing the polyether group-containing compound of the present disclosure is not limited to the following method.

The method for producing the polyether group-containing compound of the present disclosure includes the following steps.

Step (1):

Step of reacting a compound represented by the following formula (II):

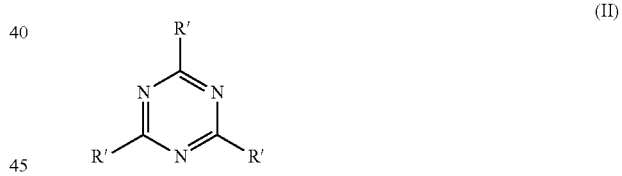

with $HSiM^2_3$ and, optionally, a compound represented by $R^a{}_{k1}L'$ and/or a compound represented by formula $R^b{}_{k2}L''$ to obtain a compound represented by formula (I):

Each symbol will be described below.

The method for producing the polyether group-containing compound of the present disclosure may further include the following step before step (I):

Step (2):

Step of reacting a compound represented by the following formula (III):

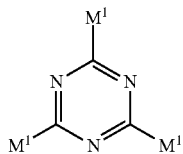

(III)

with a compound represented by Rf-$X^{f1}$-PE-$X^{f2}$—$X^1$—G and a compound represented by $CH_2$=CH—X'-G' to obtain a compound represented by formula (II):

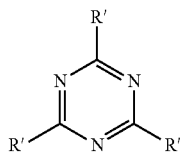

(II)

Each symbol will be described below.
Below, each step will now be described in detail.
(Step (1))
Step (1) is the step of reacting a compound represented by formula (II):

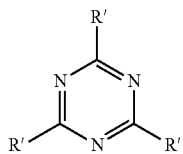

(II)

with $HSiM^2_3$ and, optionally, a compound represented by $R^a_{k1}L'$ and/or a compound represented by formula $R^b_{k2}L''$ to obtain a compound represented by formula (I):

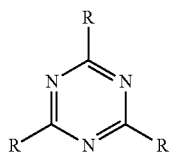

(I)

One or two of the R'— groups are groups represented by Rf-$X^{f1}$-PE-$X^{f2}$—$X^1$—, and one or two of the R'— groups are groups represented by $CH_2$=CH—X'—, for each compound represented by formula (II);
provided that the total of the number of groups represented by Rf-$X^{f1}$-PE-$X^{f2}$—$X^1$— and the number of groups represented by $CH_2$=CH—X'— is 3 for each compound represented by formula (II).

For example, one R' group may be a group represented by Rf-$X^{f1}$-PE-$X^{f2}$—$X^1$— and two R' groups may be groups represented by $CH_2$=CH—X'—; and two R' groups may be groups represented by Rf-$X^{f1}$-PE-$X^{f2}$—$X^1$—, and one R' group may be a group represented by $CH_2$=CH—X'—.

The group represented by Rf-$X^{f1}$-PE-$X^{f2}$— is not involved in the reaction in step (1). Accordingly, the group represented by Rf-$X^{f1}$-PE-$X^{f2}$—$X^1$— in formula (II) corresponds to the group represented by (Rf-$X^{f1}$-PE-$X^{f2}$)$_\alpha$—$X^1$— ($\alpha$=1) in formula (I).

Rf, $X^{f1}$, PE, $X^{f2}$, and $X^1$ have the same definition as above.

X' becomes a part of the linker moiety connecting the triazine ring and the Si atom. For example, in formula (I), when the group represented by $R^{Si}$— is a group represented by formula (A2), the structure represented by —$CH_2CH_2X'$— corresponds to the group represented by $X^{a3}$.

$R^a$ and $R^b$ have the same definition as above.

L' each independently at each occurrence represents a group capable of bonding with $R^a$.

k1 is each independently at each occurrence an integer of 1 to 3.

L'' each independently at each occurrence represents a group capable of bonding with $R^b$.

k2 is each independently at each occurrence an integer of 1 to 3.

The compound represented by formula (II) may be a compound obtained in step (2) described below.

When the compound represented by formula (II) is reacted with $HSiM^2_3$, the group represented by $CH_2$=CH—X'— is converted to the group represented by $SiM^2_3$—$CH_2CH_2$—X'—.

$M^2$ is each independently at each occurrence a halogen atom (i.e., I, Br, Cl, F) or a $C_{1-6}$ alkoxy group, and preferably Cl. The compound is commercially available, or can be produced from a commercially available compound by using an ordinary technique in the art.

The amount of $HSiM^2_3$ is 1 mol or more, and preferably 2 mol, based on 1 mol of the terminal $CH_2$=CH— group of the compound represented by formula (II) (in the case of using two or more compounds, the total thereof, and the same applies below).

When the compound represented by $R^a_{k1}L'$ is used in the reaction, the amount of the compound used can be changed according to the amount of the $R^a$ group to be introduced, and the amount can be suitably determined by those skilled in the art.

When the compound represented by $R^b_{k2}L''$ is used in the reaction, the amount of the compound used can be changed according to the amount of the $R^b$ group to be introduced, and the amount can be suitably determined by those skilled in the art.

In the reaction of step (1), first, the terminal $CH_2$=CH— group of the compound of formula (II) and $HSiM^2_3$ react so that the terminal is converted to an $SiM^2_3$—$CH_2CH_2$— group. Then, this terminal $SiM^2_3$—$CH_2CH_2$— group reacts with the compound represented by $R^a_{k1}L'$ and/or the compound represented by $R^b_{k2}L''$ so that $M^2$ is replaced with $R^a$ or $R^b$. The compound represented by $R^a_{k1}L'$ and the compound represented by $R^b_{k2}L''$ may be reacted simultaneously or separately.

However, in one embodiment of the present disclosure, $HSiM^2_3$, the compound represented by $R^a_{k1}L'$, and the compound represented by $R^b_{k2}L''$ can also be used as a compound represented by $HSi(R^a_{k1})(R^b_{k2})$ (in this case, k1+k2 is 3). The compound represented by $HSi(R^a_{k1})(R^b_{k2})$ can be produced using an ordinary technique in the art.

In another embodiment, the total amount of the compound represented by $R^a_{k1}L'$ and/or the compound represented by $R^b_{k2}L''$ used in step (1) is 3 mol or more based on 1 mol of the terminal $CH_2$=CH— group of the compound represented by formula (II). In such an embodiment, substantially all $M^2$ of the terminal $SiM^2_3$—$CH_2CH_2$— produced in the reaction of step (1) can be replaced with $R^a$ or $R^b$.

In yet another embodiment, the total amount of the compound represented by $R^a_{k1}L'$ and/or the compound represented by $R^b_{k2}L''$ used in step (1) is 0 mol or more and less than 3 mol based on 1 mol of the terminal $CH_2=CH—$ group of the compound represented by formula (II). In such an embodiment, all or some $M^2$ of the terminal $SiM^2{}_3—CH_2CH_2—$ produced in the reaction of step (1) may remain without being replaced with $R^a$ or $R^b$. By reacting the thus-remaining M-Si moiety with a compound represented by formula: Hal-J-Z'—CH=CH$_2$ (wherein Hal represents a halogen atom, J represents Mg, Cu, or Zn, and Z' represents a bond or a divalent organic group), the terminal part can be $CH_2=CH—$, and can be subjected to the same reaction as step (1). By repeating this operation, in the terminal of the compound represented by formula (II), Si atoms can be connected in a tree-shaped structure via a linker moiety.

The reaction of step (1) may be carried out in a suitable solvent in the presence of a suitable catalyst.

Examples of the suitable catalyst include, but are not limited to, Pt, Pd, and Rh. Such a catalyst may be in any form, e.g., in the form of a complex.

The suitable solvent is not limited as long as it does not adversely affect the reaction, and examples include hexafluorobenzene, m-hexafluoroxylene, perfluorobutyl ethyl ether, perfluorohexyl methyl ether, Zeorora H, perfluorohexyl methyl ether, and perfluorohexane.

The reaction temperature in the reaction is not limited, and is usually 0 to 100° C. and preferably ambient temperature to 80° C.; the reaction time is not limited, and is usually 60 to 600 minutes and preferably 120 to 300 minutes; and the reaction pressure is not limited, and is –0.2 to 1 MPa (gauge pressure) and is conveniently ambient pressure.

Herein, ambient temperature indicates 0 to 40° C.

In formula (I), R has the same definition as above. However, the number of groups represented by $(Rf-X^{f1}-PE-X^{f2})_\alpha—X^1—$ and the number of groups represented by $R^{Si}—$ in formula (I) correspond to the number of groups represented by $Rf-X^{f1}-PE-X^{f2}—X^1—$ and the number of groups represented by $CH_2=CH—X'—$ in formula (II), respectively.

(Step (2))

Step (2) is the step of reacting a compound represented by formula (III):

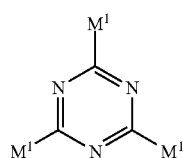

(III)

with a compound represented by $Rf-X^{f1}-PE-X^{12}—X^1—G$ and a compound represented by $CH_2=CH—X'-G'$ to obtain a compound represented by formula (II):

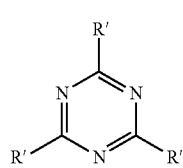

(II)

$M^1$ is each independently at each occurrence a halogen atom (i.e., I, Br, C$_1$, F, and preferably C$_1$); and R' is as described in step (1).

In step (2),

Rf, $X^{f1}$, PE, $X^1$, $X^{f2}$, and X' have the same definition as above;

G is each independently at each occurrence a hydroxyl group or $NH_2—$; and

G' is each independently at each occurrence $NH_2—$, a hydroxyl group, or SH—.

In step (2), the amounts of the compound represented by $Rf-X^{f1}-PE-X^{f2}—X^1—G$ and the compound represented by $CH_2=CH—X'-G'$ used can be changed according to the amounts of the group represented by $Rf-X^{f1}-PE-X^{f2}—X^1—$ and the group represented by $CH_2=CH—X'—$ to be introduced, and the amounts can be suitably determined by those skilled in the art.

In one embodiment, step (2) is reacting 1 mol of the compound represented by $Rf-X^{f1}-PE-X^{f2}-G$ and 2 mol of the compound represented by $CH_2=CH—X'-G'$ with 1 mol of the compound represented by formula (III) to obtain the compound represented by formula (II). This embodiment is suitable for synthesis of the compound represented by formula (II) wherein one R'— group is a group represented by $Rf-X^{f1}-PE-X^{f2}—X^1—$, and two R— groups are groups represented by $CH_2=CH—X'—$.

In one embodiment, step (2) is reacting 2 mol of the compound represented by $Rf-X^{f1}-PE-X^{f2}-G$ and 1 mol of the compound represented by $CH_2=CH—X'-G'$ with 1 mol of the compound represented by the formula (III) to obtain the compound represented by formula (II). This embodiment is suitable for synthesis of the compound represented by formula (II) wherein two R'— groups are groups represented by $Rf-X^{f1}-PE-X^{f2}—X^1—$, and one R— group is a group represented by $CH_2=CH—X'—$.

The reaction of step (2) is preferably carried out in a suitable solvent in the presence of a suitable catalyst.

The suitable catalyst may preferably be a basic compound, for example, amine-based catalysts such as tertiary amines and heterocyclic compounds having an amino group, and salts of potassium, sodium, cesium, and the like, and specific examples include diisopropylethylamine, triethylamine, DBU (diazabicycloundecene), pyridine, 2,6-lutidine, potassium carbonate, sodium carbonate, cesium carbonate, sodium hydrogencarbonate, and potassium hydrogencarbonate.

In one embodiment, the catalyst is a tertiary amine.

The suitable solvent is not limited as long as it does not adversely affect the reaction, and, for example, a hydrocarbon-based solvent and a fluorine-containing solvent are usable, and, specifically, hexafluorobenzene, m-hexafluoroxylene, perfluorobutyl ethyl ether, perfluorohexyl methyl ether, Zeorora H, perfluorohexyl methyl ether, perfluorohexane, acetone, N,N-dimethylformamide, dimethyl sulfoxide, N-methyl-2-pyrrolidone, and water are usable.

The reaction temperature in the reaction is not limited, and is usually 0 to 100° C. and preferably ambient temperature to 80° C.; the reaction time is not limited, and is usually 60 to 600 minutes and preferably 120 to 300 minutes; and the reaction pressure is not limited, and is –0.2 to 1 MPa (gauge pressure) and is conveniently ambient pressure.

Step (2) is preferably carried out as follows.

Step (2-1): Step of reacting a compound represented by the following formula (III):

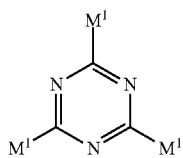

(III)

with a compound represented by Rf-$X^{f1}$-PE-$X^{f2}$—$X^1$—G to convert a group represented by $M^1$ to a group represented by Rf-$X^{f1}$-PE-$X^{f2}$—$X^1$—; and Step (2-2): Step of reacting the compound obtained in step (2-1) with a compound represented by $CH_2$=CH—X'-G' to convert a group represented by $M^1$ to a group represented by $CH_2$=CH—X'—.

In step (2-1), one or two groups represented by M' are converted to group (s) represented by Rf-$X^{f1}$-PE-$X^{f2}$—$X^1$—, and in step (2-2), one or two groups represented by M' are converted to group (s) represented by $CH_2$=CH—X'—, provided that the number of groups represented by Rf-$X^{f1}$-PE-$X^{f2}$—$X^1$— and the number of groups represented by $CH_2$=CH— X'— is 2 or 3.

Step (2-1) may be carried out in a suitable solvent in the presence of a suitable catalyst. For example, the catalysts and the solvents described in step (2) can be used.

The reaction temperature in step (2-1) is not limited, and can be carried out usually at 0 to 100° ° C., for example, room temperature (specifically 10 to 30° C.); the reaction time is not limited, and is usually 60 to 600 minutes and may be 24 hours as necessary; and the reaction pressure is not limited, and is −0.2 to 1 MPa (gauge pressure) and is conveniently ambient pressure.

Step (2-2) may be carried out in a suitable solvent in the presence of a suitable catalyst. For example, the catalysts and the solvents described in step (2) can be used.

The reaction temperature in step (2-2) is not limited, and the reaction can be carried out usually at 0 to 100° C., for example, ambient temperature to 80° C.; the reaction time is not limited, and usually 60 to 600 minutes; and the reaction pressure is not limited, and is −0.2 to 1 MPa (gauge pressure) and is conveniently ambient pressure.

In one embodiment,
in step (2-1), 1 mol of the compound represented by Rf-$X^{f1}$-PE-$X^{f2}$-G is reacted with 1 mol of the compound represented by formula (III), and
in step (2-2), the compound obtained in step (2-1) is reacted with the compound represented by $CH_2$=CH—X'-G' to convert the group represented by $M^1$ to the group represented by $CH_2$=CH—X'—.

This embodiment is suitable for synthesis of the compound represented by formula (II) wherein one R'— group is a group represented by Rf-$X^{f1}$-PE-$X^{f2}$—$X^1$—, and two R— groups are groups represented by $CH_2$=CH—X'—.

In this embodiment, for example, 2 mol, 2 to 3 mol, or 2 to 10 mol of the compound represented by $CH_2$=CH—X'-G' may be added to 1 mol of the compound represented by formula (III).

In one embodiment,
in step (2-1), 2 mol of the compound represented by Rf-$X^{f1}$-PE-$X^{f2}$-G is reacted with 1 mol of the compound represented by formula (III), and
in step (2-2), the compound obtained in step (2-1) is reacted with the compound represented by $CH_2$=CH—X'-G' to convert the group represented by $M^1$ to the group represented by $CH_2$=CH—X'—.

This embodiment is suitable for synthesis of the compound represented by formula (II) wherein two R'— groups are groups represented by Rf-$X^{f1}$-PE-$X^{f2}$—$X^1$—, and one R— group is a group represented by $CH_2$=CH—X'—.

In this embodiment, for example, 1 mol, 1 to 2 mol, or 1 to 10 mol of the compound represented by $CH_2$=CH—X'-G' may be added to 1 mol of the compound represented by formula (III).

Moreover, a concentration step, a washing step, and the like may be carried out on the reaction solution as necessary.

So far, a method for producing the polyether group-containing compound of the present disclosure has been described. The method for producing the polyether group-containing compound of the present disclosure is not limited to the exemplary production method above.

The composition of the present disclosure can be used as a surface-treating agent for surface treatment of a base material.

The composition of the present disclosure (e.g., a surface-treating agent) can be formed into pellets by impregnating a porous material such as a porous ceramic material or a metal fiber such as a fiber obtained by, for example, solidifying steel wool in a cotton-like form with the composition. Such pellets can be used in, for example, vacuum deposition.

[Article]

Below, the article of the present disclosure will now be described.

The article of the present disclosure includes a base material and, on the surface of the base material, a layer (a surface-treating layer) formed of the polyether group-containing compound of the present disclosure or a composition (a surface-treating agent) containing the polyester group-containing compound of the present disclosure (hereinafter, these are simply referred to as "the surface-treating agent of the present disclosure" collectively).

The base material usable in the present disclosure may be composed of any suitable material such as glass, resin (which may be natural or synthetic resin such as a commonly used plastic material, and may be in the form of a plate, a film, or the like), metal, ceramics, semiconductors (such as silicon and germanium), fiber (such as woven fabric and nonwoven fabric), fur, leather, wood, pottery, stone, and building materials.

For example, when the article to be produced is an optical member, the material constituting the surface of the base material may be a material for an optical member, such as glass or a transparent plastic. When the article to be produced is an optical member, some layer (or film) such as a hard coat layer or an antireflection layer may be formed on the surface (the outermost layer) of the base material. The antireflection layer may be any of a single-layer antireflection layer and a multi-layer antireflection layer. Examples of inorganic substances usable in the antireflection layer include $SiO_2$, SiO, $ZrO_2$, $TiO_2$, TiO, $Ti_2O_3$, $Ti_2O_5$, $Al_2O_3$, $Ta_2O_5$, $CeO_2$, MgO, $Y_2O_3$, $SnO_2$, $MgF_2$, and $WO_3$. One of these inorganic substances may be used singly, or two or more may be used in combination (e.g., as a mixture). In the case of a multi-layer antireflection layer, $SiO_2$ and/or SiO is preferably used in the outermost layer thereof. When the article to be produced is an optical glass component for a touch panel, a part of the surface of the base material (glass) may have a transparent electrode such as a thin film in which indium tin oxide (ITO), indium zinc oxide, or the like is used. The base material, according to its specific configuration or the like, may have an insulating layer, an adhesive layer, a protecting layer, a decorated frame layer (I-CON), an atomizing film layer, a hard coating layer, a polarizing film, a phase difference film, a liquid crystal display module, or the like.

The shape of the base material is not limited. The surface region of the base material on which a surface-treating layer is to be formed is at least a part of the base material surface, and may be suitably determined according to the application, specific specifications, and the like of an article to be produced.

The base material, or at least the surface portion thereof, may be composed of a material originally having a hydroxyl group. Examples of the material include glass as well as metal (in particular, base metal) wherein a natural oxidized film or a thermal oxidized film is formed on the surface, ceramics, semiconductors, and the like. Alternatively, when the base material has an insufficient amount of a hydroxyl group or when the base material originally does not have a hydroxyl group as in resin and the like, a pre-treatment may be performed on the base material to thereby introduce or increase a hydroxyl group on the surface of the base material. Examples of such a pre-treatment include a plasma treatment (e.g., corona discharge) and ion beam irradiation. The plasma treatment can be suitably utilized to not only introduce or increase a hydroxyl group on the base material surface, but also clean the base material surface (remove foreign matter and the like). Another example of such a pre-treatment includes a method wherein a monolayer of a surface adsorbent having a carbon-carbon unsaturated bonding group is formed on the surface of the base material by a LB method (a Langmuir-Blodgett method), a chemical adsorption method, or the like beforehand, and thereafter cleaving the unsaturated bond under an atmosphere containing oxygen, nitrogen, or the like.

Alternatively, the base material may be that of which at least the surface consists of a material comprising other reactive group such as a silicone compound having one or more Si—H group or alkoxysilane.

Then, a layer of the surface-treating agent of the present disclosure is formed on the surface of the base material, this layer is post-treated as necessary, and thereby a layer is formed from the surface-treating agent of the present disclosure.

The layer of the surface-treating agent of the present disclosure can be formed by applying the above composition on the surface of the base material such that the composition coats the surface. The coating method is not limited. For example, a wet coating method and a dry coating method can be used.

Examples of the wet coating method include dip coating, spin coating, flow coating, spray coating, roll coating, gravure coating, and similar methods.

Examples of the dry coating method include deposition (usually, vacuum deposition), sputtering, CVD, and similar methods. Specific examples of the deposition method (usually, a vacuum deposition method) include resistive heating, high-frequency heating using electron beam, microwave or the like, ion beam, and similar methods. Specific examples of the CVD method include plasma-CVD, optical CVD, thermal CVD, and similar methods.

Furthermore, coating by an atmospheric pressure plasma method can be performed.

When using the wet coating method, the surface-treating agent of the present disclosure can be applied to the base material surface after being diluted with a solvent. From the viewpoint of the stability of the composition of the present disclosure and the volatility of solvents, the following solvents are preferably used: perfluoroaliphatic hydrocarbons having 5 to 12 carbon atoms (such as perfluorohexane, perfluoromethylcyclohexane, and perfluoro-1,3-dimethylcyclohexane); polyfluoroaromatic hydrocarbons (such as bis (trifluoromethyl)benzene); polyfluoroaliphatic hydrocarbons (such as $C_6F_{13}CH_2CH_3$ (such as Asahiklin® AC-6000 manufactured by Asahi Glass Co., Ltd., and 1,1,2,2,3,3,4-heptafluorocyclopentane (such as Zeorora (registered trademark) H manufactured by Zeon Corporation)); alkyl perfluoroalkyl ethers (the perfluoroalkyl group and the alkyl group may be linear or branched) such as hydrofluoroether (HFE) (such as perfluoropropylmethyl ether ($C_3F_7OCH_3$) (such as Novec™ 7000 manufactured by Sumitomo 3M Limited), perfluorobutyl methyl ether ($C_4F_9OCH_3$) (such as Novec™ 7100 manufactured by Sumitomo 3M Limited), perfluorobutyl ethyl ether ($C_4F_9OC_2H_5$) (such as Novec™ 7200 manufactured by Sumitomo 3M Limited), and perfluorohexyl methyl ether ($C_2F_5CF(OCH_3)C_3F_7$) (such as Novec™ 7300 manufactured by Sumitomo 3M Limited), or $CF_3CH_2OCF_2CHF_2$ (such as Asahiklin® AE-3000 manufactured by Asahi Glass Co., Ltd.)). One of these solvents can be used singly, or two or more can be used as a mixture. In particular, hydrofluoroether is preferable, and perfluorobutyl methyl ether ($C_4F_9OCH_3$) and/or perfluorobutyl ethyl ether ($C_4F_9OC_2H_5$) is particularly preferable.

When using the dry coating method, the surface-treating agent of the present disclosure may be directly subjected to the dry coating method, or may be diluted with the above solvent before being subjected to the dry coating method.

A layer of the surface-treating agent is preferably formed such that the surface-treating agent of the present disclosure coexists in the layer with a catalyst for hydrolysis and dehydrative condensation. Conveniently, in the case of a wet coating method, the surface-treating agent of the present disclosure is diluted with a solvent, and then, immediately before application to the base material surface, a catalyst may be added to the diluted solution of the surface-treating agent of the present disclosure. In the case of a dry coating method, the surface-treating agent of the present disclosure to which a catalyst has been added is directly used to a deposition (usually vacuum deposition) treatment, or a pellet-like material may be used to a deposition (usually vacuum deposition) treatment, wherein the pellets is obtained by impregnating a porous body of metal such as iron or copper with the surface-treating agent of the present disclosure to which the catalyst has been added.

The catalyst may be any suitable acid or base. The acid catalyst may be, for example, acetic acid, formic acid, or trifluoroacetic acid. The base catalyst may be, for example, ammonia or organic amine.

In one embodiment, a layer of the surface-treating agent of the present disclosure may be formed by applying or vacuum-depositing the surface-treating agent of the present disclosure to the base material surface. Thereafter, a treatment such as drying may be performed as necessary.

In the above-described manner, a layer derived from the surface-treating agent of the present disclosure is formed on the base material surface, and the article of the present disclosure is produced. The layer thus obtained has both high surface lubricity and high friction durability. The layer may have not only high friction durability but also have, depending on the formulation of the surface-treating agent used, water-repellency, oil-repellency, antifouling properties (e.g., preventing grime such as fingerprints from adhering), waterproof properties (preventing water from entering electronic components and the like), surface lubricity (or lubricity, for example, such as removability by wiping of grim such as fingerprints, and excellent tactile sensations to the fingers), and the like, and may be suitably used as a functional thin film.

That is to say, the present disclosure further relates to an optical material having the cured product in the outermost layer.

The optical material preferably includes a wide variety of optical materials in addition to optical materials relating to displays and the like as exemplified below: for example, displays such as cathode ray tubes (CRTs; e.g., PC monitors), liquid crystal displays, plasma displays, organic EL displays, inorganic thin-film EL dot matrix displays, rear projection displays, vacuum fluorescent displays (VFDs), field emission displays (FEDs); protective plates for such displays; and those obtained by performing an antireflection film treatment on their surfaces.

The article having a layer obtained according to the present disclosure may be, but is not limited to, an optical member. Examples of the optical member include lenses of glasses or the like; front surface protective plates, antireflection plates, polarizing plates, and anti-glare plates for displays such as PDPs and LCDs; touch panel sheets for devices such as mobile phones and personal digital assistants; disc surfaces of optical discs such as Blu-ray® discs, DVD discs, CD-Rs, and MOs; optical fibers; and display surfaces of watches and clocks.

The article having a layer obtained according to the present disclosure may be medical equipment or a medical material.

The thickness of the layer is not limited. The thickness of the layer in the case of an optical member is in the range of 1 to 50 nm, 1 to 30 nm, and preferably 1 to 15 nm, from the viewpoint of optical performance, surface lubricity, friction durability, and antifouling properties.

The article obtained by using the composition of the present disclosure (e.g., a surface-treating agent) has been described in detail above. The application and the method for using the polyether group-containing compound of the present disclosure or the composition containing the polyether group-containing compound, and the method for producing an article, are not limited to those exemplified above.

Embodiments have been described above, but it will be understood that various modifications can be made to embodiments and details without departing from the spirit and the scope of the claims.

EXAMPLES

The polyether group-containing compound of the present disclosure will now be described more specifically by way of the following Examples, but the present disclosure is not limited to the Examples. In the Examples, the occurrence order of the repeating units constituting perfluoropolyether is not limited.

Synthetic Example 1

First, 0.23 g of cyanuric chloride was dissolved in 3 ml of hexafluorobenzene. Then, 5.0 g of $CF_3CF_2CF_2$—$(OCF_2CF_2CF_2)_m OCF_2CH_2$—OH dissolved in hexafluorobenzene and 0.17 g of diisopropylethylamine were mixed, and the mixture was stirred at room temperature for 24 hours. To this reaction solution, 0.35 g of allylamine and 0.34 g of diisopropylethylamine were added, and the mixture was heated to 50° C. and stirred for 6 hours. The end point of the reaction was confirmed by 19F-NMR according to that the chemical shift of the hydroxyl group β position —$CF_2$— of $CF_3CF_2CF_2$—$(OCF_2CF_2CF_2)_m OCF_2CH_2$—OH shifted to a low magnetic field, and by 1H-NMR according to that the methylene proton at the amino group α-position of allylamine shifted to a low magnetic field. The reaction solution was concentrated, the concentrated solution was washed with acetone three times, and thus a polyether group-containing compound (A) was obtained.

Polyether group-containing compound (A):

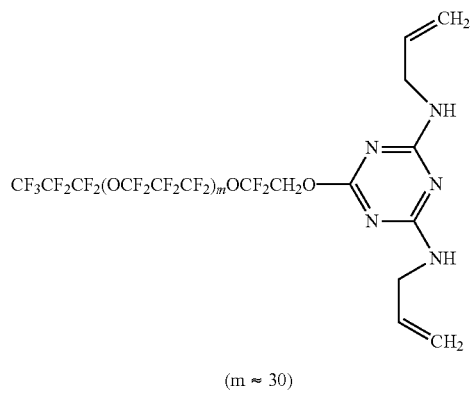

(m ≈ 30)

Synthetic Example 2

First, 5.0 g of the polyether group-containing compound (A) obtained in Synthetic Example 1, 20 ml of m-hexafluoroxylene, 0.02 g of triacetoxymethylsilane, and 0.06 ml of a xylene solution containing 2% Pt complex of 1,3-divinyl-1,1,3,3-tetramethyldisiloxane were each added, then 1.0 g of trichlorosilane was introduced, and the mixture was stirred at 10° C. for 30 minutes, then heated to 50° C., and stirred for 4 hours. Thereafter, volatiles were distilled off under reduced pressure, then a mixed solution of 0.1 g of methanol and 3.0 g of trimethyl orthoformate was added, and the mixture was heated to 50° C. and stirred for 3 hours. Thereafter, purification was performed, and thus 4.7 g of the following polyether group-containing compound (B) having trimethoxysilyl groups at terminals was obtained.

Polyether group-containing compound (B):

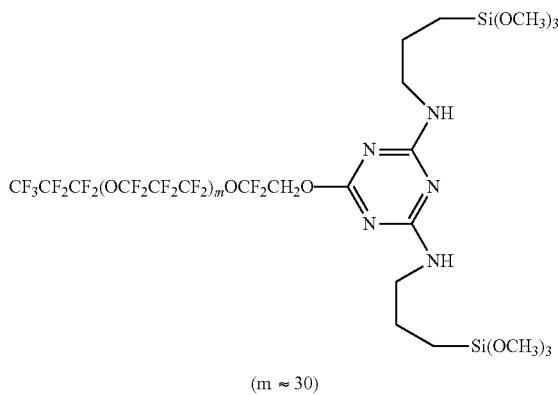

(m ≈ 30)

Synthetic Example 3

First, 0.17 g of cyanuric chloride was dissolved in 3 ml of hexafluorobenzene. Then, 2.5 g of $CF_3CF_2CF_2$—

$(OCF_2CF_2CF_2)_mOCF_2CH_2$—OH dissolved in hexafluorobenzene and 0.17 g of diisopropylethylamine were mixed, and the mixture was stirred at room temperature for 24 hours. Thereafter, 2.5 g of $CF_3CF_2CF_2$—$(OCF_2CF_2CF_2)_m$ $OCF_2CH_2$—OH and 0.17 g of diisopropylethylamine were added to the reaction solution, and the mixture was heated to 50° C. and stirred for 8 hours.

To this reaction solution, 0.35 g of 4-[2,2-di(2-propylenyl)]pentenylamine and 0.09 g of diisopropylethylamine were added, and the mixture was heated to 50° C. and stirred for 6 hours. The end point of the reaction was confirmed by $^{19}$F-NMR according to that the chemical shift of the hydroxyl group β position —$CF_2$— of $CF_3CF_2CF_2$—$(OCF_2CF_2CF_2)_nOCF_2CH_2$—OH shifted to a low magnetic field, and by $^1$H-NMR according to that the methylene proton at the amino group α-position of allylamine shifted to a low magnetic field. The reaction solution was concentrated, the concentrated solution was washed with acetone three times, and thus a polyether group-containing compound (C) was obtained.

Polyether group-containing compound (C):

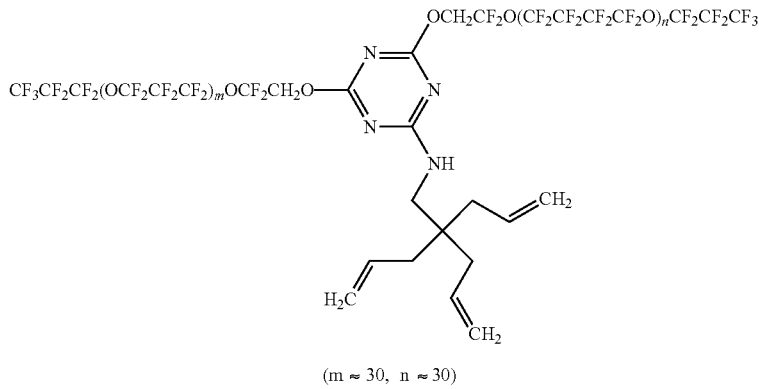

(m ≈ 30, n ≈ 30)

Synthetic Example 4

First, 5.0 g of the polyether group-containing compound (C) obtained in Synthetic Example 3, 20 ml of m-hexafluoroxylene, 0.03 g of triacetoxymethylsilane, and 0.1 ml of a xylene solution containing 2% Pt complex of 1,3-divinyl-1,1,3,3-tetramethyldisiloxane were each added, then 1.5 g of trichlorosilane was introduced, and the mixture was stirred at 10° C. for 30 minutes, then heated to 50° C., and stirred for 4 hours. Thereafter, volatiles were distilled off under reduced pressure, then a mixed solution of 0.1 g of methanol and 3.0 g of trimethyl orthoformate was added, and the mixture was heated to 50° ° C. and stirred for 3 hours. Thereafter, purification was performed, and thus 4.6 g of a polyether group-containing compound (D) having trimethoxysilyl groups at terminals was obtained.

Polyether group-containing compound (D):

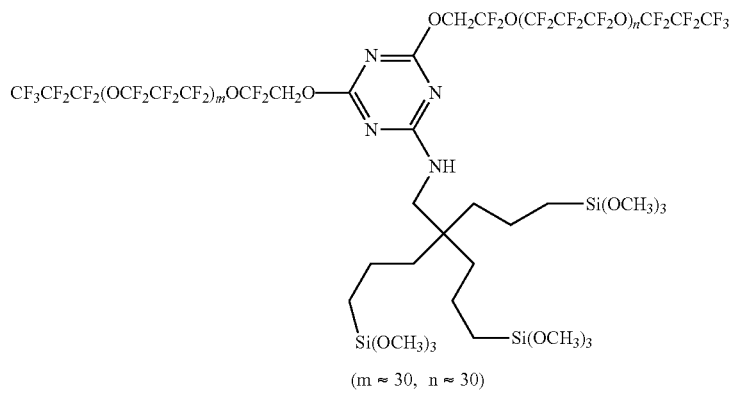

(m ≈ 30, n ≈ 30)

Synthetic Example 5

First, 0.17 g of cyanuric chloride was dissolved in 3 ml of hexafluorobenzene. Then, 1.25 g of $CF_3CF_2CF_2$—$(OCF_2CF_2CF_2)_mOCF_2CH_2$—OH dissolved in hexafluorobenzene and 0.17 g of diisopropylethylamine were added, and stirred at room temperature for 24 hours. Then, 1.25 g of $CF_3CF_2CF_2$—$(OCF_2CF_2CF_2)_nOCF_2CH_2$—OH and 0.17 g of diisopropylethylamine were added, and the mixture was heated to 50° C. and stirred for 8 hours.

Operations after adding 4-[2,2-di(2-propylenyl)]pentenylamine and diisopropylethylamine were carried out in the same manner as in Synthetic Example 3, and thus a polyether group-containing compound (E) was obtained.

Polyether group-containing compound (E):

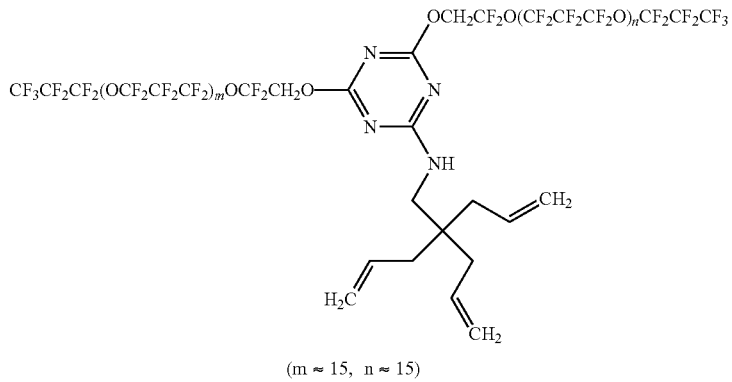

(m ≈ 15, n ≈ 15)

Synthetic Example 6

The same operations as in Synthetic Example 4 were carried out except that 2.5 g of the polyether group-containing compound (E) obtained in Synthetic Example 5 was used, and thus 2.6 g of a polyether group-containing compound (F) was obtained.

Polyether group-containing compound (F):

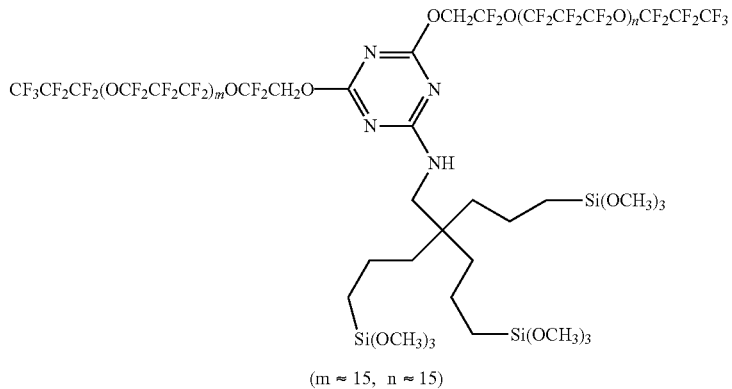

(m ≈ 15, n ≈ 15)

Synthetic Example 7

First, 0.17 g of cyanuric chloride was dissolved in 3 ml of hexafluorobenzene. Then, 2.5 g of $CF_3CF_2CF_2$—$(OCF_2CF_2CF_2)_mOCF_2CH_2$—OH dissolved in hexafluorobenzene and 0.17 g of diisopropylethylamine were mixed, and the mixture was stirred at room temperature for 24 hours. Thereafter, 1.25 g of $CF_3CF_2CF_2$—$(OCF_2CF_2CF_2)_nOCF_2CH_2$—OH and 0.17 g of diisopropylethylamine were added to the reaction solution, and the mixture was heated to 50° C. and stirred for 8 hours.

Operations after adding 4-[2,2-di(2-propylenyl)]pentenylamine and diisopropylethylamine were carried out in the same manner as in Synthetic Example 3, and thus a polyether group-containing compound (G) was obtained.

Polyether group-containing compound (G):

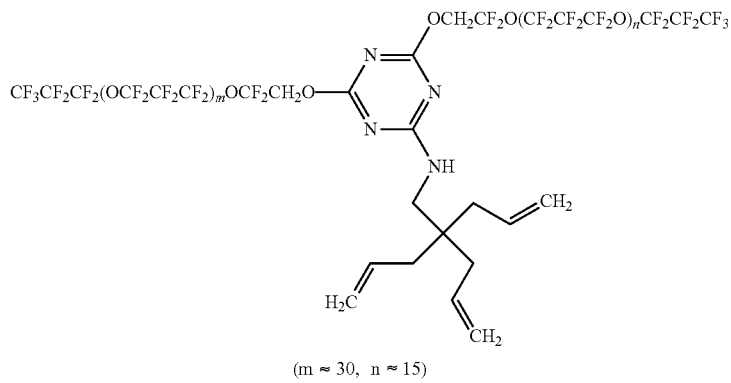

(m ≈ 30, n ≈ 15)

Synthetic Example 8

The same operations as in Synthetic Example 4 were carried out except that 3.8 g of the polyether group-containing compound (G) obtained in Synthetic Example 7 was used, and thus 3.5 g of a polyether group-containing compound (H) was obtained.

Polyether group-containing compound (H):

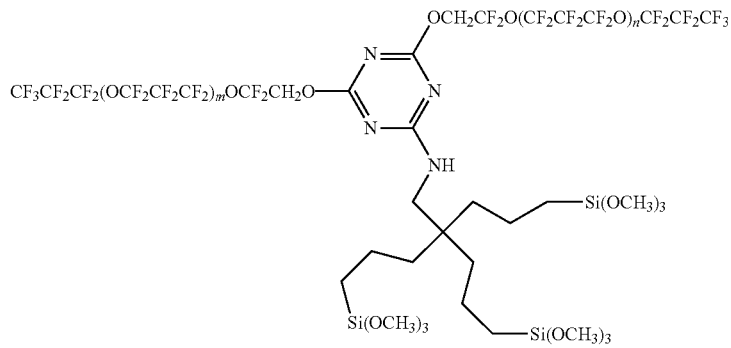

(m = 30, n = 15)

Synthetic Example 9

First, 0.17 g of cyanuric chloride was dissolved in 3 ml of hexafluorobenzene. Then, 2.5 g of $CF_3CF_2CF_2$—$(OCF_2CF_2CF_2)_m OCF_2CH_2$—OH dissolved in hexafluorobenzene and 0.17 g of diisopropylethylamine were mixed, and the mixture was stirred at room temperature for 24 hours. Thereafter, to this reaction solution, 0.7 g of 4-[2,2-di(2-propylenyl)]pentenylamine and 0.17 g of diisopropylethylamine were added, and the mixture was heated to 80° C. and stirred for 6 hours. The end point of the reaction was confirmed by 19F-NMR according to that the chemical shift of the hydroxyl group β position —$CF_2$— of $CF_3CF_2CF_2$—$(OCF_2CF_2CF_2)_m OCF_2CH_2$—OH shifted to a low magnetic field, and by $^1$H-NMR according to that the methylene proton at the amino group α-position of allylamine shifted to a low magnetic field. The reaction solution was concentrated, the concentrated solution was washed with acetone three times, and thus a polyether group-containing compound (I) was obtained.

Polyether group-containing compound (I):

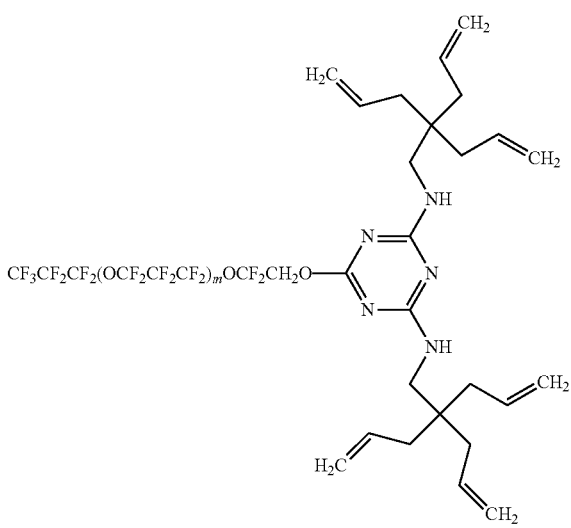

(m = 30)

Synthetic Example 10

The same operations as in Synthetic Example 4 were carried out except that 3.9 g of the polyether group-containing compound (I) obtained in Synthetic Example 9 was used, and thus 4.0 g of a polyether group-containing compound (J) was obtained.

Polyether group-containing compound (J):

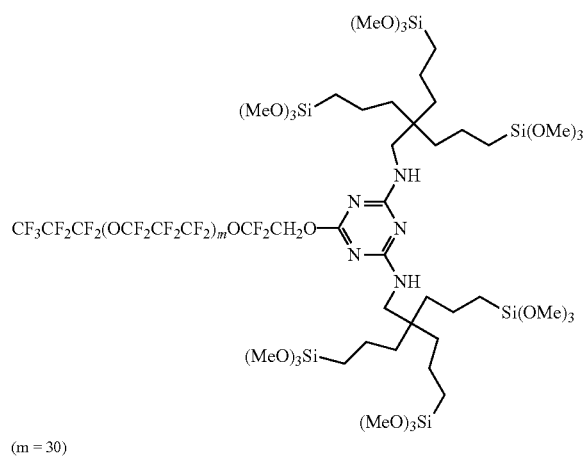

(m = 30)

Synthetic Example 11

First, 0.23 g of cyanuric chloride was dissolved in 3 ml of hexafluorobenzene. Then, 5.0 g of $CF_3$—$(OCF_2CF_2)_m$—$(OCF_2)_n$—$CH_2OH$ (m≈22, n≈34) dissolved in hexafluorobenzene and 0.17 g of diisopropylethylamine were mixed, and the mixture was stirred at room temperature for 24 hours. To this reaction solution, 0.35 g of allylamine and 0.34 g of diisopropylethylamine were added, and the mixture was heated to 50° C. and stirred for 6 hours. The end point of the reaction was confirmed by 19F-NMR according to that the chemical shift of the hydroxyl group B position —$CF_2$— of $CF_3$—$(OCF_2CF_2)_m$—$(OCF_2)_n$—$CH_2OH$ shifted to a low magnetic field, and by $^1$H-NMR according to that the methylene proton at the amino group α-position of allylamine shifted to a low magnetic field. The reaction solution was concentrated, the concentrated solution was washed with acetone three times, and thus a polyether group-containing compound (K) was obtained.

Polyether group-containing compound (K):

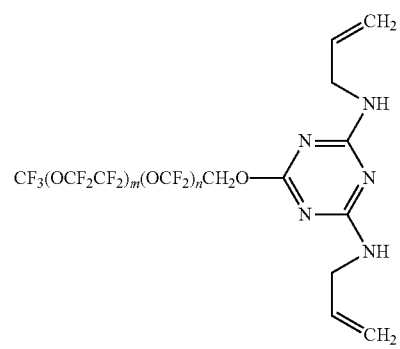

Synthetic Example 12

First, 5.0 g of the polyether group-containing compound (K) obtained in Synthetic Example 11, 20 ml of m-hexafluoroxylene, 0.02 g of triacetoxymethylsilane, and 0.06 ml of a xylene solution containing 2% Pt complex of 1,3-divinyl-1,1,3,3-tetramethyldisiloxane were each added, then 1.0 g of trichlorosilane was introduced, and the mixture was stirred at 10° C. for 30 minutes, then heated to 50° C., and stirred for 4 hours. Thereafter, volatiles were distilled off under reduced pressure, then a mixed solution of 0.1 g of methanol and 3.0 g of trimethyl orthoformate was added, and the mixture was heated to 50° C. and stirred for 3 hours. Thereafter, purification was performed, and thus 4.2 g of the following polyether group-containing compound (L) having trimethoxysilyl groups at terminals was obtained.

Polyether group-containing compound (L):

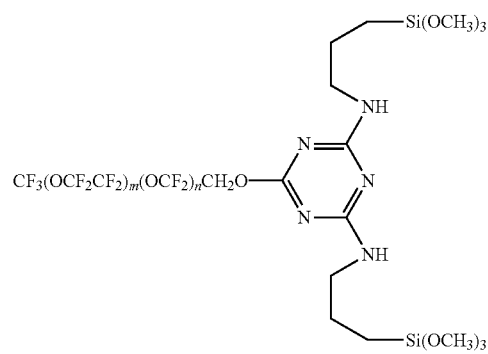

Synthetic Example 13

First, 0.17 g of cyanuric chloride was dissolved in 3 ml of hexafluorobenzene. Then, 2.5 g of $CF_3$—$(OCF_2CF_2)_m$—$(OCF_2)_n$—$CH_2OH$ (m≈22, n≈34) dissolved in hexafluorobenzene and 0.17 g of diisopropylethylamine were mixed, and the mixture was stirred at room temperature for 24 hours. Thereafter, 2.5 g of CF$_3$—(OCF$_2$CF$_2$)$_m$—(OCF$_2$)$_n$—CH$_2$OH (m=22, n≈34) and 0.17 g of diisopropylethylamine were added to the reaction solution, and the mixture was heated to 50° C. and stirred for 8 hours.

To this reaction solution, 0.35 g of 4-[2,2-di(2-propylenyl)]pentenylamine and 0.09 g of diisopropylethylamine were added, and the mixture was heated to 50° C. and stirred for 6 hours. The end point of the reaction was confirmed by 19F-NMR according to that the chemical shift of the hydroxyl group β position —CF$_2$— of CF$_3$—(OCF$_2$CF$_2$)$_m$—(OCF$_2$)$_n$—CH$_2$OH shifted to a low magnetic field, and by $^1$H-NMR according to that the methylene proton at the amino group α-position of allylamine shifted to a low magnetic field. The reaction solution was concentrated, the concentrated solution was washed with acetone three times, and thus a polyether group-containing compound (M) was obtained.

Polyether group-containing compound (M):

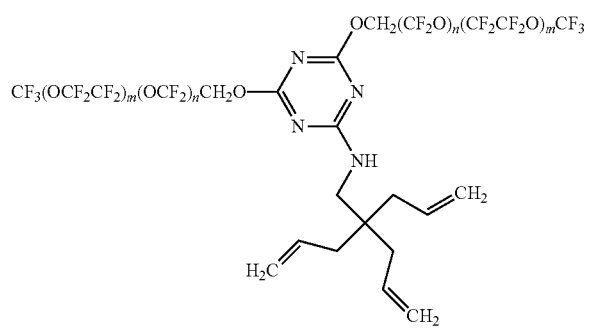

Synthetic Example 14

First, 5.0 g of the polyether group-containing compound (M) obtained in Synthetic Example 13, 20 ml of m-hexafluoroxylene, 0.03 g of triacetoxymethylsilane, and 0.1 ml of a xylene solution containing 2% Pt complex of 1,3-divinyl-1,1,3,3-tetramethyldisiloxane were each added, then 1.5 g of trichlorosilane was introduced, and the mixture was stirred at 10° C. for 30 minutes, then heated to 50° C., and stirred for 4 hours. Thereafter, volatiles were distilled off under reduced pressure, then a mixed solution of 0.1 g of methanol and 3.0 g of trimethyl orthoformate was added, and the mixture was heated to 50° C. and stirred for 3 hours. Thereafter, purification was performed, and thus 4.0 g of a polyether group-containing compound (N) having trimethoxysilyl groups at terminals was obtained.

Polyether group-containing compound (N):

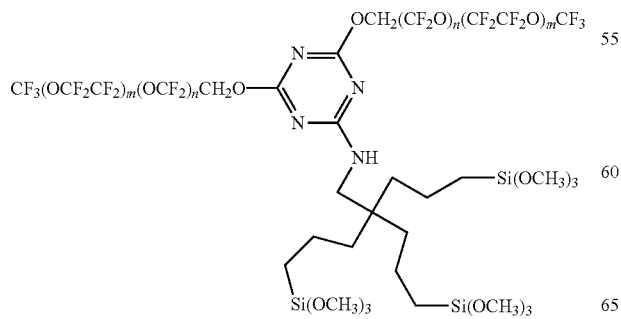

Synthetic Example 15

First, 0.17 g of cyanuric chloride was dissolved in 3 ml of hexafluorobenzene. Then, 2.5 g of CF$_3$—(OCF$_2$CF$_2$)$_m$—(OCF$_2$)$_n$—CH$_2$OH (m≈22, n≈34) dissolved in hexafluorobenzene and 0.17 g of diisopropylethylamine were mixed, and the mixture was stirred at room temperature for 24 hours. Thereafter, to this reaction solution, 0.7 g of 4-[2,2-di(2-propylenyl)]pentenylamine and 0.17 g of diisopropylethylamine were added, and the mixture was heated to 80° C. and stirred for 6 hours. The end point of the reaction was confirmed by 19F-NMR according to that the chemical shift of the hydroxyl group β position —CF$_2$— of CF$_3$CF$_2$CF$_2$—(OCF$_2$CF$_2$CF$_2$)$_m$OCF$_2$CH$_2$—OH shifted to a low magnetic field, and by 1H-NMR according to that the methylene proton at the amino group α-position of allylamine shifted to a low magnetic field. The reaction solution was concentrated, the concentrated solution was washed with acetone three times, and thus a polyether group-containing compound (O) was obtained.

Polyether group-containing compound (O):

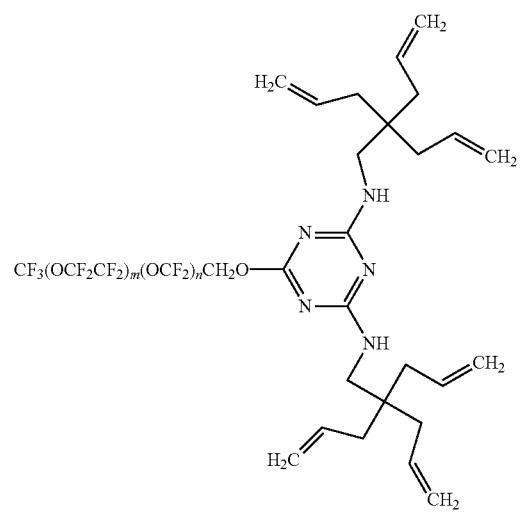

Synthetic Example 16

The same operations as in Synthetic Example 4 were carried out except that 3.9 g of the polyether group-containing compound (O) obtained in Synthetic Example 15 was used, and thus 3.5 g of a polyether group-containing compound (P) was obtained.

Polyether group-containing compound (P):

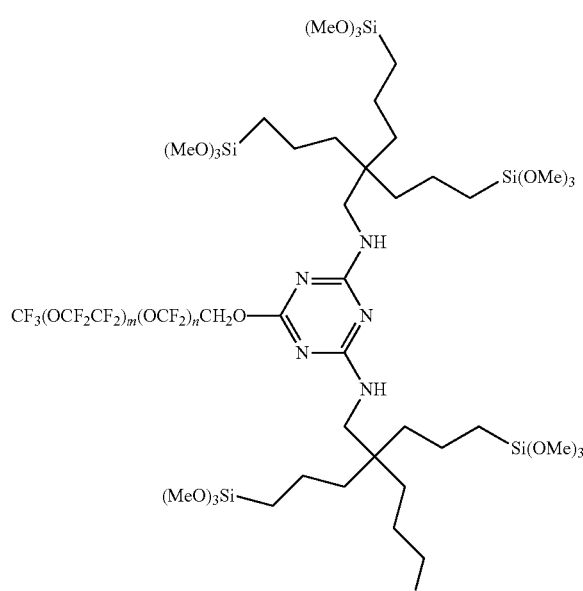

Example 1

The polyether group-containing compound (B) obtained in Synthetic Example 2 was dissolved in hydrofluoroether (Novec HFE-7300, manufactured by 3M) so as to have a concentration of 1 mass %, and thus a surface-treating agent (1) was prepared.

Example 2

The polyether group-containing compound (D) obtained in Synthetic Example 4 was dissolved in hydrofluoroether (Novec HFE-7300, manufactured by 3M) so as to have a concentration of 1 mass %, and thus a surface-treating agent (2) was prepared.

Example 3

The polyether group-containing compound (F) obtained in Synthetic Example 6 was dissolved in hydrofluoroether (Novec HFE-7300, manufactured by 3M) so as to have a concentration of 1 mass %, and thus a surface-treating agent (3) was prepared.

Example 4

The polyether group-containing compound (H) obtained in Synthetic Example 8 was dissolved in hydrofluoroether (Novec HFE-7300, manufactured by 3M) so as to have a concentration of 1 mass %, and thus a surface-treating agent (4) was prepared.

Example 5

The polyether group-containing compound (J) obtained in Synthetic Example 10 was dissolved in hydrofluoroether (Novec HFE-7300, manufactured by 3M) so as to have a concentration of 1 mass %, and thus a surface-treating agent (5) was prepared.

Example 6

The polyether group-containing compound (L) obtained in Synthetic Example 12 was dissolved in hydrofluoroether (Novec HFE-7300, manufactured by 3M) so as to have a concentration of 1 mass %, and thus a surface-treating agent (6) was prepared.

Example 7

The polyether group-containing compound (N) obtained in Synthetic Example 14 was dissolved in hydrofluoroether (Novec HFE-7300, manufactured by 3M) so as to have a concentration of 1 mass %, and thus a surface-treating agent (7) was prepared.

Example 8

The polyether group-containing compound (P) obtained in Synthetic Example 16 was dissolved in hydrofluoroether (Novec HFE-7300, manufactured by 3M) so as to have a concentration of 1 mass, and thus a surface-treating agent (8) was prepared.

(Comparative Examples 1 and 2)

Comparative surface-treating agents (1) and (2) were respectively prepared in the same manner as in Example 4 except that the following control compounds (1) and (2) were used in place of the polyether group-containing compound (H).

Control Compound (1)
$CF_3CF_2CF_2\text{—}(OCF_2CF_2CF_2)_{23}\text{—}$
$OCF_2CF_2CH_2OCH_2CH_2CH_2Si(OCH_3)_3$ Control Compound (2)
$CF_3CF_2CF_2CF_2CF_2CF_2CH_2CH_2Si(OCH_2CH_3)_3$ (Static Contact Angle)

The static contact angle was measured by the following method using a fully automatic contact angle meter Drop-Master 700 (manufactured by Kyowa Interface Science Co., Ltd.).

<Method for Measuring Static Contact Angle>

The static contact angle was obtained by dripping 2 μL of water or n-hexadecane from a microsyringe onto a horizontally placed base material and taking a still image with a video microscope 1 second after the dripping.

(Formation of Cured Film)

The surface-treating agents (1) to (8) and the comparative surface-treating agents (1) to (2) were used to form cured films as follows.

A surface-treating agent or a comparative surface-treating agent was applied to a chemically tempered glass ("Gorilla" glass, manufactured by Corning Incorporated, thickness 0.7 mm) using a spin coater.

The spin coating conditions were 300 rpm for 3 seconds and 2000 rpm for 30 seconds.

The coated glass was heated at 150° C. for 30 minutes in a thermostatic oven in air to form a cured film.

[Evaluation of Cured Film Properties]

Properties of the resulting cured film were evaluated as follows.

<Static Contact Angle>

(Initial Evaluation)

First, as an initial evaluation, after the cured film was formed, the static water contact angle of the surface with which nothing was brought into contact yet was measured.

(Evaluation after Wiping with Ethanol)

The cured film was wiped back and forth five times with Kimwipe (trade name, manufactured by Jujo Kimberly Co., Ltd.) sufficiently soaked with ethanol, and dried. After drying, the static water contact angle of the cured film was measured.

<Fingerprint Adherability and Removability by Wiping>
(Fingerprint Adherability)

A finger was pressed against a cured film formed using a surface-treating agent or a comparative surface-treating agent, and how easily a fingerprint adheres was visually judged. Evaluations were made according to the following criteria:

A: Fingerprint unlikely adhered, or not noticeable even when adhered.

B: Adhered fingerprint was little, but fingerprint sufficiently confirmed.

C: Fingerprint adhered as clearly as fingerprint on untreated glass base material.

(Fingerprint Removability by Wiping)

After the fingerprint adherability test, the adhered fingerprint was wiped off back and forth five times with Kimwipe (trade name, manufactured by Jujo Kimberly Co., Ltd.), and how easily the adhered fingerprint was wiped off was visually judged. Evaluations were made according to the following criteria:

A: Fingerprint completely wiped off.
B: Fingerprint wiping marks remained.
C: Fingerprint wiping marks spread, and difficult to remove.

The results of the series of evaluations are summarized in Table 1 below.

TABLE 1

| Treating agent | | Contact angle (degree) | | Fingerprint adherability and removability by wiping | |
|---|---|---|---|---|---|
| | | Initial evaluation | After wiping with ethanol | Fingerprint adherability | Fingerprint removability by wiping |
| Surface-treating agent (1) | Example 1 | 118 | 118 | A | A |
| Surface-treating agent (2) | Example 2 | 110 | 110 | A | A |
| Surface-treating agent (3) | Example 3 | 115 | 115 | A | A |
| Surface-treating agent (4) | Example 4 | 117 | 117 | A | A |
| Surface-treating agent (5) | Example 5 | 119 | 119 | A | A |
| Surface-treating agent (6) | Example 6 | 116 | 116 | A | A |
| Surface-treating agent (7) | Example 7 | 115 | 115 | A | A |
| Surface-treating agent (8) | Example 8 | 115 | 115 | A | A |
| Comparative surface-treating agent (1) | Comparative Example 1 | 113 | 112 | A | B |
| Comparative surface-treating agent (2) | Comparative Example 2 | 105 | 103 | B | C |

The contact angles of the cured films formed using the surface-treating agents (1) to (8) were not decreased even when the films were wiped using ethanol. On the other hand, the contact angles of the cured films formed using the comparative surface-treating agents (1) and (2) were decreased when the films were wiped using ethanol. This is considered to be because the cured films formed with the comparative surface-treating agent (1) and (2) have poor chemical resistance (solvent resistance).

Accordingly, it was demonstrated that the surface-treating agents (1) to (8) are superior to the comparative surface-treating agents. The cured films formed using the surface-treating agents (1) to (8) received good evaluations with respect to both fingerprint adherability and fingerprint removability by wiping.

The present disclosure provides [1] to below.

[1] A polyether group-containing compound of formula (I):

wherein
one or two R— groups are represented by $(Rf-X^{f1}-PE-X^{f2})_\alpha-X^1-$, and one or two R— groups are represented by $R^{Si}-$;

the total number of $(Rf-X^{f1}-PE-X^{f2})_\alpha-X^1-$ and $R^{Si}-$ is 3;

$\alpha$ is an integer of 1 to 9;

Rf is independently at each occurrence an alkyl group having 1 to 16 carbon atoms, optionally substituted with one or more fluorine atoms;

PE is each independently at each occurrence a group represented by formula: $-OC_6F_{12})_a-(OC_5F_{10})_b-(OC_4F_8)_c-(OC_3X^{10}{}_6)_d-(OC_2F_4)_e-(OCF_2)_f-$ wherein a, b, c, d, e, and f are each independently an integer of 0 or more and 200 or less, the sum of a, b, c, d, e, and f is at least 1, the occurrence order of the respective repeating units enclosed in parentheses provided with a, b, c, d, e, or f is not limited in the formula, and $X^{10}$ is each independently at each occurrence a hydrogen atom, a fluorine atom, or a chlorine atom;

$X^{f1}$ is represented by $(X^{f11})_z$;

$X^{f11}$ is an alkylene group having 1 to 6 carbon atoms wherein a hydrogen atom is optionally replaced with a fluorine atom;

z is each independently at each occurrence 0 or 1;

$X^{f2}$ is represented by $(O)_y$ or $(NH)_y$;

y is each independently at each occurrence 0 or 1;

$X^1$ is each independently at each occurrence a single bond, an oxygen atom, a nitrogen atom, a sulfur atom, —NH—, —SO$_2$NH—, —SO$_2$—, or a di- to decavalent organic group;

$R^{Si}-$ is each independently at each occurrence represented by any of the following formulae (A1) to (A4):

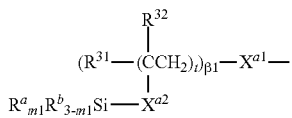
(A1)

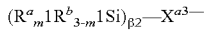
(A2)

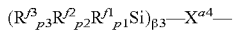
(A3)

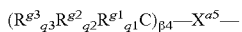
(A4)

$R^a$ is each independently at each occurrence a hydroxyl group or a hydrolyzable group;

$R^b$ is each independently at each occurrence a hydrogen atom or an alkyl group having 1 to 20 carbon atoms;

m1 is each independently at each occurrence an integer of 0 to 3;

$X^{a1}$, $X^{a3}$, $X^{a4}$, and $X^{a5}$ is each independently at each occurrence a single bond, an oxygen atom, a nitrogen atom, a sulfur atom, —NH—, —SO$_2$NH—, —SO$_2$—, or a di- to decavalent organic group;

$X^{a2}$ is a single bond or a divalent organic group;

β1, β2, β3, and β4 are each independently at each occurrence an integer of 1 to 9;

t is each independently at each occurrence an integer of 2 to 10;

$R^{31}$ is each independently at each occurrence a hydrogen atom or a halogen atom;

$R^{32}$ is each independently at each occurrence a hydrogen atom or a monovalent organic group;

in formula (A1), there is at least one $R^a_{m1}R^b_{3-m1}$Si— wherein m1 is 1 to 3, and in formula (A2), there is at least one $R^a_{m1}R^b_{3-m1}$Si— wherein m1 is 1 to 3;

$R^{f1}$ is each independently at each occurrence $R^{41}_{r1}R^{42}_{r2}R^{43}_{r3}$Si-$Z^1$—;

$Z^1$ is each independently at each occurrence an oxygen atom or a divalent organic group;

$R^{41}$ is each independently at each occurrence $R^{f1'}$;

$R^{f1'}$ has the same definition as that of $R^{f1}$;

in $R^{f1}$, the number of Si atoms linearly connected via the group $Z^1$ is up to 5;

$R^{42}$ is each independently at each occurrence a hydroxyl group or a hydrolyzable group;

$R^{43}$ is each independently at each occurrence a hydrogen atom or a monovalent organic group;

r1 is each independently at each occurrence an integer of 0 to 3;

r2 is each independently at each occurrence an integer of 0 to 3;

r3 is each independently at each occurrence an integer of 0 to 3;

in each $R^{41}_{r1}R^{42}_{r2}R^{43}_{r3}$Si-$Z^1$—, the sum of r1, r2, and r3 is 3;

$R^{f2}$ is each independently at each occurrence a hydroxyl group or a hydrolyzable group;

$R^{f3}$ is each independently at each occurrence a hydrogen atom or a monovalent organic group;

p1 is each independently at each occurrence an integer of 0 to 3;

p2 is each independently at each occurrence an integer of 0 to 3;

p3 is each independently at each occurrence an integer of 0 to 3;

in each $R^{f3}_{p3}R^{f2}_{p2}R^{f1}_{p1}$Si—, the sum of p1, p2, and p3 is 3, and in formula (A3), there are at least two Si atoms to which a hydroxyl group or a hydrolyzable group binds;

$R^{g1}$ is each independently at each occurrence $R^{51}_{s1}R^{52}_{s2}R^{53}_{s3}$C-$Z^2$—;

$Z^2$ is each independently at each occurrence an oxygen atom or a divalent organic group;

$R^{51}$ is each independently at each occurrence $R^{g1'}$;

$R^{g1'}$ has the same definition as that of $R^{g1}$;

in $R^{g1}$, the number of C atoms linearly connected via the group $Z^2$ is up to 5;

$R^{52}$ is each independently at each occurrence $R^a_{m1}R^b_{3-m1}$Si-$Z^3$—;

$Z^3$ is each independently at each occurrence an oxygen atom or a divalent organic group;

$R^{53}$ is each independently at each occurrence a hydrogen atom, a hydroxyl group, or a monovalent organic group;

s1 is each independently at each occurrence an integer of 0 to 3;

s2 is each independently at each occurrence an integer of 0 to 3;

s3 is each independently at each occurrence an integer of 0 to 3;

in each $R^{51}_{s1}R^{52}_{s2}R^{53}_{s3}$C-$Z^2$—, the sum of s1, s2, and s3 is 3;

$R^{g2}$ is each independently at each occurrence $R^a_{m1}R^b_{3-m1}$Si-$Z^4$—;

$Z^4$ is each independently at each occurrence an oxygen atom or a divalent organic group;

$R^{g3}$ is each independently at each occurrence a hydrogen atom, a hydroxyl group, or a monovalent organic group;

q1 is each independently at each occurrence an integer of 0 to 3;

q2 is each independently at each occurrence an integer of 0 to 3; and q3 is each independently at each occurrence an integer of 0 to 3;

in each $R^{g3}_{q3}R^{g2}_{q2}R^{g1}_{q1}$C—, the sum of q1, q2, and q3 is 3, and in formula (A4), there are at least two $R^a_{m1}R^b_{3-m1}$Si— wherein m1 is 1 to 3.

[2] The polyether group-containing compound according to [1], wherein $X^1$ is each independently at each occurrence (—($R^{11}$)$_{n16}$—)$_2$N—($R^{12}$)$_{n17}$—, —($R^{11}$)$_{n16}$—$X^{11}$—($R^{12}$)$_{n17}$—, or —$R^{13}$—, wherein $R^{11}$ is each independently at each occurrence —(CH$_2$)$_{n11}$—, an o-, m-, or p-phenylene group, which may be substituted with one or more fluorine atoms;

n11 is an integer of 1 to 20;

$R^{12}$ is each independently at each occurrence —(CH$_2$)$_{n12}$—, an o-, m-, or p-phenylene group, which may be substituted with one or more fluorine atoms;

n12 is an integer of 1 to 20;

n16 is 0 or 1;

n17 is 0 or 1;

the sum of n16 and n17 is 1 or more;

$X^{11}$ is each independently at each occurrence —O—, —(OR$^{61}$)$_{n14}$—, —S—, —C(=O)—, —C(=O) O—, —O—C(=O)—, —O—C(=O)—O—, —Si(R$^{62}$)$_2$—, —(Si(R$^{62}$)$_2$O)$_{n15}$—Si(R$^{62}$)$_2$—, —NR$^3$C(=O)—, —C(=O)NR$^3$—, —NR$^3$C(=O)NR$^3$—, —NR$^3$C(=O) O—, —O—C(=O)NR$^3$—, —NR$^3$—, —SO$_2$NR$^3$—, or —SO$_2$—;

$R^{61}$ is each independently at each occurrence a C$_{1-6}$ alkylene group;

n14 is each independently at each occurrence an integer of 1 to 5;

$R^{62}$ is each independently at each occurrence a phenyl group, a $C_{1-6}$ alkyl group, or a $C_{1-6}$ alkoxy group;

n15 is each independently at each occurrence an integer of 1 to 100;

$R^3$ is each independently at each occurrence a hydrogen atom, a phenyl group, or an alkyl group having 1 to 6 carbon atoms;

$R^{13}$ is —$(CH_2)_{n13}$—; and n13 is an integer of 1 to 20.

[3] The polyether group-containing compound according to [1] or [2], wherein a is 2.

[4] The polyether group-containing compound according to [1] or [2], wherein a is 1.

[5] The polyether group-containing compound according to any one of [1] to [4], wherein $X^{a1}$, $X^{a3}$, $X^{a4}$, and $X^{a5}$ are each independently at each occurrence (—$(R^{71})_{n21}$—$)_2$N—$(R^{72})_{n22}$—, —$(R^{71})_{n21}$—$X^3$—$(R^{72})_{n22}$—, —$R^{73}$—, or —Y—O—, wherein $R^{71}$ is each independently at each occurrence —$(CH_2)_{n23}$—, an o-, m-, or p-phenylene group, which may be substituted with one or more fluorine atoms;

n23 is each independently at each occurrence an integer of 1 to 20;

$R^{72}$ is each independently at each occurrence —$(CH_2)_{n24}$—, an o-, m-, or p-phenylene group, which may be substituted with one or more fluorine atoms;

n24 is each independently at each occurrence an integer of 1 to 20;

n21 is each independently at each occurrence 0 or 1;
n22 is each independently at each occurrence 0 or 1;
the sum of n21 and n22 is 1 or more;

$X^3$ is each independently at each occurrence —O—, —$(OR^{74})_{n25}$—, —S—, —C(=O)—, —C(=O) O—, —O—C(=O)—, —O—C(=O)—O—, —Si$(R^{75})_2$—, —(Si$(R^{75})_2$O)$_{n26}$—Si$(R^{75})_2$—, —NR$^3$C(=O)—, —C(=O)NR$^3$—, —NR$^3$C(=O) O—, —O—C(=O) NR$^3$—, —NR$^3$—, —SO$_2$NR$^3$—, or —SO$_2$—;

$R^{74}$ is each independently at each occurrence a $C_{1-6}$ alkylene group;

n25 is each independently at each occurrence an integer of 1 to 5;

$R^{75}$ is each independently at each occurrence a phenyl group, a $C_{1-6}$ alkyl group, or a $C_{1-6}$ alkoxy group;

n26 is each independently at each occurrence an integer of 1 to 100;

$R^3$ is each independently at each occurrence a hydrogen atom, a phenyl group, or an alkyl group having 1 to 6 carbon atoms;

$R^{73}$ is each independently at each occurrence —$(CH_2)_{n27}$—;

n27 is an integer of 1 to 20; and

Y is a di- to hexavalent hydrocarbon group and has a silicon atom and/or a siloxane bond.

[6] The polyether group-containing compound according to any one of [1] to [5], wherein m1 is 2 or 3.

[7] The polyether group-containing compound according to any one of [1] to [6], wherein m1 is 3.

[8] The polyether group-containing compound according to any one of [1] to [7], wherein p1 is 3, and r2 is 3.

[9] The polyether group-containing compound according to any one of [1] to [8], wherein in formula (A4), q2 is 3, and m1 is 3.

The polyether group-containing compound according to any one of [1] to [9], wherein β1, β2, β3, or β4 is 1.

The polyether group-containing compound according to any one of [1] to [10], wherein Rf is a perfluoroalkyl group having 1 to 16 carbon atoms.

The polyether group-containing compound according to any one of [1] to [11], wherein PE is a group represented by any of the following formulae (a) to (c):

wherein d is an integer of 1 to 200;

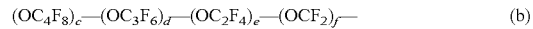

wherein c and d are each independently an integer of 0 or more and 30 or less;

e and f are each independently an integer of 1 or more and 200 or less;

the sum of c, d, e, and f is an integer of 10 or more and 200 or less; and the occurrence order of the respective repeating units enclosed in parentheses provided with a subscript c, d, e, or f is not limited in the formula; and

wherein $R^6$ is $OCF_2$ or $OC_2F_4$;

$R^7$ is a group selected from $OC_2F_4$, $OC_3F_6$, $OC_4F_8$, $OC_5F_{10}$, and $OC_6F_{12}$, or is a combination of two or three groups selected from these groups; and g is an integer of 2 to 100.

[13] A surface-treating agent comprising the polyether group-containing compound according to any one of [1] to [12].

[14] The surface-treating agent according to [13], further comprising a solvent.

[15] The surface-treating agent according to or [14], which is used as an antifouling coating agent or a waterproof coating agent.

[16] An article comprising a base material and a layer on a surface of the base material, wherein the layer is formed of the polyether group-containing compound according to any one of [1] to or the surface-treating agent according to any one of to [15].

[17] The article according to [16], which is an optical member.

INDUSTRIAL APPLICABILITY

The present disclosure can be suitably used to form a surface-treating layer on the surfaces of a large variety of base materials.

The invention claimed is:

1. A polyether group-containing compound of the formula (I):

wherein
one or two R— groups are represented by (Rf-$X^{f1}$-PE-$X^{f2}$)$_\alpha$—$X^1$—, and one or two R— groups are represented by $R^{Si}$—;

the total number of $(Rf\text{-}X^{f1}\text{-}PE\text{-}X^{f2})_\alpha\text{-}X^1\text{-}$ and $R^{Si}\text{-}$ is 3;

α is an integer of 1 to 9;

Rf is independently at each occurrence an alkyl group having 1 to 16 carbon atoms, optionally substituted with one or more fluorine atoms;

PE is each independently at each occurrence a group represented by formula: $-(OC_6F_{12})_a-(OC_5F_{10})_b-(OC_4F_8)_c-(OC_3X^{10}{}_6)_d-(OC_2F_4)_e-(OCF_2)_f-$ wherein a, b, c, d, e, and f are each independently an integer of 0 or more and 200 or less, the sum of a, b, c, d, e, and f is at least 1, the occurrence order of the respective repeating units enclosed in parentheses provided with a, b, c, d, e, or f is not limited in the formula, and $X^{10}$ is each independently at each occurrence a hydrogen atom, a fluorine atom, or a chlorine atom;

$X^{f1}$ is represented by $(X^{f11})_z$;

$X^{f11}$ is an alkylene group having 1 to 6 carbon atoms wherein a hydrogen atom is optionally replaced with a fluorine atom;

z is each independently at each occurrence 0 or 1;

$X^{f2}$ is represented by $(O)_y$ or $(NH)_y$;

y is each independently at each occurrence 0 or 1;

$X^1$ is each independently at each occurrence $(-(R^{11})_{n16}-)_2N-(R^{12})_{n17}-$, $-(R^{11})_{n16}-X^{11}-$, or $-R^{13}-$, $R^{11}$ each independently at each occurrence represents $-(CH_2)_{n11}-$, an o-, m-, or p-phenylene group which may be substituted with one or more fluorine atoms;

n11 is an integer of 1 to 20;

$R^{12}$ each independently at each occurrence represents $-(CH_2)_{n12}-$, an o-, m-, or p-phenylene group which may be substituted with one or more fluorine atoms;

n12 is an integer of 1 to 20;

$X^{11}$ is each independently at each occurrence $-O-$, $-(OR^{61})_{n14}-$, $-S-$, $-C(=O)-$, $-C(=O)O-$, $-O-C(=O)-$, $-O-C(=O)-O-$, $-Si(R^{62})_2-$, $-(Si(R^{62})_2O)_{n15}-Si(R^{62})_2-$, $-NR^3C(=O)-$, $-C(=O)NR^3-$, $-NR^3C(=O)NR^3-$, $-NR^3C(=O)O-$, $-O-C(=O)NR^3-$, $-NR^3-$, $-SO_2NR^3-$, or $-SO_2-$;

$R^{61}$ is each independently at each occurrence a $C_{1-6}$ alkylene group;

n14 is each independently at each occurrence an integer of 1 to 5;

$R^{62}$ is each independently at each occurrence a phenyl group, a $C_{1-6}$ alkyl group, or a $C_{1-6}$ alkoxy group;

n15 is each independently at each occurrence an integer of 1 to 100;

$R^3$ is each independently at each occurrence a hydrogen atom, a phenyl group, or an alkyl group having 1 to 6 carbon atoms;

n16 each independently at each occurrence is 0 or 1;

n17 is 0 or 1;

$R^{13}$ is each independently at each occurrence $-(CH_2)_{n13}-$;

n13 is an integer of 1 to 20;

$R^{Si}-$ is each independently at each occurrence represented by any of the following formulae (A1) to (A4):

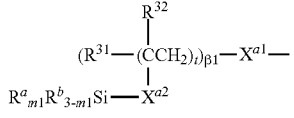

(A1)

$(R^a{}_m1R^b{}_{3-m1}Si)_{\beta 2}-X^{a3}-$ (A2)

$(R^{f3}{}_{p3}R^{f2}{}_{p2}R^{f1}{}_{p1}Si)_{\beta 3}-X^{a4}-$ (A3)

$(R^{g3}{}_{q3}R^{g2}{}_{q2}R^{g1}{}_{q1}C)_{\beta 4}-X^{a5}-$ (A4)

$R^a$ is each independently at each occurrence a hydroxyl group or a hydrolyzable group;

$R^b$ is each independently at each occurrence a hydrogen atom or an alkyl group having 1 to 20 carbon atoms;

m1 is each independently at each occurrence an integer of 0 to 3;

$X^{a1}$, $X^{a3}$, $X^{a4}$, and $X^{a5}$ are each independently at each occurrence $(-(R^{71})_{n21}-)_2N-(R^{72})_{n22}-$, $-(R^{71})_{n21}-X^3-(R^{72})_{n22}-$, $-R^{73}-$, or $-Y-O-$;

$R^{71}$ is each independently at each occurrence $-(CH_2)_{n23}-$, an o-, m-, or p-phenylene group, which may be substituted with one or more fluorine atoms;

n23 is each independently at each occurrence an integer of 1 to 20;

$R^{72}$ is each independently at each occurrence $-(CH_2)_{n24}-$, an o-, m-, or p-phenylene group, which may be substituted with one or more fluorine atoms;

n24 is each independently at each occurrence an integer of 1 to 20;

n21 is each independently at each occurrence 0 or 1;

n22 is each independently at each occurrence 0 or 1;

the sum of n21 and n22 is 1 or more;

$X^3$ is each independently at each occurrence $-O-$, $-(OR^{74})_{n25}-$, $-S-$, $-C(=O)-$, $-C(=O)O-$, $-O-C(=O)-$, $-O-C(=O)-O-$, $-Si(R^{75})_2-$, $-(Si(R^{75})_2O)_{n26}-Si(R^{75})_2-$, $-NR^3C(=O)-$, $-C(=O)NR^3-$, $-NR^3C(=O)NR^3-$, $-NR^3C(=O)O-$, $-O-C(=O)NR^3-$, $-NR^3-$, $-SO_2NR^3-$, or $-SO_2-$;

$R^{74}$ is each independently at each occurrence a $C_{1-6}$ alkylene group;

n25 is each independently at each occurrence an integer of 1 to 5;

$R^{75}$ is each independently at each occurrence a phenyl group, a $C_{1-6}$ alkyl group, or a $C_{1-6}$ alkoxy group;

n26 is each independently at each occurrence an integer of 1 to 100;

$R^3$ is each independently at each occurrence a hydrogen atom, a phenyl group, or an alkyl group having 1 to 6 carbon atoms;

$R^{73}$ is each independently at each occurrence $-(CH_2)_{n27}-$;

n27 is an integer of 1 to 20; and

Y is a di- to hexavalent hydrocarbon group and has a silicon atom and/or a siloxane bond;

$X^{a2}$ is a single bond or a divalent organic group;

β1, β2, β3, and β4 are each independently at each occurrence an integer of 1 to 9;

t is each independently at each occurrence an integer of 2 to 10;

$R^{31}$ is each independently at each occurrence a hydrogen atom or a halogen atom;

$R^{32}$ is each independently at each occurrence a hydrogen atom or a monovalent organic group;

in formula (A1), there is at least one $R^a{}_m1R^b{}_{3-m1}Si-$ wherein m1 is 1 to 3, and in formula (A2), there is at least one $R^a{}_m1R^b{}_{3-m1}Si-$ wherein m1 is 1 to 3;

$R^{f1}$ is each independently at each occurrence $R^{41}{}_{r1}R^{42}{}_{r2}R^{43}{}_{r3}Si\text{-}Z^1-$;

$Z^1$ is each independently at each occurrence an oxygen atom or a divalent organic group;

$R^{41}$ is each independently at each occurrence $R^{f1}$;

$R^{f1'}$ has the same definition as that of $R^{f1}$;

in $R^{f1}$, the number of Si atoms linearly connected via the group $Z^1$ is up to 5;

$R^{42}$ is each independently at each occurrence a hydroxyl group or a hydrolyzable group;

$R^{43}$ is each independently at each occurrence a hydrogen atom or a monovalent organic group;

r1 is each independently at each occurrence an integer of 0 to 3;

r2 is each independently at each occurrence an integer of 0 to 3;

r3 is each independently at each occurrence an integer of 0 to 3;

in each $R^{41}_{f1}R^{42}_{f2}R^{43}_{f3}Si\text{-}Z^1\text{—}$, the sum of r1, r2, and r3 is 3;

$R^{f2}$ is each independently at each occurrence a hydroxyl group or a hydrolyzable group;

$R^{f3}$ is each independently at each occurrence a hydrogen atom or a monovalent organic group;

p1 is each independently at each occurrence an integer of 0 to 3;

p2 is each independently at each occurrence an integer of 0 to 3;

p3 is each independently at each occurrence an integer of 0 to 3;

in each $R^{f3}_{p3}R^{f2}_{p2}R^{f1}_{p1}Si\text{—}$, the sum of p1, p2, and p3 is 3, and in formula (A3), there are at least two Si atoms to which a hydroxyl group or a hydrolyzable group binds;

$R^{g1}$ is each independently at each occurrence $R^{51}_{s1}R^{52}_{s2}R^{53}_{s3}C\text{-}Z^2\text{—}$;

$Z^2$ is each independently at each occurrence an oxygen atom or a divalent organic group;

$R^{51}$ is each independently at each occurrence $R^{g1'}$;

$R^{g1'}$ has the same definition as that of $R^{g1}$;

in $R^{g1}$, the number of C atoms linearly connected via the group $Z^2$ is up to 5;

$R^{52}$ is each independently at each occurrence $R^{a}_{m1}R^{b}_{3-m1}Si\text{-}Z^3\text{—}$;

$Z^3$ is each independently at each occurrence an oxygen atom or a divalent organic group;

$R^{53}$ is each independently at each occurrence a hydrogen atom, a hydroxyl group, or a monovalent organic group;

s1 is each independently at each occurrence an integer of 0 to 3;

s2 is each independently at each occurrence an integer of 0 to 3;

s3 is each independently at each occurrence an integer of 0 to 3;

in each $R^{51}_{s1}R^{52}_{s2}R^{53}_{s3}C\text{-}Z^2\text{—}$, the sum of s1, s2, and s3 is 3;

$R^{g2}$ is each independently at each occurrence $R^{a}_{m1}R^{b}_{3-m1}Si\text{-}Z^4\text{—}$;

$Z^4$ is each independently at each occurrence an oxygen atom or a divalent organic group;

$R^{g3}$ is each independently at each occurrence a hydrogen atom, a hydroxyl group, or a monovalent organic group;

q1 is each independently at each occurrence an integer of 0 to 3;

q2 is each independently at each occurrence an integer of 0 to 3; and q3 is each independently at each occurrence an integer of 0 to 3;

in each $R^{g3}_{q3}R^{g2}_{q2}R^{g1}_{q1}C\text{—}$, the sum of q1, q2, and q3 is 3, and in formula (A4), there are at least two $R^{a}_{m1}R^{b}_{3-m1}Si\text{—}$ wherein m1 is 1 to 3.

2. The polyether group-containing compound according to claim 1, wherein the sum of n16 and n17 is 1 or more.

3. The polyether group-containing compound according to claim 1, wherein α is 2.

4. The polyether group-containing compound according to claim 1, wherein α is 1.

5. The polyether group-containing compound according to claim 1, wherein m1 is 2 or 3.

6. The polyether group-containing compound according to claim 1, wherein m1 is 3.

7. The polyether group-containing compound according to claim 1, wherein p1 is 3, and r2 is 3.

8. The polyether group-containing compound according to claim 1, wherein in formula (A4), q2 is 3, and m1 is 3.

9. The polyether group-containing compound according to claim 1, wherein β1, β2, β3, or β4 is 1.

10. The polyether group-containing compound according to claim 1, wherein Rf is a perfluoroalkyl group having 1 to 16 carbon atoms.

11. The polyether group-containing compound according to claim 1, wherein PE is a group represented by any of the following formulae (a) to (c):

$$\text{—}(OC_3F_6)_d\text{—} \tag{a}$$

wherein d is an integer of 1 to 200;

$$\text{—}(OC_4F_8)_c\text{—}(OC_3F_6)_d\text{—}(OC_2F_4)_e\text{—}(OCF_2)_f\text{—} \tag{b}$$

wherein c and d are each independently an integer of 0 or more and 30 or less;

e and f are each independently an integer of 1 or more and 200 or less;

the sum of c, d, e, and f is an integer of 10 or more and 200 or less; and the occurrence order of the respective repeating units enclosed in parentheses provided with a subscript c, d, e, or f is not limited in the formula; and $$(R^6\text{—}R^7)_g\text{—} \tag{c}$$

wherein $R^6$ is $OCF_2$ or $OC_2F_4$;

$R^7$ is a group selected from $OC_2F_4$, $OC_3F_6$, $OC_4F_8$, $OC_5F_{10}$, and $OC_6F_{12}$, or is a combination of two or three groups selected from these groups; and g is an integer of 2 to 100.

* * * * *